United States Patent
Durette et al.

[11] Patent Number: 5,929,094
[45] Date of Patent: Jul. 27, 1999

[54] HETEROARYL SPIROETHERCYCLOALKYL TACHYKININ RECEPTOR ANTAGONISTS

[75] Inventors: Philippe Durette, New Providence; Ihor Kopka, Millburn; Malcolm MacCoss, Freehold; Sander Mills, Scotch Plains, all of N.J.

[73] Assignee: Merck & Co., Inc., Rahway, N.J.

[21] Appl. No.: 08/956,181

[22] Filed: Oct. 22, 1997

Related U.S. Application Data

[60] Provisional application No. 60/029,310, Oct. 25, 1996.

[51] Int. Cl.$^6$ .......................... A61K 31/44; C07D 405/14
[52] U.S. Cl. .................. 514/340; 546/268.4; 546/272.4; 548/217; 548/304.7; 548/466; 549/462
[58] Field of Search .............................. 546/268.4, 272.4, 546/271.7, 273.7, 274.1, 277.4, 284.4; 514/340, 341, 338, 339; 548/304.7, 217, 466; 549/462

[56] References Cited

U.S. PATENT DOCUMENTS

| | | | |
|---|---|---|---|
| 5,300,524 | 4/1994 | Davidson et al. | 514/462 |
| 5,387,595 | 2/1995 | Mills et al. | 514/357 |
| 5,688,806 | 11/1997 | Desai et al. | 514/278 |

FOREIGN PATENT DOCUMENTS

| | | |
|---|---|---|
| WO 94/20500 | 9/1994 | WIPO . |
| WO 96/20197 | 7/1996 | WIPO . |
| WO 97/14671 | 4/1997 | WIPO . |
| WO 97/19084 | 5/1997 | WIPO . |
| WO 97/30055 | 8/1997 | WIPO . |
| WO 97/30056 | 8/1997 | WIPO . |
| WO 97/49710 | 12/1997 | WIPO . |

*Primary Examiner*—Alan L. Rotman
*Assistant Examiner*—Charanjit S. Aulakh
*Attorney, Agent, or Firm*—J. Eric Thies; David L. Rose

[57] ABSTRACT

The present invention is directed to certain novel compounds represented by structural formula I:

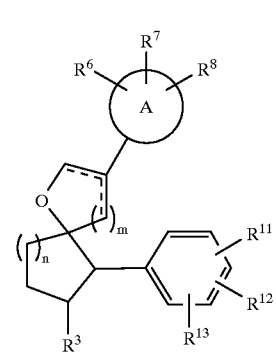

or a pharmaceutically acceptable salt thereof, wherein $R^3$, $R^6$, $R^7$, $R^8$, $R^{11}$, $R^{12}$, $R^{13}$, A, m, n and the dashed lines are defined herein. The invention is also concerned with pharmaceutical formulations comprising these novel compounds as active ingredients and the use of the novel compounds and their formulations in the treatment of certain disorders. The compounds of this invention are tachykinin receptor antagonists and are useful in the treatment of inflammatory diseases, pain or migraine, asthma and emesis.

13 Claims, No Drawings

HETEROARYL SPIROETHERCYCLOALKYL TACHYKININ RECEPTOR ANTAGONISTS

CROSS REFERENCE TO RELATED APPLICATIONS

This application claims priority under 35 U.S.C. § 119(e) from U.S. Ser. No. 60/029,310, filed Oct. 25, 1996.

BACKGROUND OF THE INVENTION

Analgesia has historically been achieved in the central nervous system by opiates and analogs which are addictive, and peripherally by cyclooxygenase inhibitors that have gastric side effects. Substance P antagonists may induce analgesia both centrally and peripherally. In addition, substance P antagonists are inhibitory of neurogenic inflammation.

The neuropeptide receptors for substance P (neurokinin-1; NK-1) are widely distributed throughout the mammalian nervous system (especially brain and spinal ganglia), the circulatory system and peripheral tissues (especially the duodenum and jejunum) and are involved in regulating a number of diverse biological processes. This includes sensory perception of olfaction, vision, audition and pain, movement control, gastric motility, vasodilation, salivation, and micturition (B. Pernow, *Pharmacol. Rev.*, 1983, 35, 85–141). The NK-1 and NK-2 receptor subtypes are implicated in synaptic transmission (Laneuville et al., *Life Sci.*, 42: 1295–1305 (1988)).

The receptor for substance P is a member of the superfamily of G protein-coupled receptors. This superfamily is an extremely diverse group of receptors in terms of activating ligands and biological functions. In addition to the tachykinin receptors, this receptor superfamily includes the opsins, the adrenergic receptors, the muscarinic receptors, the dopamine receptors, the serotonin receptors, a thyroid-stimulating hormone receptor, a luteinizing hormone-choriogonadotropic hormone receptor, the product of the oncogene ras, the yeast mating factor receptors, a *Dictyostelium* cAMP receptor, and receptors for other hormones and neurotransmitters (A. D. Hershey, et al., *J. Biol. Chem.*, 1991, 226, 4366–4373).

Substance P (also called "SP" herein) is a naturally occurring undecapeptide belonging to the tachykinin family of peptides, the latter being so-named because of their prompt contractile action on extravascular smooth muscle tissue. In addition to SP the known mammalian tachykinins include neurokinin A and neurokinin B. The current nomenclature designates the receptors for SP, neurokinin A, and neurokinin B as NK-1, NK-2, and NK-3, respectively. More specifically, substance P is a neuropeptide that is produced in mammals and possesses a characteristic amino acid sequence (Chang et al., *Nature New Biol.* 232, 86 (1971); D. F. Veber et al., U.S. Pat. No. 4,680,283).

Substance P is a pharmacologically-active neuropeptide that is produced in mammals and acts as a vasodilator, a depressant, stimulates salivation and produces increased capillary permeability. It is also capable of producing both analgesia and hyperalgesia in animals, depending on dose and pain responsiveness of the animal (see R. C. A. Frederickson et al., *Science*, 199, 1359 (1978); P. Oehme et al., *Science*, 208, 305 (1980)) and plays a role in sensory transmission and pain perception (T. M. Jessell, *Advan. Biochem. Psychopharmacol.* 28, 189 (1981)). For example, substance P is believed to be involved in the neurotransmission of pain sensations [Otsuka et al, "Role of Substance P as a Sensory Transmitter in Spinal Cord and Sympathetic Ganglia" in 1982 Substance P in the Nervous System, Ciba Foundation Symposium 91, 13–34 (published by Pitman) and Otsuka and Yanagisawa, "Does Substance P Act as a Pain Transmitter?" *TIPS*, 8 506–510 (Decemeber 1987)], specifically in the transmission of pain in migraine (see B. E. B. Sandberg et al., *Journal of Medicinal Chemistry*, 25, 1009 (1982); M. A. Moskowitz, *Trends Pharmacol. Sci.*, 13, 307–311 (1992)), and in arthritis (Levine, et al. *Science*, 226 547–549 (1984); M. Lotz, et al., *Science*, 235, 893–895 (1987)). Tachykinins have also been implicated in gastrointestinal (GI) disorders and diseases of the GI tract, such as inflammatory bowel disease [*Neuroscience*, 25 (3), 817–37 (1988) and D. Regoli in "Trends in Cluster Headache" Ed. F. Sicuteri et al., Elsevier Scientific Publishers, Amsterdam, pp. 85–95 (1987)], and emesis [*Trends Pharmacol. Sci.*, 2, 334–341 (1988), *Eur. J. Pharmacol.*, 249, R3–R4 (1993), *Brit. J. Pharmacol.*, 115, 84–94 (1995)].

It is also hypothesized that there is a neurogenic mechanism for arthritis in which substance P may play a role [Kidd et al., "A Neurogenic Mechanism for Symmetric Arthritis" in *The Lancet*, 11 November 1989 and Gronblad et al., "Neuropeptides in Synovium of Patients with Rheumatoid Arthritis and Osteoarthritis" in *J. Rheumatol.* 15(12) 1807–10 (1988)]. Therefore, substance P is believed to be involved in the inflammatory response in diseases such as rheumatoid arthritis and osteoarthritis [O'Byrne et al., *Arthritis and Rheumatism*, 33 1023–8 (1990)].

Evidence for the usefulness of tachykinin receptor antagonists in pain, headache, especially migraine, Alzheimer's disease, multiple sclerosis, attenuation of morphine withdrawal, cardiovascular changes, oedema, such as oedema caused by thermal injury, chronic inflammatory diseases such as rheumatoid arthritis, asthma/bronchial hyperreactivity and other respiratory diseases including allergic rhinitis, inflammatory diseases of the gut including ulcerative colitis and Chrohn's disease, ocular injury and ocular inflammatory diseases, proliferative vitreoretinopathy, irritable bowel syndrome and disorders of bladder function including cystitis and bladder detruser hyperreflexia is reviewed in "Tachykinin Receptors and Tachykinin Receptor Antagonists," C. A. Maggi, R. Patacchini, P. Rovero and A. Giachetti, *J. Auton. Pharmacol*, 13, 23–93 (1993); see also R. M. Snider, et al., *Chem. Ind.*, 11, 792–794 (1991). Neurokinin-1 receptor antagonists alone or in combination with bradykinin receptor antagonists may also be useful in the prevention and treatment of inflammatory conditions in the lower urinary tract, especially cystitis [Giuliani, et al., *J. Urology*, 150, 1014–1017 (1993)]. Other disease areas where tachykinin antagonists are believed to be useful are allergic conditions [Hamelet et al., *Can. J. Pharmacol. Physiol.*, 66, 1361–7 (1988)], immunoregulation [Lotz, et al., *Science*, 241 1218–21 (1988), Kimball, et al., *J. Immunol.*, 141 (10) 3564–9 (1988); A. Perianin, et al., *Biochem. Biophys. Res Commun.* 161, 520 (1989)], post-operative pain and nausea [C. Bountra, et al., *Eur. J. Pharmacol.*, 249, R3–R4 (1993), F. D. Tattersall, et al., *Neuropharmacology*, 33, 259–260 (1994)], vasodilation, bronchospasm, reflex or neuronal control of the viscera [Mantyh et al., *PNAS*, 85, 3235–9 (1988)] and, possibly by arresting or slowing β-amyloid-mediated neurodegenerative changes [Yankner et al., *Science*, 250, 279–82 (1990)] in senile dementia of the Alzheimer type, Alzheimer's disease and Downs Syndrome. Substance P may also play a role in demyelinating diseases such as multiple sclerosis and amyotrophic lateral sclerosis [J. Luber-Narod, et. al., poster C.I.N.P. XVIIIth Congress, Jun. 28th –Jul. 2nd, 1992], and in disorders of bladder function such as bladder detrusor hyper-reflexia [*Lancet*, May 16th 1992, 1239]. Antagonists selective for the neurokinin-1 (NK-1) and/or the neurokinin-2 (NK-2) receptor may be useful in the treatment of asthmatic disease (Frossard et al, *Life Sci.*, 49, 1941–1953 (1991); Advenier, et al., *Biochem. Biophys. Res. Comm.*, 184(3), 1418–1424 (1992); P. Barnes, et al., *Trends Pharmacol. Sci.*, 11, 185–189 (1993)). Tachykinin antagonists may also be useful in the treatment of small cell carcinomas, in particular small cell lung cancer (SCLC) [Langdon et al., *Cancer Research*, 52, 4554–7 (1992)].

It has furthermore been suggested that tachykinin receptor antagonists have utility in the following disorders: depression, dysthymic disorders, chronic obstructive airways disease, hypersensitivity disorders such as poison ivy, vasospastic diseases such as angina and Reynauld's disease, fibrosing and collagen diseases such as scleroderma and eosinophillic fascioliasis, reflex sympathetic dystrophy such as shoulder/hand syndrome, addiction disorders such as alcoholism, stress related somatic disorders, neuropathy, neuralgia, disorder related to immune enhancement or suppression such as systemic lupus erythmatosus (EPO Publication No. 0,436,334), ophthalmic diseases such as conjunctivitis, vernal conjunctivitis, and the like, and cutaneous diseases such as contact dermatitis, atopic dermatitis, urricaria, and others eczematoid dermatitis (EPO Publication No. 0,394,989).

Substance P antagonists may be useful in mediating neurogenic mucus secretion in mammalian airways and hence provide treatment and symptomatic relief in diseases characterized by mucus secretion, in particular, cystic fibrosis [S. Ramnarine, et al., abstract presented at 1993 ALA/ATS Int'l Conference, May 16–19 , 1993, published in *Am. Rev. of Respiratory Dis.*, May 1993].

In the recent past, some attempts have been made to provide peptide-like substances that are antagonists for the receptors of substance P and other tachykinin peptides in order to more effectively treat the various disorders and diseases mentioned above. For example Lowe, *Drugs of the Future*, 17 (12) 1115–1121 (1992) and EPO Publication Nos. 0,347,802, 0,401,177 and 0,412,452 disclose various peptides as neurokinin A antagonists. Also, PCT Patent Publication WO 93/14113 discloses certain peptides as tachykinin antagonists. In addition, EPO Publication No. 0,336,230 discloses heptapeptides which are substance P antagonists useful in the treatment of asthma. U.S. Pat. No. 4,680,283, also discloses peptidal analogs of substance P. Certain inhibitors of tachykinins have been described in U.S. Pat. No. 4,501,733, by replacing residues in substance P sequence by Trp residues. A further class of tachykinin receptor antagonists, comprising a monomeric or dimeric hexa- or heptapeptide unit in linear or cyclic form, is described in GB-A-2216529. The peptide-like nature of such substances make them too labile from a metabolic point of view to serve as practical therapeutic agents in the treatment of disease. The non-peptidic antagonists of the present invention, on the other hand, do not possess this drawback, as they are expected to be more stable from a metabolic point of view than the previously-discussed agents.

It is known that in the central nervous system baclofen [β-(aminoethyl)-4-chlorobenzenepropanoic acid] effectively blocks the excitatory activity of substance P. WIPO patent applications (PCT Publication Nos. WO 90/05525, WO 90/05729, WO 91/18899, WO 92/12151 and WO 92/12152) and publications (*Science*, 251, 435–437 (1991); *Science*, 251, 437–439 (1991); *J. Med. Chem.*, 35, 2591–2600 (1992)) disclose 2-arylmethyl-3-substituted amino-quinuclidine derivatives which are disclosed as being useful as substance P antagonists for treating gastrointestinal disorders, central nervous system disorders, inflammatory diseases and pain or migraine. A European patent application (EPO Publication No. 0,360,390) discloses various spirolactam-substituted amino acids and peptides which are antagonists or agonists of substance P. A WIPO patent application (PCT Publication No. WO 92/06079) discloses fused-ring analogs of nitrogen-containing nonaromatic heterocycles as useful for the treatment of diseases mediated by an excess of substance P. A WIPO patent application (PCT Publication No. WO 92/15585 discloses 1-azabicyclo[3.2.2] nonan-3-amine derivatives as substance P antagonists. A WIPO patent application (PCT Publication No. WO 93/10073) discloses ethylenediamine derivatives as substance P antagonists. PCT Publication No. WO 93/01169 discloses certain aromatic compounds as tachykinin receptor antagonists. A publication (*Life Sci.*, 50, PL101–PL106 (1992)) discloses a 4-phenyl piperidine derivative as an antagonist of the neurokinin A (NK2) receptor.

Howson et al. (*Biorg. & Med. Chem. Lett.*, 2 (6), 559–564 (1992)) disclose certain 3-amino and 3-oxy quinuclidine compounds and their binding to substance P receptors. EPO Publication 0,499,313 discloses certain 3-oxy and 3-thio azabicyclic compounds as tachykinin antagonists. U.S. Pat. No. 3,506,673 discloses certain 3-hydroxy quinuclidine compounds as central nervous system stimulants. EPO Publication 0,436,334 discloses certain 3-aminopiperidine compounds as substance P antagonists. U.S. Pat. No. 5,064,838 discloses certain 1,4-disubstituted piperidinyl compounds as analgesics. PCT Publication No. WO 92/12128 discloses certain piperidine and pyrrolidine compounds as analgesics. Peyronel, et al.(*Biorg & Med. Chem. Lett.*, 2 (1), 37–40 (1992)) disclose a fused ring pyrrolidine compound as a substance P antagonist. EPO Publication No. 0,360,390 discloses certain spirolactam derivatives as substance P antagonists. U.S. Pat. No. 4,804,661 discloses certain piperazine compounds as analgesics. U.S. Pat. No. 4,943,578 discloses certain piperazine compounds useful in the treatment of pain. PCT Publication No. WO 92/01679 discloses certain 1,4-disubstituted piperazines useful in the treatment of mental disorders in which a dopaminergic deficit is implicated. PCT Publication No. WO 94/00440, EPO Publication No. 0,577,394 and PCT Publication No. WO 95/16679 disclose certain morpholine and thiomorpholine compounds as substance P antagonists. U.S. Pat. No. 5,387, 595 and *Bioorg. & Med. Chem. Lett.*, 1345 (1995) disclose certain alicyclic compounds as tachykinin receptor antagonist. PCT Publications WO 95/06645 and WO 95/08549 discloses certain 3-amino-piperidines as tachykinin antagonists. PCT Publication No. WO 96/20197 disclose certain spiroketal morpholine compounds as substance P antagonists.

SUMMARY OF THE INVENTION

The present invention is directed to compounds of the structural formula I:

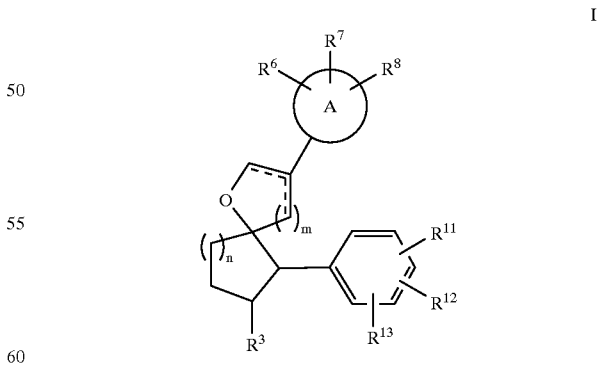

or a pharmaceutically acceptable salt thereof, wherein $R^3$, $R^6$, $R^7$, $R^8$, $R^{11}$, $R^{12}$, $R^{13}$, A, m, n and the dashed lines are hereinafter defined. The invention is also concerned with pharmaceutical formulations comprising these novel compounds as active ingredients and the use of the novel compounds and their formulations in the treatment of certain disorders. The compounds of this invention are tachykinin receptor antagonists and are useful in the treatment of inflammatory diseases, pain or migraine, asthma and emesis.

DETAILED DESCRIPTION OF THE INVENTION

The present invention is directed to the novel compound of the structural formula I:

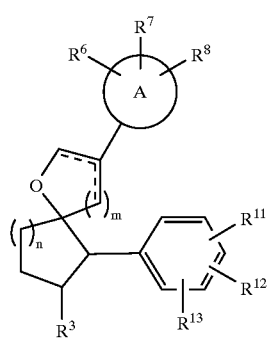

or a pharmaceutically acceptable salt thereof, wherein:
$R^3$ is selected from the group consisting of:
(1) hydrogen,
(2) $C_{1-8}$ alkyl,
(3) —$R^4$, and
(4) $C_{1-6}$ alkyl substituted with —$R^4$;
$R^4$ is selected from the group consisting of:
(1) hydroxy,
(2) $C_{1-6}$ alkoxy,
(3) phenyl-$C_{1-3}$ alkoxy,
(4) phenyl,
(5) —CN,
(6) halo, wherein halo is fluoro, chloro, bromo or iodo,
(7) —$NR^9R^{10}$, wherein $R^9$ and $R^{10}$ are independently selected from:
(a) hydrogen,
(b) $C_{1-6}$ alkyl,
(c) $C_{2-6}$ alkenyl,
(d) $C_{2-6}$ alkoxy,
(e) phenyl,
(f) ($C_{1-6}$ alkyl)-phenyl,
(g) ($C_{1-6}$ alkyl)-hydroxy,
(h) ($C_{1-6}$ alkyl)-halo,
(i) ($C_{16}$ alkyl)-poly-halo,
(j) ($C_{1-6}$ alkyl)-$CONR^{11}R^{12}$, wherein $R^{11}$ and $R^{12}$ are independently selected from hydrogen and $C_{1-4}$ alkyl, and
(k) ($C_{1-6}$ alkyl)-($C_{1-4}$ alkoxy),
or $R^9$ and $R^{10}$ may be joined together to form a 3–8 membered heterocyclic ring which may contain another heterogroup selected from: —O—, —NH—, —N($C_{1-6}$ alkyl)-, and —S—;
(8) —$NR^9$—$COR^{10}$,
(9) —$NR^9$—$CO_2R^{10}$,
(10) —CO—$NR^9R^{10}$,
(11) —$COR^9$,
(12) —$CO_2R^9$,
(13) heterocycle, wherein the heterocycle is selected from the group consisting of:
(A) benzimidazolyl,
(B) benzofuranyl,
(C) benzothiophenyl,
(D) benzoxazolyl,
(E) furanyl,
(F) imidazolyl,
(G) indolyl,
(H) isooxazolyl,
(I) isothiazolyl,
(J) oxadiazolyl,
(K) oxazolyl,
(L) pyrazinyl,
(M) pyrazolyl,
(N) pyridyl,
(O) pyrimidyl,
(P) pyrrolyl,
(Q) quinolyl,
(R) tetrazolyl,
(S) thiadiazolyl,
(T) thiazolyl,
(U) thienyl,
(V) triazolyl,
(W) azetidinyl,
(X) 1,4-dioxanyl,
(Y) hexahydroazepinyl,
(Z) piperazinyl,
(AA) piperidinyl,
(AB) pyrrolidinyl,
(AC) morpholinyl,
(AC) thiomorpholinyl,
(AD) dihydrobenzimidazolyl,
(AE) dihydrobenzofuranyl,
(AF) dihydrobenzothiophenyl,
(AG) dihydrobenzoxazolyl,
(AH) dihydrofuranyl
(AI) dihydroimidazolyl,
(AJ) dihydroindolyl,
(AK) dihydroisooxazolyl,
(AL) dihydroisothiazolyl,
(AM) dihydrooxadiazolyl,
(AN) dihydrooxazolyl,
(AO) dihydropyrazinyl,
(AP) dihydropyrazolyl,
(AQ) dihydropyridinyl,
(AR) dihydropyrimidinyl,
(AS) dihydropyrrolyl,
(AT) dihydroquinolinyl,
(AU) dihydrotetrazolyl,
(AV) dihydrothiadiazolyl,
(AW) dihydrothiazolyl,
(AX) dihydrothienyl,
(AY) dihydrotriazolyl,
(AZ) dihydroazetidinyl,
(BA) tetrahydrofuranyl, and
(BB) tetrahydrothienyl,
and wherein the heterocycle is unsubstituted or substituted with one or more substituent(s) selected from:
(i) $C_{1-6}$ alkyl, unsubstituted or substituted with halo, —$CF_3$, —$OCH_3$, or phenyl,
(ii) $C_{1-6}$ alkoxy,
(iii) oxo,
(iv) hydroxy,
(v) thioxo,
(vi) —$SR^9$,
(vii) halo,
(viii) cyano,
(ix) phenyl,
(x) trifluoromethyl,
(xi) —$(CH_2)_p$—$NR^9R^{10}$, wherein p is 0, 1, 2, 3 or 4,
(xii) —$NR^9COR^{10}$, (xiii) —CONR$^9$R$^{10}$,
(xiv) —CO$_2$R$^9$, and
(xv) —(CH$_2$)$_p$—OR$^9$,
(14) —CO-heterocycle, wherein heterocycle is as defined above,
(15) —NR$^9$-heterocycle, wherein heterocycle is as defined above,
(16) —NR$^9$—C$_{1-4}$ alkyl-heterocycle, wherein heterocycle is as defined above;

the circle A is a heteroaryl moiety which is selected from the group consisting of:
(A) benzimidazolyl,
(B) benzofuranyl,
(C) benzothiazoyl,
(D) benzodihydrofuranyl,
(E) benzothiophenyl,
(F) benzoxazolyl,
(G) furanyl,
(H) imidazolyl,
(I) indolyl,
(J) isooxazolyl,
(K) isothiazolyl,
(L) oxadiazolyl,
(M) oxazolyl,
(N) pyrazinyl,
(O) pyrazolyl,
(P) pyridyl,
(Q) pyrimidyl,
(R) pyrrolyl,
(S) quinolyl,
(T) tetrazolyl,
(U) thiadiazolyl,
(V) thiazolyl,
(W) thienyl,
(X) triazolyl,
(Y) dihydrobenzimidazolyl,
(Z) dihydrobenzofuranyl,
(AA) dihydrobenzothiophenyl,
(AB) dihydrobenzoxazolyl,
(AC) dihydrofuranyl
(AD) dihydroimidazolyl,
(AE) dihydroindolyl,
(AF) dihydroisooxazolyl,
(AG) dihydroisothiazolyl,
(AH) dihydrooxadiazolyl,
(AI) dihydropyrazinyl,
(AJ) dihydropyrazolyl,
(AK) dihydropyridinyl,
(AL) dihydropyrimidinyl, and
(AM) dihydroquinolinyl,
and wherein the heteroaryl moiety is unsubstituted or substituted with one or more substituent(s) selected from:
(i) C$_{1-6}$ alkyl, unsubstituted or substituted with halo, —CF$_3$, —OCH$_3$, or phenyl,
(ii) C$_{1-6}$ alkoxy,
(iii) oxo,
(iv) hydroxy,
(v) thioxo,
(vi) —SR$^9$,
(vii) halo,
(viii) cyano,
(ix) phenyl,
(x) trifluoromethyl,
(xi) —(CH$_2$)$_p$—NR$^9$R$^{10}$,
(xii) —NR$^9$COR$^{10}$,
(xiii) —CONR$^9$R$^{10}$,
(xiv) —CO$_2$R$^9$, and
(xv) —(CH$_2$)$_p$—OR$^9$;

R$^6$, R$^7$ and R$^8$ are independently selected from the group consisting of:
(1) hydrogen,
(2) C$_{1-6}$alkoxy,
(3) halo,
(4) C$_{1-6}$ alkyl, unsubstituted or substituted with one or more of the substituents selected from:
(a) hydroxy,
(b) oxo,
(c) C$_{1-6}$ alkoxy,
(d) phenyl-C$_{1-3}$ alkoxy,
(e) phenyl,
(f) —CN, (g) halo,
(h) —NR$^9$R$^{10}$,
(i) —NR$^9$—COR$^{10}$,
(j) —NR$^9$—CO$_2$R$^{10}$,
(k) —CO—NR$^9$R$^{10}$,
(l) —COR$^9$,
(m) —CO$_2$R$^9$,
(n) heterocycle, wherein heterocycle is as defined above,
(5) hydroxy,
(6) —CN,
(7) —CF$_3$,
(8) —OCF$_3$,
(9) —OCF$_2$H,
(10) —OCFH$_2$,
(11) —NO$_2$,
(12) —SR$^{14}$, wherein R$^{14}$ is hydrogen or C$_{1-6}$alkyl,
(13) —SOR$^{14}$,
(14) —SO$_2$R$^{14}$,
(15) —NR$^9$—COR$^{10}$,
(16) —CO—NR$^9$—COR$^{10}$,
(17) —NR$^9$R$^{10}$,
(18) —NR$^9$—CO$_2$R$^{10}$,
(19) —COR$^9$,
(20) —CO$_2$R$^9$,
(21) heterocycle, wherein heterocycle is as defined above,
(22) -(C$_{1-6}$alkyl)-heterocycle, wherein heterocycle is as defined above, and
(23) —N(heterocycle)—SO$_2$R$^{14}$, wherein heterocycle is as defined above;

R$^{11}$, R$^{12}$ and R$^{13}$ are independently selected from:
(1) hydrogen,
(2) C$_{1-6}$ alkyl, unsubstituted or substituted with one or more of the substituents selected from:
(a) hydroxy,
(b) oxo,
(c) C$_{1-6}$ alkoxy,
(d) phenyl-C$_{1-3}$ alkoxy,
(e) phenyl,
(f) —CN,
(g) halo,
(h) —NR$^9$R$^{10}$,
(i) —NR$^9$—COR$^{10}$,
(j) —NR$^9$—CO$_2$R$^{10}$,
(k) —CO—NR$^9$R$^{10}$,
(l) —COR$^9$, and
(m) —CO$_2$R$^9$,
(3) halo,
(4) —CN,
(5) —CF$_3$,
(6) —NO$_2$,
(7) hydroxy, (8) $C_{1-6}$alkoxy,
(9) —$COR^9$, and
(10) —$CO_2R^9$;

m is an integer selected from 1 or 2;

n is an integer selected from 0, 1 or 2;

each of the two dashed lines denotes the presence of either a single or a double bond between the indicated carbon atoms, with the proviso that at least one of the dashed lines indicates the presence of a single bond.

Asymmetric centers may be present in the compounds of the instant invention depending upon the nature of the various substituents on the molecule. Each such asymmetric center will independently produce two optical isomers and it is intended that all of the possible optical isomers and diastereomers in mixture and as pure or partially purified compounds are included within the ambit of this invention.

In addition compounds with carbon-carbon double bonds may occur in Z- and E- forms with all isomeric forms of the compounds being included in the present invention.

When any variable (e.g., alkyl, aryl, A, $R^4$, $R^6$, $R^7$, $R^8$, $R^9$, $R^{10}$, $R^{11}$, $R^{12}$, $R^{13}$, $R^{14}$, $R^{15}$, etc.) occurs more than one time in any variable or in Formula I, its definition on each ocurrence is independent of its definition at every other occurrence.

As used herein, the term "alkyl" includes those alkyl groups of a designated number of carbon atoms of either a straight, branched, or cyclic configuration. Examples of "alkyl" include methyl, ethyl, propyl, isopropyl, butyl, iso- sec- and tert-butyl, pentyl, hexyl, heptyl, 3-ethylbutyl, cyclopropyl, cyclobutyl, cyclopentyl, cyclohexyl, cycloheptyl, norbornyl, and the like. "Alkoxy" represents an alkyl group of indicated number of carbon atoms attached through an oxygen bridge, such as methoxy, ethoxy, propoxy, butoxy and pentoxy. "Alkenyl" is intended to include hydrocarbon chains of a specified number of carbon atoms of either a straight- or branched- configuration and at least one unsaturation, which may occur at any point along the chain, such as ethenyl, propenyl, butenyl, pentenyl, dimethylpentyl, and the like, and includes E and Z forms, where applicable. "Halogen" or "halo", as used herein, means fluoro, chloro, bromo and iodo.

The term "aryl" means phenyl or naphthyl either unsubstituted or substituted with one or more substituents selected from the group consisting of halo, $C_{1-4}$-alkyl, $C_{1-4}$-alkoxy, —$NO_2$, —$CF_3$, $C_{1-4}$-alkylthio, OH, —$N(R^9R^{10})$, —$CO_2R^9$, $C_{1-4}$-perfluoroalkyl, $C_{3-6}$-perfluorocycloalkyl, and tetrazol-5-yl.

The term "heteroaryl" (unless otherwise defined) means an unsubstituted, monosubstituted or disubstituted five or six membered aromatic heterocycle comprising from 1 to 3 heteroatoms selected from the group consisting of O, N and S and wherein the substituents are members selected from the group consisting of —OH, —SH, —$C_{1-4}$-alkyl, —$C_{1-4}$-alkoxy, —$CF_3$, halo, —$NO_2$, —$CO_2R^9$,—$N(R^9R^{10})$ and a fused benzo group.

As will be understood by those skilled in the art, pharmaceutically acceptable salts include, but are not limited to salts with inorganic acids such as hydrochloride, sulfate, phosphate, diphosphate, hydrobromide, and nitrate or salts with an organic acid such as malate, maleate, fumarate, tartrate, succinate, citrate, acetate, lactate, methanesulfonate, p-toluenesulfonate, 2-hydroxyethylsulfonate, pamoate, salicylate and stearate. Similarly, pharmaceutically acceptable cations include, but are not limited to sodium, potassium, calcium, aluminum, lithium and ammonium.

A preferred embodiment of the present invention includes those compounds of structural formula I, or a pharmaceutically acceptable salt thereof, wherein:

$R^3$ is selected from the group consisting of:
(1) —$R^4$, and
(2) $C_{1-6}$ alkyl substituted with —$R^4$;

$R^4$ is selected from the group consisting of:
(1) —$NR^9R^{10}$, wherein $R^9$ and $R^{10}$ are independently selected from:
  (a) hydrogen,
  (b) $C_{1-6}$ alkyl,
  (c) ($C_{1-6}$ alkyl)-hydroxy, and
  (d) ($C_{1-6}$ alkyl)-($C_{1-4}$ alkoxy),
(2) —CO—$NR^9R^{10}$,
(3) —$NR^9$—$COR^{10}$,
(4) heterocycle, wherein the heterocycle is selected from the group consisting of:
  (A) imidazolyl,
  (B) triazolyl,
  (C) tetrazolyl,
  (D) pyridyl,
  (E) piperazinyl,
  (F) piperidinyl,
  (G) pyrrolidinyl,
  (H) morpholinyl,
  and wherein the heterocycle is unsubstituted or substituted with one or more substituent(s) selected from:
  (i) $C_{1-6}$ alkyl, unsubstituted or substituted with halo, —$CF_3$, —$OCH_3$, or phenyl,
  (ii) $C_{1-6}$ alkoxy,
  (iii) oxo, and
  (iv) hydroxy,
(5) —CO-heterocycle, wherein heterocycle is as defined above;

the circle A is a heteroaryl moiety which is selected from the group consisting of:
(A) benzofuranyl,
(B) indolyl,
(C) isooxazolyl,
(D) pyridyl,
(E) pyrimidyl, and
(F) dihydrobenzofuranyl,
and wherein the heteroaryl moiety is unsubstituted or substituted with one or more substituent(s) selected from:
(i) $C_{1-6}$ alkyl, unsubstituted or substituted with halo, —$CF_3$, —$OCH_3$, or phenyl,
(ii) $C_{1-6}$ alkoxy,
(iii) oxo,
(iv) hydroxy,
(v) thioxo,
(vi) —$SR^9$,
(vii) halo,
(viii) cyano,
(ix) phenyl,
(x) trifluoromethyl,
(xi) —$(CH_2)_p$—$NR^9R^{10}$,
(xii) —$NR^9COR^{10}$,
(xiii) —$CONR^9R^{10}$,
(xiv) —$CO_2R^9$, and
(xv) —$(CH_2)_p$—$OR^9$;

$R^6$, $R^7$ and $R^8$ are independently selected from the group consisting of:
(1) hydrogen,
(2) —$CF_3$,
(3) —$OCF_3$,
(4) —F,
(5) $C_{1-6}$alkyl,
(6) $C_{1-6}$alkoxy, and (7) heterocycle, wherein the heterocycle is selected from the group consisting of:
(A) imidazolyl,
(B) triazolyl,
(C) tetrazolyl,
(D) pyridyl,
(E) piperazinyl,
(F) piperidinyl,
(G) pyrrolidinyl, and
(H) morpholinyl,
and wherein the heterocycle is unsubstituted or substituted with one or more substituent(s) selected from:
(i) $C_{1-6}$ alkyl, unsubstituted or substituted with halo, —$CF_3$, —$OCH_3$, or phenyl,
(ii) $C_{1-6}$ alkoxy,
(iii) oxo, and
(iv) hydroxy;

$R^{11}$, $R^{12}$ and $R^{13}$ are independently selected from:
(1) hydrogen, and
(2) fluoro;

m is an integer selected from 1 or 2;
n is an integer selected from 1 or 2;
each of the two dashed lines denotes the presence of either a single or a double bond between the indicated carbon atoms, with the proviso that at least one of the dashed lines indicates the presence of a single bond.

In the present invention it is preferred that $R^3$ is selected from the group consisting of:
(1) —$CH_2$—N($C_{1-6}$ alkyl)($C_{1-6}$ alkyl),
(2) —$CH_2$—NH($C_{1-6}$ alkyl),
(3) —$CH_2$—N($C_{1-6}$ alkyl)($CH_2CH_2$—F),
(4) —$CH_2$-pyrrolidinyl,
(5) —$CH_2$-morpholinyl,
(6) —N($C_{1-6}$ alkyl)($C_{1-6}$ alkyl), and
(7) —NH($C_{1-6}$ alkyl).

In the compounds of the present invention wherein $R^3$ is —$R^4$ or $C_{1-6}$ alkyl substituted with —$R^4$, it is preferred that $R^4$ is selected from the group consisting of:
(1) —$NR^9R^{10}$, wherein $R^9$ and $R^{10}$ are independently selected from:
(a) hydrogen,
(b) $C_{1-6}$ alkyl,
(c) ($C_{1-6}$ alkyl)-hydroxy, and
(d) ($C_{1-6}$ alkyl)-halo,
(2) —CO—$NR^9R^{10}$,
(3) —$NR^9$—$COR^{10}$,
(4) heterocycle, wherein the heterocycle is selected from the group consisting of:
(A) imidazolyl,
(B) triazolyl,
(C) tetrazolyl,
(D) pyridyl,
(E) piperazinyl,
(F) piperidinyl,
(G) pyrrolidinyl,
(H) morpholinyl,
and wherein the heterocycle is unsubstituted or substituted with one or more substituent(s) selected from:
(i) $C_{1-6}$ alkyl, unsubstituted or substituted with halo, —$CF_3$, —$OCH_3$, or phenyl,
(ii) $C_{1-6}$ alkoxy,
(iii) oxo, and
(iv) hydroxy,
(5) —CO-heterocycle, wherein heterocycle is as defined above.

In the present invention it is preferred that A is selected from the group consisting of:
(A) imidazolyl,
(B) triazolyl,
(C) tetrazolyl,
(D) pyridyl,
(E) piperazinyl,
(F) piperidinyl,
(G) pyrrolidinyl,
(H) morpholinyl,
and wherein the heterocycle is unsubstituted or substituted with one or more substituent(s) selected from:
(i) $C_{1-6}$ alkyl, unsubstituted or substituted with halo, —$CF_3$, —$OCH_3$, or phenyl,
(ii) $C_{1-6}$ alkoxy,
(iii) oxo, and
(iv) hydroxy, In the present invention it is particularly preferred that $R^6$, $R^7$ and $R^8$ are independently selected from the group consisting of:
(1) hydrogen,
(2) —$CF_3$,
(3) —$OCF_3$,
(4) $C_{1-4}$alkoxy, and
(5) heterocycle, wherein the heterocycle is selected from the group consisting of:
(A) tetrazolyl,
(B) imidazolyl,
(C) triazolyl,
(D) pyridyl, and
(E) isooxazolyl,
and wherein the heterocycle is unsubstituted or substituted with one or more substituent(s) selected from:
(i) $C_{1-4}$ alkyl,
(ii) -cyclopropyl, and
(iii) —$CF_3$.

In the present invention it is particularly preferred that $R^{11}$, $R^{12}$ and $R^{13}$ are independently selected from:
(1) hydrogen, and
(2) fluoro.

In the present invention it is particularly preferred that m is 1 and n is 1.

In the present invention a particularly preferred embodiment is directed to those compounds in which the phenyl ring bearing $R^{11}$, $R^{12}$ and $R^{13}$ is unsubstituted phenyl or is parafluorophenyl.

Specific compounds within the present invention include:
methyl [3-(SR), 5-(RS), 6-(SR), 7-(SR)]-6-(4-fluorophenyl)-3-(2-methoxy-5-((5-trifluoromethyl)tetrazol-1-yl)phenyl)-1-oxaspiro[4.4]nonane-7-carboxylate;

(5R,6S ,7S)-6-(4-fluorophenyl)-3- [2-methoxy-5-(5-trifluoromethyl-tetrazol-1-yl)-pyridin-3-yl ]-1-oxaspiro[4.4]non-3-ene-7-carboxylic acid methyl ester;

(3S ,5R,6S,7S)-6-(4-fluorophenyl)-3-[2-methoxy-5-(5-trifluoromethyl-tetrazol-1-yl)-pyridin-3-yl]-1-oxaspiro[4.4]nonane-7-carboxylic acid methyl ester;

(5R,6S,7S)-6-(4-fluorophenyl)-3-[2-methoxy-5-(5-trifluoromethyl-tetrazol-1-yl)-pyridin-2-yl]-1-oxaspiro[4.4]non-3-ene-7-carboxylic acid methyl ester;

(3S,5R,6S,7S)-6-(4-fluorophenyl)-3-[3-methoxy-6-(5-trifluoromethyl-tetrazol-1-yl)-pyridin-2-yl]-1-oxaspiro[4.4]nonane-7-carboxylic acid methyl ester;

(5R,6S,7S)-6-(4-fluorophenyl)-3-[5-trifluoromethoxy-dihydrobenzofuran-7-yl]-1-oxaspiro[4.4]non-3-ene-7-carboxylic acid methyl ester;

(5R,6S, 7S)-6-(4-fluorophenyl)-3-(1-methyl-5-trifluoromethyl-benzimidazol-7-yl)-1-oxaspiro [4.4]non-3-ene-7-carboxylic acid methyl ester;

(5R,6S, 7S)-6-(4-fluorophenyl)-3-[1-(tert-butyloxycarbonyl)-6-trifluoromethyl-benzimidazol-4-yl]-1-oxaspiro[4.4]non-3-ene-7-carboxylic acid methyl ester;

(5R, 6S, 7S)-6-(4-fluorophenyl)-3-(5-trifluoromethyl-benzimidazol-7-yl)-1-oxaspiro [4.4]nonane-7-carboxylic acid methyl ester;

(5R, 6S, 7S)-6-(4-fluorophenyl)-3-(((5-trifluoromethyl)tetrazol-1-yl)-1H-indol-7-yl)-1-oxaspiro[4.4]non-3-ene-7-carboxylic acid methyl ester;

(5R, 6S, 7S)-6-(4-fluorophenyl)-3-(((5-trifluoromethyl)tetrazol-1-yl)-1H-indol-7-yl)-1-oxaspiro[4.4]nonane-7-carboxylic acid methyl ester;

(3S,5R,6S,7S)-6-(4-fluorophenyl)-3-[3-methoxy-6-(5-trifluoromethyl-tetrazol-1-yl)-pyridin-2-yl]-1-oxaspiro[4.4]nonane-7-carboxylic acid methyl ester;

(5R,6S,7S)-6-(4-fluorophenyl)-3-[5-trifluoromethoxy-dihydrobenzofuran-7-yl]-1-oxaspiro[4.4]non-3-ene-7-carboxylic acid methyl ester;

(5R,6S, 7S)-6-(4-fluorophenyl)-3-(1-methyl-5-trifluoromethyl-benzimidazol-7-yl)-1-oxaspiro[4.4]non-3-ene-7-carboxylic acid methyl ester;

(5R,6S, 7S)-6-(4-fluorophenyl)-3-[1-(tert-butyloxycarbonyl)-6-trifluoromethyl-benzimidazol-4-yl]-1-oxaspiro[4.4]non-3-ene-7-carboxylic acid methyl ester;

(5R, 6S, 7S)-6-(4-fluorophenyl)-3-(5-trifluoromethyl-benzimidazol-7-yl)-1-oxaspiro[4.4]nonane-7-carboxylic acid methyl ester;

(5R, 6S, 7S)-6-(4-fluorophenyl)-3-(((5-trifluoromethyl)tetrazol-1-yl)-1H-indol-7-yl)-1-oxaspiro[4.4]non-3-ene-7-carboxylic acid methyl ester;

(5R, 6S, 7S)-6-(4-fluorophenyl)-3-(((5-trifluoromethyl)tetrazol-1-yl)-1H-indol-7-yl)-1-oxaspiro[4.4]nonane-7-carboxylic acid methyl ester;

(3S, 5R, 6S, 7S)-6-(4-fluorophenyl)-3-(((5-trifluoromethyl)tetrazol-1-yl)-1H-indol-7-yl)-1-oxaspiro[4.4]nonane-7-methanol;

(3S, 5R, 6S, 7S)-7-(dimethylaminomethyl)-6-(4-fluorophenyl)-3-(((5-trifluoromethyl)tetrazol-1-yl)-1H-indol-7-yl)-1-oxaspiro[4.4]nonane;

(5R, 6S, 7S)-7-6-(4-fluorophenyl)-3-(((5-trifluoromethyl)tetrazol-1-yl)-1-methyl-indol-7-yl)-1-oxaspiro [4.4]non-3-ene-7-methanol;

(3S, 5R, 6S, 7S)-7-6-(4-fluorophenyl)-3-(((5-trifluoromethyl)tetrazol-1-yl)-1-methyl-indol-7-yl)-1-oxaspiro[4.4]nonane-7-methanol;

(5R, 6S, 7S)-7-(2-fluoroethylaminomethyl)-6-(4-fluorophenyl)-3-(((5-trifluoromethyl)tetrazol-1-yl)-1-methyl-indol-7-yl)-1-oxaspiro[4.4]non-3-ene;

methyl [5(R),6(S),7(S)]-6-(4-fluorophenyl)-3-(3-methoxy-6-(2-trifluoromethyl-imidazol-1-yl)-pyridin-2-yl)-1-oxa-spiro[4.4]non-3-ene-7-carboxylate;

methyl [5(R),6(S),7(S)]-6-(4-fluorophenyl)-3-[3-methoxy-6-(2-trifluoromethyl-imidazol-1-yl)-pyridin-2-yl]-1-oxa-spiro[4.4]non-2-ene-7-carboxylate;

methyl [3(S),5(R),6(S),7(S)]-6-(4-fluorophenyl)-3-[3-methoxy-6-(2-trifluoromethylimidazol-1-yl)-pyridin-2-yl]-1-oxa-spiro[4.4]nonane-7-carboxylate;

[5(R),6(S),7(S)]-6-(4-fluorophenyl)-3-[3-methoxy-6-(2-trifluoromethyl-imidazol-1-yl)pyridin-2-yl]-1-oxa-spiro[4.4]non-3-en-7-methanol;

[5(R),6(S),7(S)]-6-(4-fluorophenyl)-3-[3-methoxy-6-(2-trifluoromethyl imidazol-1-yl)-pyridin-2-yl]-1-oxa-spiro[4.4]non-3-en-7-amine;

[5(R),6(S),7(S)]-6-(4-fluorophenyl)-3-[3-methoxy-6-(2-trifluoromethyl imidazol-1-yl)-pyridin-2-yl]-1-oxa-spiro [4.4]non-3-en-7-methylamine;

[3(S),5(R),6(S),7(S)]-6-(4-fluorophenyl)-3-[3-methoxy-6-(2-trifluoromethylimidazol-1-yl)-pyridin-2-yl]-1-oxa-spiro[4.4]non-7-yl-methylamine;

[3(S),5(R),6(S),7(S)]-6-(4-fluorophenyl)-3-[3-methoxy-6-(2-trifluoromethyl-imidazol-1-yl)-pyridin-2-yl ]-1-oxa-spiro[4.4]non-7-yl-methanol;

[3(S),5(R),6(S),7(S)]-6-(4-fluorophenyl)-3-[3-methoxy-6-(2-trifluoromethyl-imidazol-1-yl)-pyridin-2-yl]-1-oxa-spiro[4.4]non-7-ylmethyl-dimethyl-amine;

methyl [5(R),6(S),7(S)]-6-(4-fluoro-phenyl)-3-[3-hydroxy-6-(2-trifluoromethyl-imidazol-1-yl)-pyridin-2-yl]-1-oxa-spiro[4.4]non-3-ene-7-carboxylate;

methyl [5(R),6(S),7(S)]-3-[3-difluoromethoxy-6-(2-trifluoromethyl-imidazol-1-yl)-pyridin-2-yl]-6(4-fluorophenyl)-1-oxa-spiro[4.4]non-3-ene-7-carboxylate;

[3(R),5(R),6(S),7(S)]-6-(4-fluorophenyl)-3-[3-methoxy-6-(2-trifluoromethyl-imidazol-1-yl)-pyridin-2-yl]-1-oxa-spiro[4.4]non-7-yl}-methanol;

methyl [5(R),6(S),7(S)]-6-(4-fluoro-phenyl)-3-[3-isopropoxy-6-(2-trifluoromethyl-imidazol-1-yl)-pyridin-2-yl]-1-oxa-spiro[4.4]non-3-ene-7-carboxylate;

methyl [5(R),6(S),7(S)]-6-(4-fluorophenyl)-3-[3-isopropoxy-6-(2-trifluoromethyl-imidazol-1-yl)-pyridin-2-yl]-1-oxa-spiro[4.4]non-2-ene-7-carboxylate;

methyl [3(S),5(R),6(S),7(S)]-6-(4-fluorophenyl)-3-[3-isopropoxy-6-(2-trifluoromethylimidazol-1-yl)-pyridin-2-yl]-1-oxa-spiro[4.4]nonane-7-carboxylate;

[3(S),5(R),6(S),7(S)]-6-(4-fluorophenyl)-3-[3-isopropoxy-6-(2-trifluoromethyl-imidazol-1-yl)-pyridin-2-yl]-1-oxa-spiro[4.4]non-7-ylmethyl-dimethylamine;

methyl[5(R),6(S),7(S)]-6-(4-fluorophenyl)-3-[2-isopropoxy-5-(5-trifluoromethyl-tetrazol-1-yl)-pyridin-3-yl]-1-oxa-spiro[4.4]non-3-ene-7-carboxylate;

methyl[3(S),5(R),6(S),7(S)]-6-(4-fluorophenyl)-3-[2-isopropoxy-5-(5-trifluoromethyl-tetrazol-1-yl)-pyridin-3-yl]-1-oxa-spiro[4.4]nonane-7-carboxylate;

[3(S),5(R),6(S),7(S)]-6-(4-fluorophenyl)-3-[2-isopropoxy-5-(5-trifluoromethyl-tetrazol-1-yl)-pyridin-3-yl]-1-oxa-spiro[4.4]non-7-yl}-methanol;

[5(R),6(S),7(S)]-(2-fluoro-1,1-dimethyl-ethyl)-[6-(4-fluoro-phenyl)-3-[2-isopropoxy-5-(5-trifluoromethyl-tetrazol-1-yl)-pyridin-3-yl]-1-oxa-spiro[4.4]non-3-en-7-yl-methyl]-amine;

[5(R),6(S),7(S)](2-fluoro-1,1-dimethyl-ethyl)-[6-(4-fluoro-phenyl)-3-[2-isopropoxy-5-(5-trifluoromethyl-tetrazol-1-yl)-pyridin-3-yl]-1-oxa-spiro [4.4]non-2-en-7-ylmethyl]-amine;

[3(S),5(R),6(S),7(S)](2-fluoro-1,1-dimethyl-ethyl)-{6-(4-fluoro-phenyl)-3-[2-isopropoxy-5-(5-trifluoromethyl-tetrazol-1-yl)-pyridin-3-yl]-1-oxa-spiro[4.4]non-7-ylmethyl }-amine;

[5(R),6(S),7(S)-(2-fluoroethyl)-[6-(4-fluoro-phenyl)-3-[2-isopropoxy-5-(5-trifluoromethyl-tetrazol-1-yl)-pyridin-3-yl]-1-oxa-spiro[4.4]non-3-en-7-ylmethyl]-amine;

[3(S),5(R),6(S),7(S)](2-fluoro-ethyl)-{6-(4-fluoro-phenyl)-3-[2-isopropoxy-5-(5-trifluoromethyl-tetrazol-1-yl)-pyridin-3-yl]-1-oxa-spiro[4.4]non-7-ylmethyl}-amine;

[5(R),6(S),7(S)]-(2-fluoro-1,1-dimethyl-ethyl)-[6-(4-fluoro-phenyl)-3-(2-isopropoxy-5-trifluoromethylpyridin-3-yl)-1-oxa-spiro[4.4]non-3-en-7-yl-methyl]-amine;

[3(S),5(R),6(S),7(S)](2-fluoro-1,1-dimethyl-ethyl)-[6-(4-fluorophenyl)-3-(2-isopropoxy-5-trifluoromethylpyridin-3-yl)-1-oxa-spiro[4.4]non-7-ylmethyl]-amine;

(5R,6S,7S)-6-(4-fluorophenyl)-3-(2-methoxy-5-(2-(trifluoromethyl)imidazol-1-yl)phenyl)-1-oxaspiro[4.4]non-3-ene-7-carboxylic acid methyl ester;

(3S,5R,6S,7S)-6-(4-fluorophenyl)-3-[2-methyl-6-(5-trifluoromethyl-tetrazol-1-yl)-benzooxazol-4-yl]-1-oxa-spiro[4.4]non-3-ene-7-carboxylic acid methyl ester;

(3S,5R,6S,7S)-6-(4-fluorophenyl)-3-[2-methyl-6-(5-trifluromethyl-tetrazol-1-yl)-benzooxazol-4-yl]-1-oxa-spiro[4.4]nonane-7-carboxylic acid methyl ester;

(3S,5R,6S,7S)-6-(4-fluorophenyl)-3-(2-methyl-5-trifluoromethyl-benzooxazol-7-yl)-1-oxa-spiro[4.4]non-3-ene-7-carboxylic acid methyl ester;

(3S,5R,6S,7S)-6-(4-fluorophenyl)-3-(2-methyl-5-trifluoromethyl-benzooxazol-7-yl)-1-oxa-spiro[4.4]nonane-7-carboxylic acid methyl ester;

(3S,5R,6S,7S)-6-(4-fluorophenyl)-3-[2-methyl-5-(5-trifluromethyl-tetrazol-1-yl)-benzooxazol-7-yl]-1-oxa-spiro[4.4]non-3-ene-7-carboxylic acid methyl ester;

(3S,5R,6S,7S)-6-(4-fluorophenyl)-3-[2-methyl-5-(5-trifluromethyl-tetrazol-1-yl)-benzooxazol-7-yl]-1-oxa-spiro[4.4]non-2-ene-7-carboxylic acid methyl ester;

(3S,5R,6S,7S)-6-(4-fluorophenyl)-3-[2-methyl-5-(5-trifluromethyl-tetrazol-1-yl)-benzooxazol-7-yl]-1-oxa-spiro[4.4]nonane-7-carboxylic acid methyl ester;

and pharmaceutically acceptable salts and individual diasteromers thereof.

Throughout the instant application, the following abbreviations are used with the following meanings:

Reagents:

| | |
|---|---|
| Cbz-Cl | benzyl chloroformate |
| BOP | benzotriazol-1-yloxy tris(dimethylamino)-phosphonium hexafluorophosphate |
| CDI | 1,1'-carbonyldiimidazole |
| ACE-Cl | alpha-chloroethyl chloroformate |
| MCPBA | m-chloroperbenzoic acid |
| DBU | 1,8-diazabicyclo[5.4.0]undec-7-ene |
| DCC | N,N'-dicyclohexylcarbodiimide |
| DCU | N,N'-dicyclohexylurea |
| DIBAL | diisobutylaluminum hydride |
| iPr$_2$NEt or DIPEA | N,N-diisopropylethylamine |
| EDC | 1-(3-dimethylaminopropyl)-3-ethylcarbodiimide hydrochloride |
| DMAP | 4-dimethylaminopyridine |
| Me$_2$SO$_4$ | dimethyl sulfate |
| EDAC | 1-ethyl-3-(3-dimethylaminopropyl)carbodiimide hydrochloride |
| HOBt | 1-hydroxybenzotriazole hydrate |
| NHS | N-hydroxysuccinimide |
| LAH | lithium aluminum hydride |
| LHMDS | lithium bis(trimethylsilyl)amide |
| NMM | N-methylmorpholine |
| KHMDS | potassium bis(trimethylsilyl)amide |
| NaOEt | sodium ethoxide |
| Et$_3$N | triethylamine |
| Ph$_3$P | triphenylphosphine |
| TFA | trifluoroacetic acid |
| DEAD | diethyl azodicarboxylate |

Solvents:

| | |
|---|---|
| AcOH | acetic acid |
| MeCN | acetonitrile |
| AmOH | n-amyl alcohol |
| DMSO | dimethylsulfoxide |
| DMF | N,N-dimethylformamide |
| EtOH | ethanol |
| EtOAc | ethyl acetate |
| MeOH | methanol |
| THF | tetrahydrofuran |

Others:

| | |
|---|---|
| Am | n-amyl |
| Ar | aryl |
| BOC | tert-butoxycarbonyl |
| Bn | benzyl |
| Bu | butyl |
| Cbz | carbobenzyloxy (benzyloxycarbonyl) |
| calc. | calculated |
| cat. | catalytic |
| EI-MS | electron ion-mass spectroscopy |
| Et | ethyl |
| eq. | equivalent(s) |
| FAB-MS | fast atom bombardment mass spectrometry |
| HPLC | high pressure liquid chromatography |
| iPr | isopropyl |
| MPLC | medium pressure liquid chromatography |
| Me | methyl |
| MHz | megahertz |
| MF | molecular formula |
| NMR | nuclear magnetic resonance |
| Ph | phenyl |
| PTC | phase transfer catalyst |
| prep. | prepared or preparative |
| Pr | propyl |
| rt | room temperature |
| TLC | thin layer chromatography |
| TMS | tetramethylsilane |

The preparation of compounds of Formula I of the present invention may be carried out in sequential or convergent synthetic routes. Syntheses detailing the preparation of the compounds of Formula I in a sequential manner are presented in the following reaction schemes. The skills required in carrying out the reaction and purification of the resulting reaction products are known to those in the art. Purification procedures includes crystallization, normal phase or reverse phase chromatography.

Several methods for preparing the compounds of this invention are illustrated in the following Schemes and Examples wherein A, $R^3$, $R^4$, $R^5$, $R^6$, $R^7$, $R^8$, $R^9$, $R^{10}$, $R^{11}$, $R^{12}$ and $R^{13}$ are as defined above (or as defined herein).

SCHEME 1

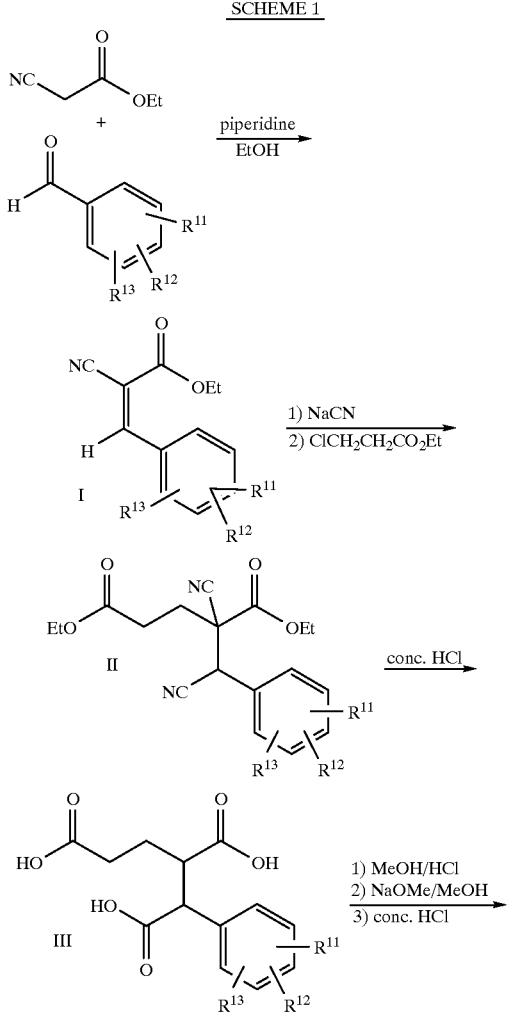

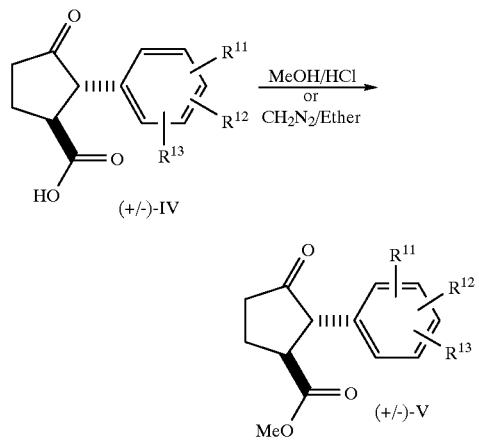

Intermediates for preparation of the compounds of the present invention in which the central ring is 5-membered may be synthesized by the general route outlined in Scheme 1. Thus, according to the procedure of Baker and Leeds (*J. Chem. Soc* 1948, 974), condensation of ethyl cyanoacetate and benzaldehyde (with or without substituents) in the presence of a base such as piperidine provides the unsaturated derivative I. Exposure of this olefin to sodium cyanide followed by ethyl 3-chloropropionate gives the dicyano derivative II, which after aqueous acidic hydrolysis yields triacid III. After esterification with acidic methanol, the triester can be cyclized by heating with sodium methoxide in dry methanol followed by treatment with aqueous HCl, to provide racemic cyclopentanone IV. The methyl ester V can be formed from ketone IV by treatment with acidic methanol or diazomethane in ether.

SCHEME 2

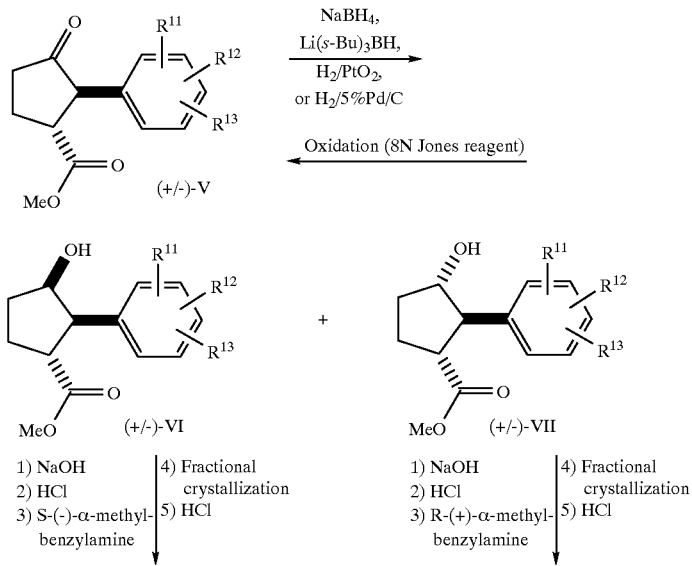

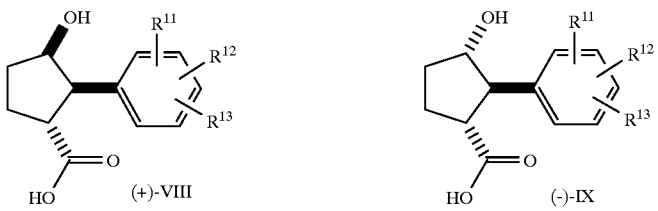

The reduction of ketone V may be accomplished with various reducing agents, for example, sodium borohydride, lithium tri(sec-butyl)-borohydride and the like, or with hydrogen in the presence of a suitable catalyst, such as platinum oxide or 5% palladium on carbon, which provide the corresponding cis- and trans- alcohols VI and VII, respectively (Scheme 2). The ratio of VI to VII thus obtained is dependent on the reducing agent employed. Alcohols VI and VII may be interconverted by oxidation to ketone V with chromium trioxide, pyridinium chlorochromate, DMSO/oxalyl chloride/triethylamine or similar agents followed by reduction with one of the reagents given above. Separation of the enantiomers of esters VI and VII may be carried out by hydrolysis to the corresponding acids VIII and IX followed by fractional crystallization of the salts formed with R-(−)-α-or S-(+)-α-methylbenzylamine or other suitable chiral, non-racemic bases.

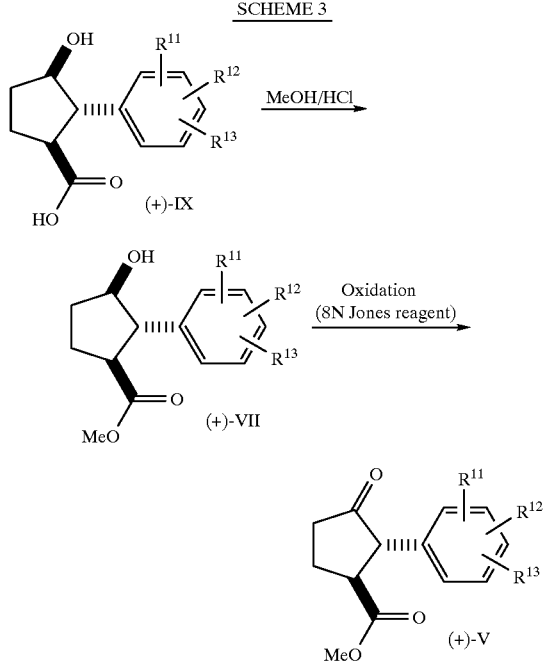

Conversion of the free acids to the keto-ester V is accomplished as shown in Scheme 3, by esterification with acidic methanol followed by oxidation with chromium trioxide, pyridinium chlorochromate, DMSO/oxalyl chloride/triethylamine or similar agents.

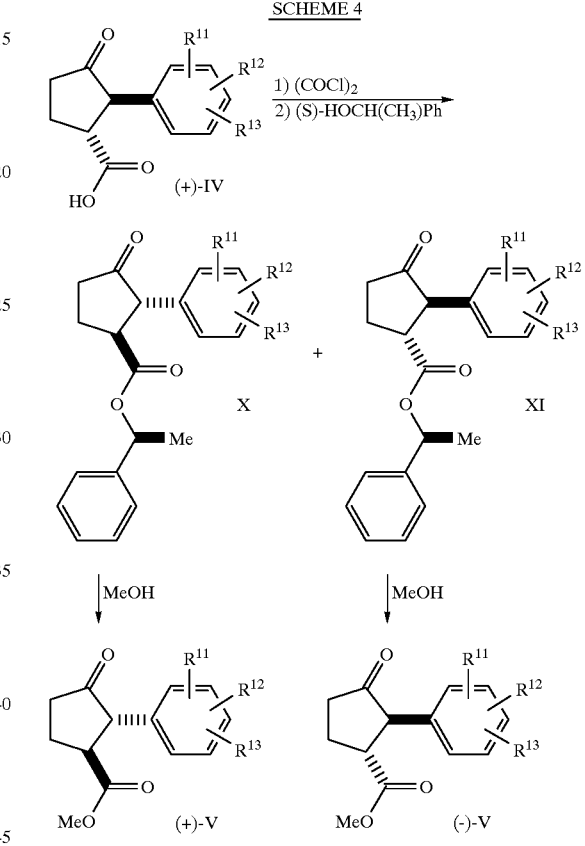

An alternative method of resolution is shown in Scheme 4. The racemic acid (+/−)-IV is activated with, for example, oxalyl chloride, DCC, EDAC/HOBt or similar condensing reagents, and then allowed to react with a chiral, non-racemic alcohol, such as (S)-alpha-methylbenzyl alcohol, to give the esters X and XI. After separating these diastereomers, they are individually transesterified with methanol to provide the separate enantiomers (+)-V and (−)-V.

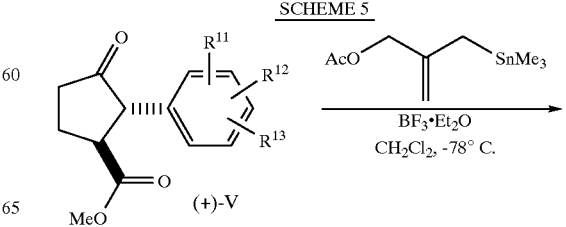

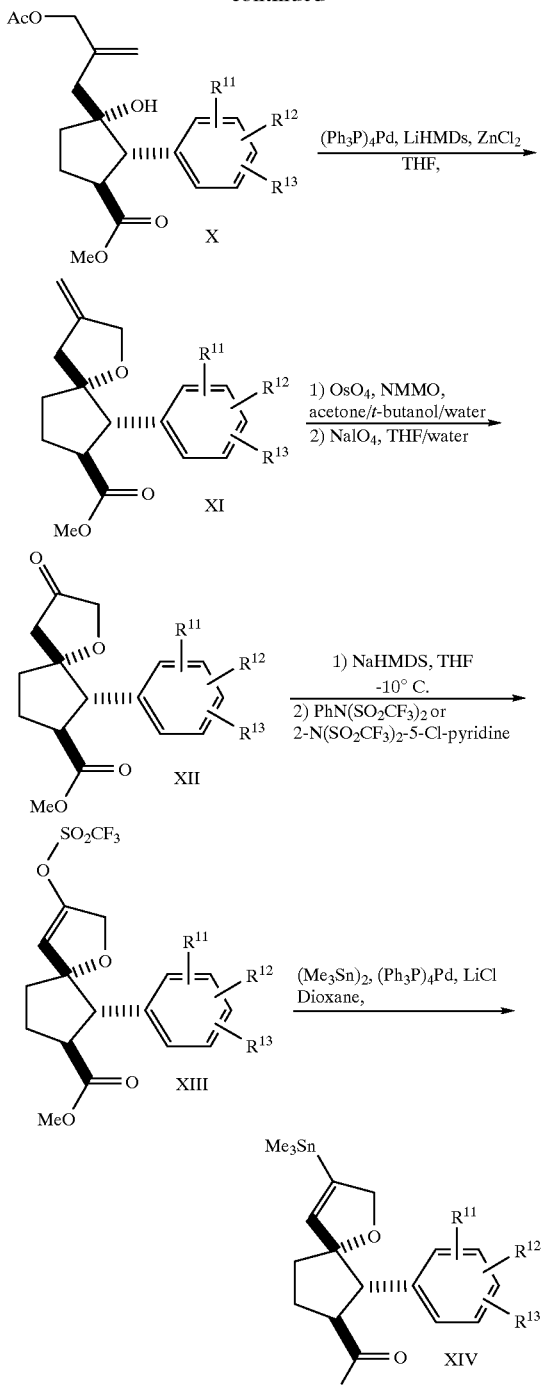

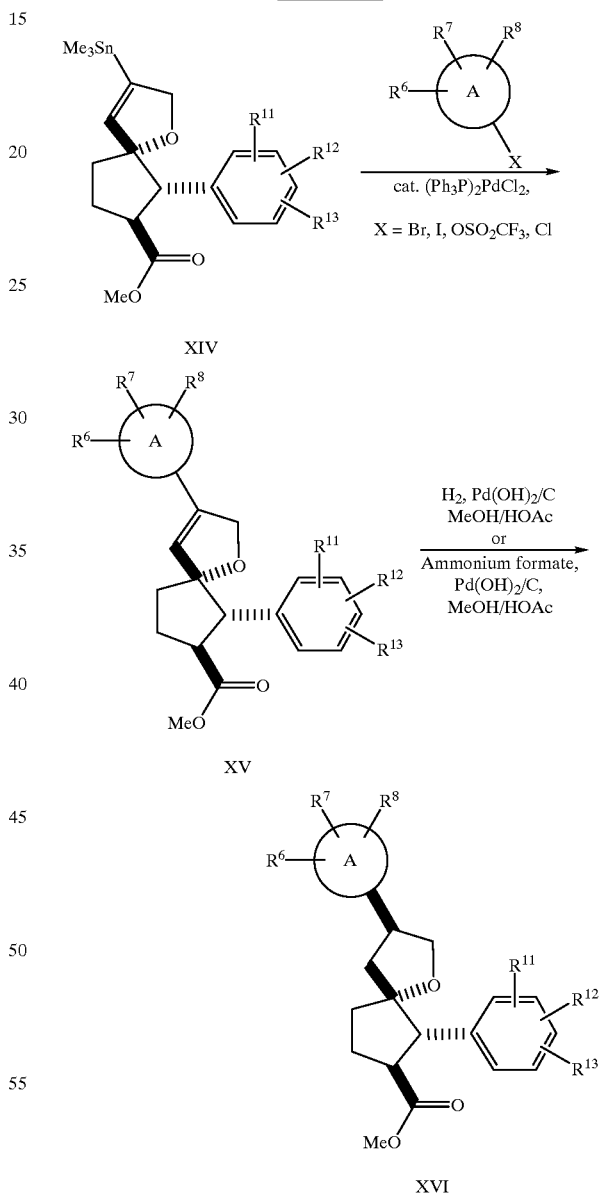

suitable strong base, such as lithium, sodium, or potassium hexamethyldisilazide, lithium diisopropylamide, lithium tetramethylpiperidide, or similar agents, followed by treatment with N-phenyl triflimide, 2-[N,N-trifluoromethylsulfonyl)-amino]-5-chloropyridine (or related agents designed to transfer a trifluoromethanesulfonyl group to an alkoxide or enolate oxygen), provided the enol triflate XIII. Formation of the corresponding vinylstannane was then carried out by exposure of triflate XIII to hexamethylditin in the presence of catalytic tetrakis(triphenylphosphine) palladium and lithium chloride, to give the desired unsaturated tin derivative XIV.

The 1-oxaspiro[4.4]non-3-ene ring system is prepared as shown in Scheme 5. The ketone V is treated with 2-(acetoxymethyl)-3-(trimethylstannyl)propene and boron trifluoride etherate at low temperature in methylene chloride to provide the desired diastereomer X and lesser amounts of the epimeric product. After separation of the diastereomers, alcohol X is cyclized by treatment with tetrakis (triphenylphosphine)palladium in the presence of LiHMDS and ZnCl$_2$, to provide the spirocycle XI. Oxidative cleavage of the exocyclic olefin with either osmium tetroxide followed by sodium periodate or with ozone at low temperature gave the ketone XII. Formation of the enolate of XII with a Formation of the 3-aryl derivative is carried out as described in Scheme 6. Treatment of stannane XIV with an appropriate aryl halide or aryl trifluoromethanesulfonate in the presence of catalytic bis(triphenylphosphine) palladium dichloride or related palladium catalysts provides the unsaturated 3-aryl spirocycle XV. Alternatively, XV may be prepared by coupling enol triflate and aryl boronic acids in the presence of one of the above described catalytic systems. Hydrogenation of the double bond under standard conditions, such as transfer hydrogenation by treatment with ammonium formate in the presence of palladium hydroxide on carbon at elevated temperature, or by exposure to hydrogen gas at or above atmospheric pressure in the presence of a precious metal catalyst (such as palladium on carbon, ruthenium on carbon, platinum on carbon, rhodium on carbon and the like) or Raney nickel catalyst, provided the saturated derivative XVI.

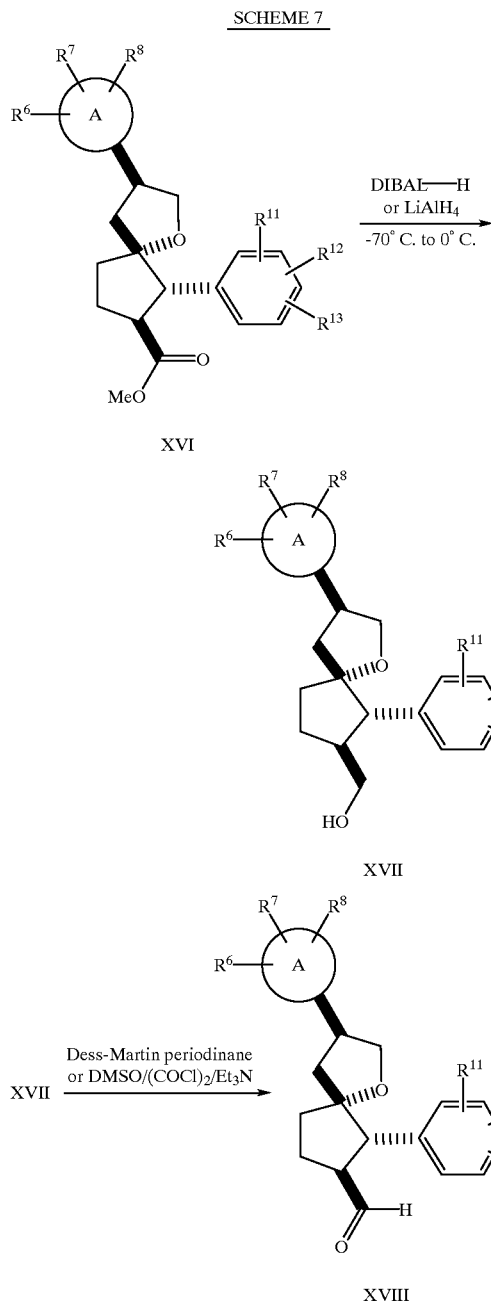

SCHEME 7

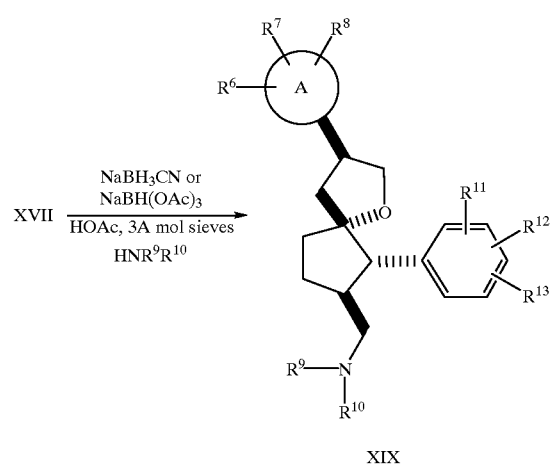

For the preparation of compounds bearing basic substituents on C7, two strategies could be used. In the first (see Scheme 7), reduction of the ester, for example with diisobutyl aluminum hydride or with lithium aluminum hydride, provides primary alcohol XVII. Oxidation of this alcohol under mild conditions, for example employing the conditions described by Swern (dimethyl sulfoxide, oxalyl chloride and triethylamine at low temperature) or by using the Dess-Martin periodinane, provides aldehyde XVIII. Reductive amination under standard conditions, for example by treatment with ammonia, a primary or secondary amine, along with sodium cyanoborohydride or sodium tris (acetoxy) borohydride in the presence of acetic acid and molecular sieves, provides the amine XIX.

SCHEME 8

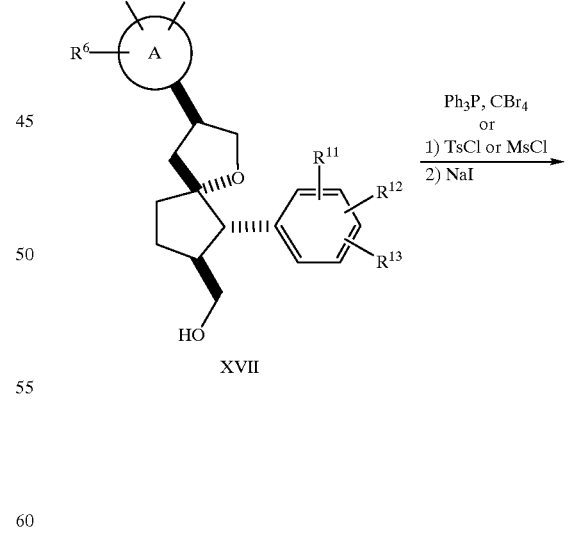

-continued

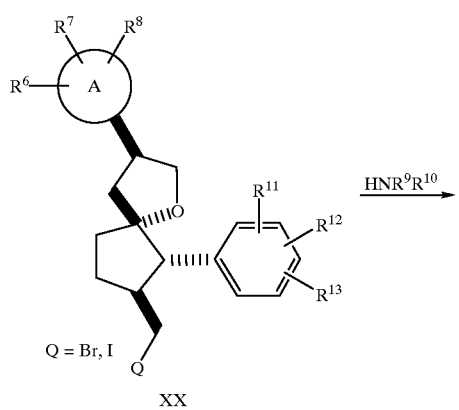

XX  Q = Br, I

HNR⁹R¹⁰ →

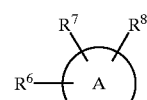

XIX

The alcohol can also be converted into a leaving group, for example by treatment with triphenylphosphine/carbon tetrabromide or by formation of the corresponding tosylate or mesylate, followed by displacement with sodium iodide, to give either the bromide or iodide XX (Scheme 8). Treatment with an appropriate amine would then provide compound XIX.

SCHEME 9

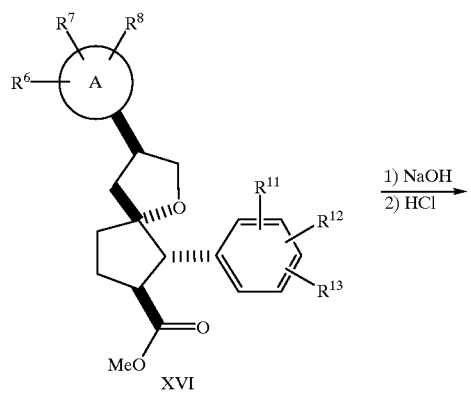

XVI

1) NaOH
2) HCl →

-continued

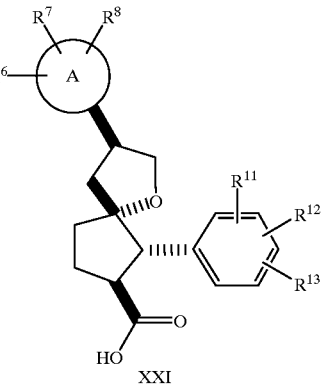

XXI 1) (COCl)₂ or SOCl₂ or iBuCOCl, base
2) NaN₃, acetone, H₂O →

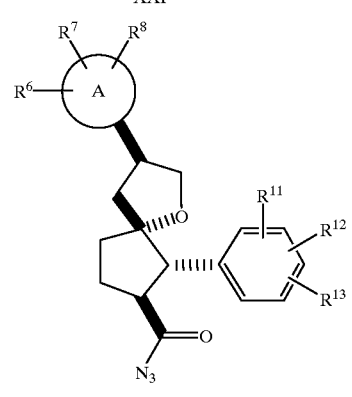

XXII benzene or toluene, →

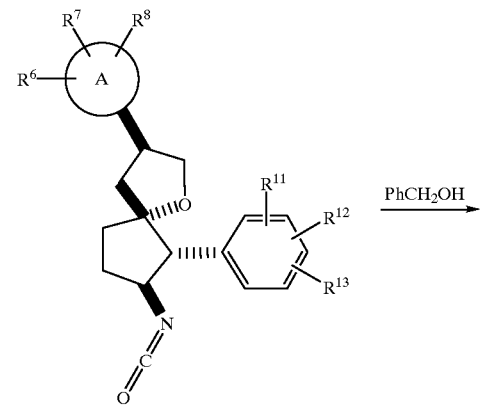

XXIII

PhCH₂OH →

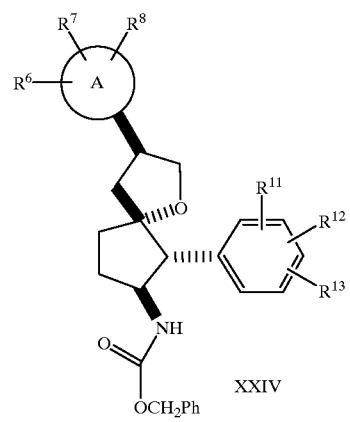

XXIV

The second strategy places the amine directly on the C7 carbon (see Scheme 9). Hydrolysis of ester XVI under standard conditions gives the corresponding acid XXI, which can be activated under a number of conditions, such as by treatment with oxalyl chloride or through mixed anhydride formation. The activated acyl derivative can then be treated with an azide salt, to provide acyl azide XXII. Thermolysis under anhydrous conditions provides the rearranged isocyanate XXIII, which can be treated with benzyl alcohol to give the CBZ protected amine XXV. Alternatively, acid XXI may be treated with $Ph_2P(O)N_3$ (diphenyl phosphoryl azide) followed by thermolysis to directly provide isocyanate XXIII.

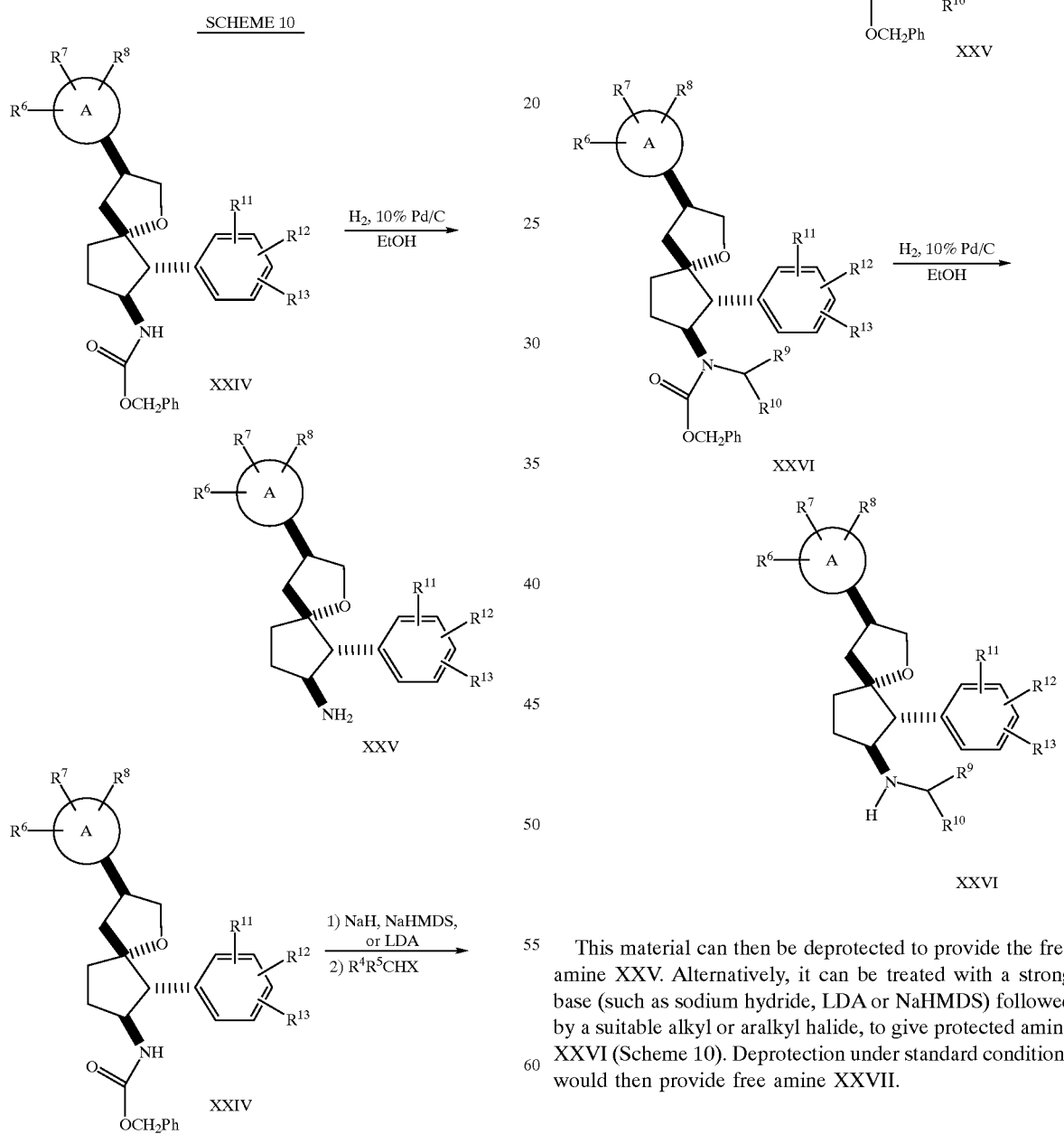

This material can then be deprotected to provide the free amine XXV. Alternatively, it can be treated with a strong base (such as sodium hydride, LDA or NaHMDS) followed by a suitable alkyl or aralkyl halide, to give protected amine XXVI (Scheme 10). Deprotection under standard conditions would then provide free amine XXVII.

SCHEME 11

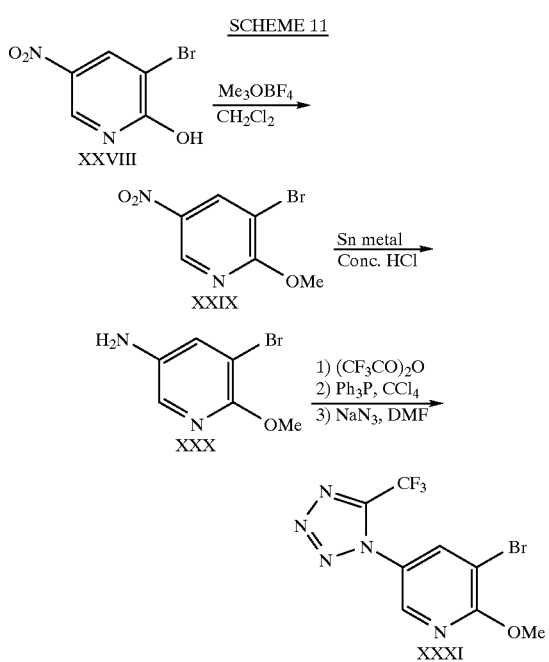

Preparation of a pyridine-containing a 5-substituent on the 1-oxaspiro[4.4]nonyl framework can be carried out according to Scheme 11. Methylation of the known bromo pyridine XXVIII with trimethyloxonium tetrafluoborate selectively provides the O-methylated product XXIX. Reduction of the nitro group with tin in concentrated HCl yields the corresponding amino pyridine XXX. Conversion of this compound to the 5-(trifluoromethyl)tetrazole XXXI can be achieved by sequential treatment with trifluoroacetic anhydride, followed by triphenylphosphine in carbon tetrachloride (to provide the imino chloride), and finally exposure to sodium azide in DMF.

SCHEME 12

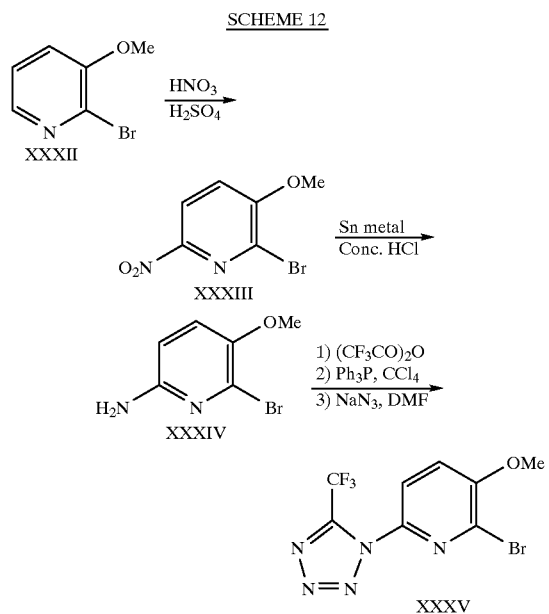

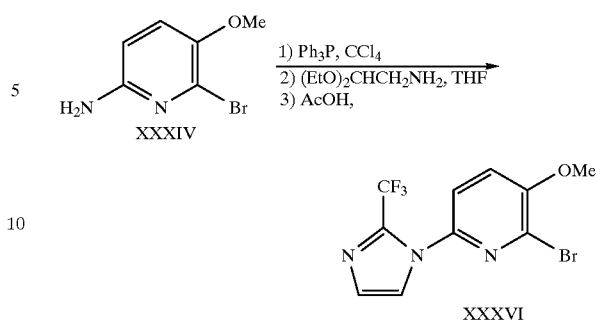

The isomeric bromide XXXV can be prepared as described in Scheme 12. Treatment of 2-bromo-3-methoxypyridine (XXXII) with warm fuming nitric acid provides 2-bromo-3-methoxy-6-nitropyridine (XXXIII). Reduction of the nitro group with tin metal in concentrated hydrochloric acid provides aminopyridine XXXIV. Conversion of this compound to the 5-(trifluoromethyl)tetrazole XXXV can be achieved by sequential treatment with trifluoroacetic anhydride, followed by triphenylphosphine in carbon tetrachloride (to provide the imino chloride), and finally exposure to sodium azide in DMF. Alternatively, the 2-(trifluoromethyl)imidazole derivative XXXVI can be prepared by treating aminopyridine XXXIV with trifluoroacetic anhydride, followed by triphenylphosphine in carbon tetrachloride and then 2-aminoacetaldehyde diethyl acetal. Deprotection, cyclization and aromatization can then be achieved by heating with acetic acid.

SCHEME 13

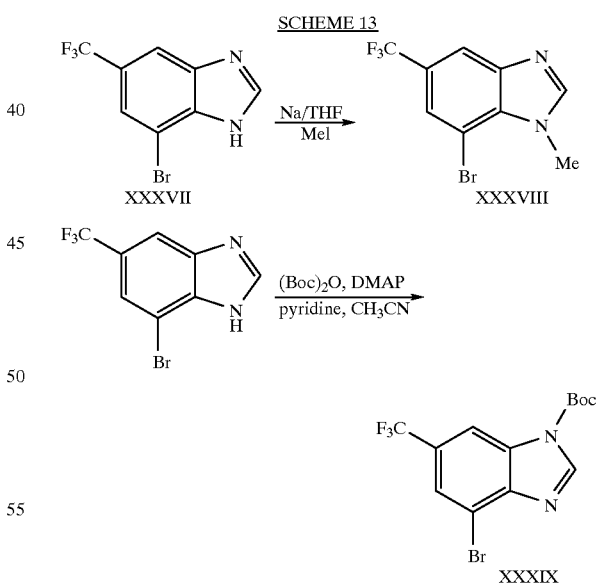

Preparation of trifluoromethyl-substituted benzimidazole derivatives can be achieved as shown in Scheme 13. Methylation of the imidazole ring of XXXVII under basic conditions, for example by treatment with sodium hydride and methyl iodide, provides the N-methyl benzimidazole XXXVIII. Alternatively, treatment of XXXVII with t-butyl carbonic anhydride produces the Boc derivative XXXIX.

SCHEME 14

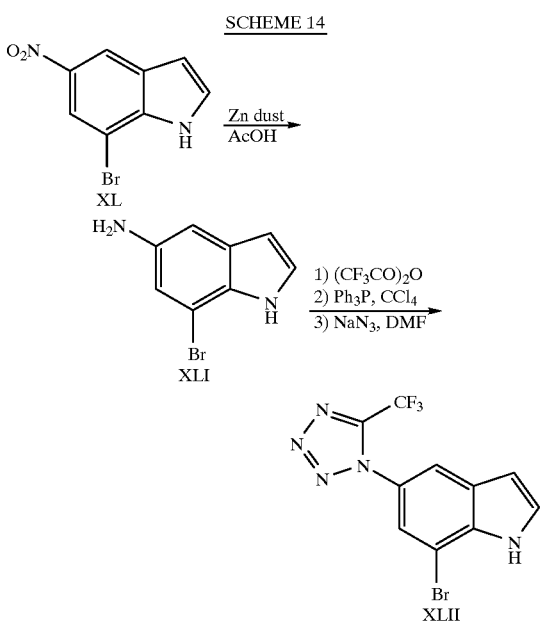

Preparation of an indole-containing 3 substituent on the 1-oxaspiro[4.4]nonyl framework can be carried out according to Scheme 14. Reduction of the nitro group in the known 7-bromo-7-nitro-1H-indole (XL) with zinc dust in glacial acetic acid provides the corresponding indole amine XLI. Conversion of this compound to the 5-(trifluoromethyl) tetrazole XLII can be achieved by sequential treatment with trifluoroacetic anhydride, followed by triphenylphosphine in carbon tetrachloride (to provide the imino chloride), and final exposure to sodium azide in DMF.

Removal of the BOC protecting group in the assembled oxaspiro nonyl structure can be carried out, for example, with zinc bromide in methylene chloride.

It is noted that in some cases the order of carrying out the foregoing reaction schemes may be varied to facilitate the synthesis or to avoid unwanted reaction products.

TACHYKININ ANTAGONISM ASSAY

The compounds of this invention are useful for antagonizing tachykinins, in particular substance P and neurokinin A in the treatment of gastrointestinal disorders, central nervous system disorders, inflammatory diseases, pain or migraine and asthma in a mammal in need of such treatment. This activity can be demonstrated by the following assays.

A. Receptor Expression in COS

To express the cloned human neurokinin-1 receptor (NK1R) transiently in COS, the cDNA for the human NK1R was cloned into the expression vector pCDM9 which was derived from pCDM8 (INVITROGEN) by inserting the ampicillin resistance gene (nucleotide 1973 to 2964 from BLUESCRIPT SK+) into the Sac II site. Transfection of 20 ug of the plasmid DNA into 10 million COS cells was achieved by electroporation in 800 ul of transfection buffer (135 mM NaCl, 1.2 mM CaCl$_2$, 1.2 mM MgCl$_2$, 2.4 mM K$_2$HPO$_4$, 0.6 mM KH$_2$PO$_4$, 10 mM glucose, 10 mM HEPES pH 7.4) at 260 V and 950 uF using the IBI GENEZAPPER (IBI, New Haven, Conn.). The cells were incubated in 10% fetal calf serum, 2 mM glutamine, 100U/ml penicillin-streptomycin, and 90% DMEM media (GIBCO, Grand Island, N.Y.) in 5% CO$_2$ at 37° C. for three days before the binding assay.

B. Stable Expression in CHO

To establish a stable cell line expressing the cloned human NK1R, the cDNA was subcloned into the vector pRcCMV (INVITROGEN). Transfection of 20 ug of the plasmid DNA into CHO cells was achieved by electroporation in 800 ul of transfection buffer suplemented with 0.625 mg/ml Herring sperm DNA at 300 V and 950 uF using the IBI GENEZAPPER (IBI). The transfected cells were incubated in CHO media [10 % fetal calf serum, 100 U/ml pennicilin-streptomycin, 2 mM glutamine, 1/500 hypoxanthine-thymidine (ATCC), 90% IMDM media (JRH BIOSCIENCES, Lenexa, Kans.), 0.7 mg/ml G418 (GIBCO)) in 5% CO$_2$ at 37° C. until colonies were visible. Each colony was separated and propagated. The cell clone with the highest number of human NK1R was selected for subsequent applications such as drug screening.

C. Assay Protocol using COS or CHO

The binding assay of human NK1R expressed in either COS or CHO cells is based on the use of $^{125}$I-substance P ($^{125}$I-Sp, from DU PONT, Boston, Mass.) as a radioactively labeled ligand which competes with unlabeled substance P or any other ligand for binding to the human NK1R. Monolayer cell cultures of COS or CHO were dissociated by the non-enzymatic solution (SPECIALTY MEDIA, Lavallette, N.J.) and resuspended in appropriate volume of the binding buffer (50 mM Tris pH 7.5, 5 mM MnCl$_2$, 150 mM NaCl, 0.04 mg/ml bacitracin, 0.004 mg/ml leupeptin, 0.2 mg/ml BSA, 0.01 mM phosphoramidon) such that 200 ul of the cell suspension would give rise to about 10,000 cpm of specific $^{125}$I-SP binding (approximately 50,000 to 200,000 cells). In the binding assay, 200 ul of cells were added to a tube containing 20 ul of 1.5 to 2.5 nM of $^{125}$I-SP and 20 ul of unlabeled substance P or any other test compound. The tubes were incubated at 4° C. or at room temperature for 1 hour with gentle shaking. The bound radioactivity was separated from unbound radioactivity by GF/C filter (BRANDEL, Gaithersburg, Md.) which was pre-wetted with 0.1 % polyethylenimine. The filter was washed with 3 ml of wash buffer (50 mM Tris pH 7.5, 5 mM MnCl$_2$, 150 mM NaCl) three times and its radioactivity was determined by gamma counter.

The activation of phospholipase C by NK1R may also be measured in CHO cells expressing the human NK1R by determining the accumulation of inositol monophosphate which is a degradation product of IP$_3$. CHO cells are seeded in 12-well plate at 250,000 cells per well. After incubating in CHO media for 4 days, cells are loaded with 0.025 uCi/ml of $^3$H-myoinositol by overnight incubation. The extracellular radioactivity is removed by washing with phosphate buffered saline. LiCl is adied to the well at final concentration of 0.1 mM with or without the test compound, and incubation is continued at 37° C. for 15 min. Substance P is added to the well at final concentration of 0.3 nM to activate the human NK1R. After 30 min of incubation at 37° C., the media is removed and 0.1N HCl is added. Each well is sonicated at 4° C. and extracted with CHCl$_3$/methanol (1:1). The aqueous phase is applied to a 1 ml Dowex AG 1X8 ion exchange column. The column is washed with 0.1N formic acid followed by 0.025M ammonium formate-0.1N formic acid. The inositol monophosphate is eluted with 0.2M ammonium formate-0.1N formic acid and quantitated by beta counter.

In particular, the intrinsic tachykinin receptor antagonist activities of the compounds of the present invention may be shown by this assay. The compounds of the following examples have activity in the aforementioned assay in the range of 0.05 nM to 10 μM. The activity of the present compounds may also be demonstrated by the assay disclosed by Lei, et al., *British J. Pharmacol.*, 105, 261–262 (1992).

The compounds of the present invention are useful in the prevention and treatment of a wide variety of clinical conditions which are characterized by the presence of an excess of tachykinin, in particular substance P, activity. These conditions may include disorders of the central nervous system such as anxiety, depression, psychosis and schizophrenia; epilepsy; neurodegenerative disorders such as dementia, including senile dementia of the Alzheimer type, Alzheimer's disease and Down's syndrome; demyelinating diseases such as multiple sclerosis (MS) and amyotrophic lateral sclerosis (ALS; Lou Gehrig's disease) and other neuropathological disorders such as peripheral neuropathy, for example AIDS related neuropathy, diabetic neuropathy, chemotherapy-induced neuropathy, and postherpetic and other neuralgias; small cell carcinomas such as small cell lung cancer; respiratory diseases, particularly those associated with excess mucus secretion, such as chronic obstructive airways disease, bronchopneumonia, chronic bronchitis, acute bronchitis, diffuse panbronchilitis, emphysema, cystic fibrosis, asthma, and bronchospasm; airways disease modulated by neurogenic inflammation; laryngopharhngitis; bronchiectasis; conoisis; whooping cough; pulmonary tuberculosis; diseases associated with decreased glandular secretions, including lacrimation, such as Sjogren's syndrome, hyperlipoproteinemias IV and V, hemochromatosis, sarcoidosis, or amyloidosis; iritis; inflammatory diseases such as inflammatory bowel disease, inflammatory intestinal disease, psoriasis, fibrositis, ocular inflammation, osteoarthritis, rheumatoid arthritis, pruritis, and sunburn; hepatitis; allergies such as eczema and rhinitis; hypersensitivity disorders such as poison ivy; ophthalmic diseases such as conjunctivitis, vernal conjunctivitis, dry eye syndrome, and the like; ophthalmic conditions associated with cell proliferation such as proliferative vitreoretinopathy; cutaneous diseases such as contact dermatitis, atopic dermatitis, urticaria, and other eczematoid dermatitis; hemodialysis-associated itching; lichen planus; oedema, such as oedema caused by thermal injury; addiction disorders such as alcoholism; mental disease, particularly anxiety and depression; stress related somatic disorders; reflex sympathetic dystrophy such as shoulder/hand syndrome; dysthymic disorders; tenalgia attended to hyperlipidemia; post-operative neuroma, particularly of mastectomy; vulvar vestibulitis; amniogenesis; adverse immunological reactions such as rejection of transplanted tissues and disorders related to immune enhancement or suppression, such as systemic lupus erytlmatosus; gastrointestinal (GI) disorders, including inflammatory disorders, and diseases of the GI tract, such as gastritis, gastroduodenal ulcers, gastric carcinomas, gastric lymphomas, disorders associated with the neuronal control of viscera such as ulcerative colitis, Crohn's disease, irritable bowel syndrome, nausea, and emesis, including acute, delayed, post-operative, late-phase, and anticipatory emesis, such as emesis or nausea induced by for example chemotherapy, radiation, surgery, migraine, toxins, such as metabolic or microbial toxins, viral or bacterial infections, pregnancy, vestibular disorder, motion, mechanical stimulation, gastrointestinal obstruction, reduced gastrointestinal motility, visceral pain, psychological stress or disturbance, high altitude, weightlessness, opioid analgesics, intoxication, resulting for example from consumption of alcohol, and variations in intercranial pressure, in particular, for example, drug or radiation induced emesis or post-operative nausea and vomiting; disorders of bladder function such as cystitis, bladder detrusor hyperreflexia, and incontinence; fibrosing and collagen diseases such as scleroderma and eosinophilic fascioliasis; disorders of blood flow caused by vasodilation and vasospastic diseases such as angina, migraine and Reynaud's disease; sleep disorders and sleep disturbances including: sleep problems associated with insomnia, hypersomnia, sleep apnea, narcolepsy, nocturnal myoclonus, REM sleep interruptions, jet-lag, shift workers' sleep disturbances, dysomnias, night terror, insomnias associated with depression or with emotionailmood disorders, as well as sleep walking and enuresis, as well as sleep disorders which accompany aging, conditions associated with circadian rhythmicity, mental and physical disorders associated with travel across time zones and with rotating shift-work schedules, or syndromes such as fibromyalgia which are manifested by non-restorative sleep and muscle pain or sleep apnea which is associated with respiratory disturbances during sleep; altering circadian rhythms; enhancing and improving the quality of sleep; and pain or nociception, for example, chronic pain or that attributable to or associated with any of the foregoing conditions especially the transmission of pain in migraine, or such as headache, toothache, cancerous pain, back pain, post-operative pain, neuritic pain symptoms, fibromyalgia and superficial pain on congelation, burn, herpes zoster or diabetic neuropathy. Hence, these compounds may be readily adapted to therapeutic use for the treatment of physiological disorders associated with an excessive stimulation of tachykinin receptors, especially neurokinin-1, and as neurokinin-1 antagonists in the control and/or treatment of any of the aforesaid clinical conditions in mammals, including humans.

The compounds of the present invention are also of value in the treatment of a combination of the above conditions, in particular in the treatment of combined post-operative pain and post-operative nausea and vomiting. The compounds of the present invention are particularly useful in the treatment of nausea or emesis, including acute, delayed, post-operative, late-phase, and anticipatory emesis, such as emesis or nausea induced by for example chemotherapy, radiation, surgery, migraine, toxins, such as metabolic or microbial toxins, viral or bacterial infections, pregnancy, vestibular disorder, motion, mechanical stimulation, gastrointestinal obstruction, reduced gastrointestinal motility, visceral pain, psychological stress or disturbance, high altitude, weightlessness, opioid analgesics, intoxication, resulting for example from consumption of alcohol, and variations in intercranial pressure. Most especially, the compounds are of use in the treatment of emesis induced by antineoplastic (cytotoxic) agents including those routinely used in cancer chemotherapy.

Examples of such chemotherapeutic agents include alkylating agents, for example, nitrogen mustards, ethyleneimine compounds, alkyl sulfonates and other compounds with an alkylating action such as nitrosoureas, cisplatin, and dacarbazine; antimetabolites, for example, folic acid, purine or pyrimidine antagonists; mitotic inhibitors, for example, vinca alkaloids and derivatives of podophyllotoxin; and cytotoxic antibiotics.

Particular examples of chemotherapeutic agents are described, for example, by D. J. Stewart in "Nausea and Vomiting: Recent Research and Clinical Advances", Eds. J. Kucharczyk, et al., CRC Press Inc., Boca Raton, Fla., USA (1991), pages 177–203, especially page 188. Commonly used chemotherapeutic agents include cisplatin, dacarbazine (DTIC), dactinomycin, mechlorethamine (nitrogen mustard), streptozocin, cyclophosphamide, carmustine (BCNU), lomustine (CCNU), doxorubicin (adriamycin), daunorubicin, procarbazine, mitomycin, cytarabine, etoposide, methotrexate, 5-fluorouracil, vinblastine, vincristine, bleomycin, and chlorambucil [R. J. Gralla, et al., *Cancer Treatment Reports*, 68(1), 163–172 (1984)].

The compounds of the present invention are also of use in the treatment of emesis induced by radiation including radiation therapy such as in the treatment of cancer, or radiation sickness, and in the treatment of post-operative nausea and vomiting.

The compounds of the present invention are also of use in the prevention or treatment of disorders of the central nervous system such as anxiety, psychosis and schizophrenia; neurodegenerative disorders such as senile dementia of the Alzheimer type, Alzheimer's disease and Down's syndrome; respiratory diseases, particularly those associated with excess mucus secretion, such as chronic obstructive airways disease, broncho-pneumonia, chronic bronchitis, cystic fibrosis and asthma, and bronchospasm; inflammatory diseases such as inflammatory bowel disease, osteoarthritis, rheumatoid artritis and fibromyalgia; adverse immunological reactions such as rejection of transplanted tissues; gastrointestinal (GI) disorders and diseases of the GI tract such as disorders associated with the neuronal control of viscera such as ulcerative colitis, Crohn's disease and incontinence; disorders of blood flow caused by vasodilation; and pain or nociception, for example, that attributable to or associated with any of the foregoing conditions or the transmission of pain in migraine (both prophylaxis and acute treatment).

The compounds of the present invention are also particularly useful in the treatment of pain or nociception and/or inflammation and disorders associated therewith such as, for example: neuropathy, such as diabetic or peripheral neuropathy and chemotherapy-induced neuropathy; postherpetic and other neuralgias; inflammatory bowel disease; acute and chronic pain, such as post-operative pain, cancer-related pain, neuritic pain syndromes, and fibromyalgia; asthma; osteoarthritis; rheumatoid arthritis; psoriasis; and especially migraine, either alone or in combination or co-administration with other antiinflammatory or analgesic agents.

The compounds of the present invention are also particularly useful in the treatment of diseases characterized by neurogenic mucus secretion, especially cystic fibrosis.

In the treatment of the clinical conditions noted above, the compounds of this invention may be utilized in compositions such as tablets, capsules or elixirs for oral administration, suppositories for rectal administration, sterile solutions or suspensions for parenteral or intramuscular administration, and the like.

The pharmaceutical compositions of this invention may be used in the form of a pharmaceutical preparation, for example, in solid, semisolid or liquid form, which contains one or more of the compounds of the present invention, as an active ingredient, in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, or liquid form, and in addition auxiliary, stabilizing, thickening and coloring agents and perfumes may be used. The active object compound is included in the pharmaceutical composition in an amount sufficient to produce the desired effect upon the process or condition of the disease.

The present invention is further directed to a method for the manufacture of a medicament for antagonizing the effect of substance P or another tachykinin at its receptor site or for the blockade of neurokinin-1 receptors or other tachykin receptors in a mammal comprising combining a compound of the present invention with a pharmaceutical carrier or diluent.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solution, suitably flavoured syrups, aqueous or oil suspensions, and emulsions with acceptable oils such as cottonseed oil, sesame oil, coconut oil or peanut oil, or with a solubilizing or emulsifying agent suitable for intravenous use, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are administered by the oral or nasal respiratory route for local or systemic effect. Compositions in preferably sterile pharmaceutically acceptable solvents may be nebulized by use of inert gases. Nebulized solutions may be breathed directly from the nebulizing device or the nebulizing device may be attached to a face mask, tent or intermittent positive pressure breathing machine. Solution, suspension or powder compositions may be administered, preferably orally or nasally, from devices which deliver the formulation in an appropriate manner.

For the treatment of the clinical conditions and diseases noted above, the compounds of this invention may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques.

For the treatment of certain conditions it may be desirable to employ a compound of the present invention in conjunction with another pharmacologically active agent(s). A compound of the present invention and the other pharmacologically active agent(s) may be administered to a patient simultaneously, sequentially or in combination. For example, the present compound may employed directly in combination with the other active agent(s), or it may be administered prior, concurrent or subsequent to the administration of the other active agent(s). In general, the currently available dosage forms of the known therapeutic agents for use in such combinations will be suitable.

For example, a compound of the present invention may be presented together with another therapeutic agent as a combined preparation for simultaneous, separate, or sequential use for the relief of emesis. Such combined preparations may be, for example, in the form of a twin pack. A preferred combination comprises a compound of the present invention with a chemotherapeutic agent such as an alkylating agent, antimetabolite, mitotic inhibitor, or cytotoxic antibiotic, as described above.

Similarly, for the treatment or prevention of pain or inflammatory diseases, the present compounds may be used in conjunction with an antiinflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal antiinflammatory agent, or a cytokine-suppressing antiinflammatory agent, for example with a compound such as acetaminophen, asprin, codiene, fentanyl, ibuprofen, indomethacin, ketorolac, morphine, naproxen, phenacetin, piroxicam, a steroidal analgesic, sufentanyl, sunlindac, tenidap, and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levo-desoxy-ephedrine; an antiitussive such as codeine, hydrocodone, caramiphen, carbetapentane, or dextramethorphan; a diuretic; and a sedating or non-sedating antihistamine.

Also, for the treatment of respiratory diseases, such as asthma, a compound of the present invention may be used in conjunction with a bronchodilator, such as a β2-adrenergic receptor agonist or a tachykinin antagonist which acts at neurokinin-2 receptors. Suitable β2-adrenergic receptor agonist include: Bambuterol (U.S. Pat. No. 4,419,364 issued to Draco on Dec. 6, 1983); Bitolterol mesylate (U.S. Pat. No. 4,138,581 issued to Sterling Feb. 6, 1979); Brosaterol (U.S. Pat. No. 4,276,299 issued to Zambon Jun. 30, 1981 and U.S. Pat. No. 4,520,200 issued to Zambon May 28, 1985); Carbuterol (U.S. Pat. No. 3,763,232 issued to Smith Kline Oct. 2, 1973); Clenbuterol (U.S. Pat. No. 3,536,712 issued to Boehringer Ingelheim Oct. 27, 1970); Cimaterol (U.S. Pat. No. 4,407,819 issued to American Cyanamid Oct. 4, 1983); Docarpamine (U.S. Pat. No. 4,228,183 issued to Tanabe Oct. 14, 1980); Dopexamine (U.S. Pat. No. 4,645,768 issued to Fisons Feb. 24, 1987); Formoterol (U.S. Pat. No. 3,994,974 issued to Yamanouchi Nov. 30, 1976); Mabuterol (U.S. Pat. No. 4,119,710 issued to Boehringer Ingelheim Oct. 10, 1978); Pirbuterol hydrochloride (U.S. Pat. No. 3,700,681 issued to Pfizer Oct. 24, 1972); Procaterol hydrochloride (U.S. Pat. No. 4,026,897 issued to Otsuka May 31, 1977); Ritodrine hydrochloride (U.S. Pat. No. 3,410,944 issued to North American Philips Nov. 12, 1968); or Salmeterol (U.S. Pat. No. 4,992,474 issued to Glaxo Feb. 21, 1991 and U.S. Pat. No. 5,091,422 issued to Glaxo Feb. 25, 1992).

Also, for the treatment of conditions that require antagonism of both neurokinin-1 and neurokinin-2, including disorders associated with bronchoconstriction and/or plasma extravasation in airways, such as asthma, chronic bronchitis, airways disease, or cystic fibrosis; neuropathy, such as diabetic or peripheral neuropathy and chemotherapy-induced neuropathy; osteoarthritis; rheumatoid arthritis; and migraine, a compound of the present invention may be used in conjunction with a tachykinin antagonist which acts at neurokinin-2 receptors, or with tachykinin receptor antagonist which acts at both neurokinin-1 and neurokinin-2 receptors.

Likewise, a compound of the present invention may be employed with a leucotriene antagonist, such a leucotriene $D_4$ antagonist, exempified by those disclosed in Patent Pub. EP 0,480,717, published Apr. 15, 1992; Patent Pub. EP 0 604,114, published June 1994; U.S. Pat. No. 5,270,324, issued Dec. 14, 1993; and U.S. Pat. No. 4,859,692, issued Aug. 22, 1989. This combination is particularly useful in the treatment of respiratory diseases such as asthma, chronic bronchitis and cough.

A compound of the present invention further may be used in conjunction with a corticosteroid such as Dexamethasone, Kenalog, Aristocort, Nasalide, Preferid, Benecorten or others such as disclosed in U.S. Pat. Nos. 2,789,118, 2,990,401, 3,048,581, 3,126,375, 3,929,768, 3,996,359, 3,928,326 and 3,749,712.

Similarly, for the prevention or treatment of emesis a compound of the present invention may be used in conjunction with other anti-emetic agents, especially $5HT_3$ receptor antagonists, such as ondansetron, granisetron, tropisetron, decadron, and zatisetron, or $GABA_B$ receptor agonists, such as baclofen. Likewise, for the prevention or treatment of migraine a compound of the present invention may be used in conjunction with other anti-migraine agents, such as ergotamines or $5HT_1$ agonists, especially sumatriptan.

Likewise, for the treatment of behavioral hyperalgesia, a compound of the present invention may be used in conjunction with an antagonist of N-methyl D-aspartate (NMDA), such as dizocilpine. For the prevention or treatment of inflammatory conditions in the lower urinary tract, especially cystitis, a compound of the present invention may be used in conjunction with an antiinflammatory agent, such as a bradykinin receptor antagonist. The compound of the present invention and the other pharmacologically active agent may be administered to a patient simultaneously, sequentially or in combination.

The compounds of this invention may be administered to patients (animals and humans) in need of such treatment in dosages that will provide optimal pharmaceutical efficacy. It will be appreciated that the dose required for use in any particular application will vary from patient to patient, not only with the particular compound or composition selected, but also with the route of administration, the nature of the condition being treated, the age and condition of the patient, concurrent medication or special diets then being followed by the patient, and other factors which those skilled in the art will recognize, with the appropriate dosage ultimately being at the discretion of the attendant physician.

In the treatment of a condition associated with an excess of tachykinins, an appropriate dosage level will generally be about 0.001 to 50 mg per kg patient body weight per day which may be administered in single or multiple doses. Preferably, the dosage level will be about 0.01 to about 25 mg/kg per day; more preferably about 0.05 to about 10 mg/kg per day. For example, in the treatment of conditions involving the neurotransmission of pain sensations, a suitable dosage level is about 0.001 to 25 mg/kg per day, preferably about 0.05 to 10 mg/kg per day, and especially about 0.1 to 5 mg/kg per day. A compound may be administered on a regimen of multiple times per day, such as 1 to 4 times per day, preferably once or twice per day. In the treatment of emesis using an injectable formulation, a suitable dosage level is about 0.001 to 10 mg/kg per day, preferably about 0.005 to 5 mg/kg per day, and especially about 0.05 to 5 mg/kg per day. A compound may be administered on a regimen of multiple times per day, such as 1 to 4 times per day, preferably once or twice per day.

The following examples are provided for the purpose of further illustration only and are not intended to be limitations on the disclosed invention.

EXAMPLE 1

Methyl trans-(+/−)-2-phenylcyclopentan-3-one-1-carboxylate

Step A: γ-δ-Dicarboxy-δ-phenyl-n-valeric acid

A mixture of 47 g of benzaldehyde and 50 g of ethyl cyanoacetate in 200 mL of absolute ethanol was treated with 2 mL of piperidine and the reaction was gently warmed. After the initial exothermic reaction had subsided, the reaction was heated to 60° C. (internal temperature) and then allowed to cool to room temperature. After 1 h, 22 g of powdered sodium cyanide was added in portions over 25 min and a mild exotherm ensued. The reaction was heated to an internal temperature of 80° C. and then allowed to cool to 35° C. before slow addition of 60 g of ethyl b-chloropropionate over 10 min. After heating in an oil bath at 80° C. for 5 h, the reaction was cooled and filtered to remove the precipitated sodium chloride. The filtrate was concentrated and to the residue was added 250 mL of water and 500 mL of concentrated HCl. The mixture was heated at reflux for 48 h and, while still hot, was treated with charcoal and filtered through Celite to remove some insoluble tarry material. On cooling, 25.8 g of the title compound as a pale yellow solid was obtained after filtration and air drying. The filtrate was extracted with EtOAc, washed with brine, dried with sodium sulfate and evaporated to provide an additional 32.8 g of less pure product which could be used directly.

Step B: Trimethyl γ-δ-dicarboxy-δ-phenyl-n-valerate

Into a solution of 21.2 g of the above triacid dissolved in 200 mL of methanol was bubbled 48.6 g of HCl gas. After heating at reflux overnight, the cooled reaction was concentrated and diluted with toluene. Most of the the aqueous bottom phase was removed via pipette and the toluene was evaporated. The residue was taken up in 200 mL of methanol and resaturated with HCl gas (53.5 g). After heating for another 20 h, the reaction was concentrated and the residue was dissolved in ether and washed with water, saturated NaHCO₃, and brine, then dried with sodium sulfate, and evaporated to provide 25.7 g of an oil which crystallized in the freezer. Trituration with 5% EtOAc in hexanes and filtration gave 18.4 g of the title triester as a white solid.

Step C: trans-(+/−)-2-Phenylcyclopentan-3-one-1-carboxylic acid

To 50 mL of anhydrous methanol was added a solution of 26 mL of 25% by wt sodium methoxide in methanol followed by 18.4 g of the above triester dissolved in 25 mL of methanol. After heating at reflux for 5.5 h, the solvent was evaporated and the residue was dissolved in 150 mL of concentrated HCl and 75 mL of water and heated at reflux overnight. The reaction, while still hot, was treated with charcoal and filtered through Celite. After cooling, 7.65 g of tide compound was obtained as a white solid after filtration and air drying. An additional 4.76 g of triacid was recovered by extraction of the filtrate with EtOAc.

Step D: Methyl trans-(+/−)-2-phenylcyclopentan-3-one-1-carboxylate

A solution of 4.17 g of above acid in 200 mL of methanol was saturated with HCl gas and stirred overnight. After cooling, the reaction was concentrated to a wet solid. This was taken up in EtOAc and washed with water, saturated NaHCO₃ solution, and brine, then dried with sodium sulfate and evaporated to furnish 4.4 g of the title product as a white solid. $^1$H NMR (CDCl₃): δ 2.0–2.15 (m, 1H), 2.3–2.5 (m, 2H), 2.62 (br dd, 1H), 3.25 (dt, 1H), 3.65 (s, 3H), 3.70 (br d, 1H), 7.12 (m, 2H), 7.24 (m, 1H), 7.32 (m, 2H).

EXAMPLE 2

Methyl 3-(SR)-(hydroxy)-2-(SR)-phenylcyclopentane-1-(SR)-carboxylate (Racemic 2,3-cis isomer) and methyl 3-(SR)-(hydroxy)-2-(RS)-phenylcyclopentane-1-(RS)-carboxylate (Racemic 2,3-trans isomer)

Method A:

To a solution of 4.43 g of methyl trans-(+/−)-2-phenylcyclopentan-3-one-1-carboxylate from Example 1, Step D in 65 mL of absolute methanol cooled in an ice/ethanol bath was added 807 mg of NaBH₄ in portions. After 1 h, the reaction was quenched with aqueous NH₄Cl. The solvent was evaporated and the residual oil was partitioned between EtOAc and water. The organic layer was washed with brine, dried with sodium sulfate and purified by Prep LC eluting first with 20% EtOAc in hexanes to provide 1.18 g of the higher $R_f$ 2,3-cis isomer. NMR (CDCl₃): δ 1.8–2.0 (m, 2H), 2.05–2.2 (m,1H), 2.3–2.4 (m,1H), 3.3–3.45 (m, 2H), 3.59 (s, 3H), 4.30 (m, 1H), 7.2–7.35 (m, 5H). Further elution with 40% EtOAc in hexanes provided 3.90 g of the lower $R_f$ 2,3-trans isomer. NMR (CDCl₃): δ 1.82 (m, 1H), 2.10 (m, 3H), 2.95 (q, 1H), 3.22 (dd, 1H), 3.60 (s, 3H), 4.20 (q, 1H), 7.22 (m, 3H), 7.31 (m, 2H).

Method B:

To a solution of 100 mg of methyl trans-(+/−)-2-phenylcyclopentan-3-one-1-carboxylate from Example 1, Step D in 5 mL of dry THF under N₂ and cooled in a dry ice/acetone bath was added dropwise 0.55 mL of 1M L-Selectride in THF. After 1 h, the reaction was quenched with dilute HCl. The mixture was extracted twice with ether and the organic layers were washed with brine, combined, dried with sodium sulfate and evaporated. The residue was purified by flash chromatography eluting with 20% EtOAc in hexanes to give only the higher $R_f$ 2,3-cis product isomer. The NMR was same as the higher $R_f$ isomer in Method A.

EXAMPLE 3

Methyl trans-(+/−)-2-(4-fluorophenyl)cyclopentan-3-one-1-carboxylate

Using essentially the same procedures as described in Example 1 but starting with 4-fluorobenzaldehyde, the title compound was prepared. NMR (CD₃OD): δ 2.0–2.2 (m, 1H), 2.3–2.5 (m, 2H), 2.56–2.76 (m, 1H), 3.1–3.3 (m, 1H), 3.68 (s, 3H), 3.72 (br d, 1H), 6.98–7.16 (m, 4H).

EXAMPLE 4

Methyl 3-(SR)-(hydroxy)-2-(SR)-(4-fluorophenyl) cyclopentane-1-(SR)-carboxylate (Racemic 2,3-cis isomer) and methyl 3-(SR)-(hydroxy)-2-(RS)-(4-fluorophenyl)cyclopentane-1-(RS)-carboxylate (Racemic 2.3-trans isomer)

Using essentially the same procedures as described in Example 2 but starting with the 4-fluorophenyl derivative, the title compounds were prepared. Higher $R_f$ isomer. NMR (CDCl$_3$): δ 1.86–2.0 (m, 2H), 2.1–2.2 (m, 1H), 2.29–2.36 (m, 1H), 3.28–3.4 (m, 2H), 3.6 (s, 3H), 4.28 (m, 1H), 7.0 (m, 2H), 7.24 (m, 2H). Lower $R_f$ isomer. NMR (CDCl$_3$): δ 1.80–1.86 (m, 1H), 2.06–2.17 (m, 3H), 2.87 (q, 1H), 3.19 (dd, 1H), 3.6 (s, 3H), 4.14 (q, 1H), 6.99 (m, 2H) 7.18 (m, 2H).

EXAMPLE 5

Methyl 2-(S)-(4-fluorophenyl)cyclopentan-3-one-1-(S)-carboxylate

Step A: (R)-α-Methylbenzylammonium 3-(S)-(hydroxy)-2-(R)-(4-fluorophenyl)cyclopentane-1-(R)-carboxylate To a solution of 3.0 gm of the lower $R_f$ trans alcohol of Example 4 in 20 mL of methanol was added 13 mL of 5N NaOH. The reaction was stirred at room temperature for 20 h and then concentrated in vacuo. The residue was taken up in water, acidified with 2N HCl, and extracted with three portions of EtOAc. The organic layers were washed with abportion of brine, combined, dried over sodium sulfate and evaporated to afford the crude acid as a white solid. To a warm solution of 2.3 gm of the above crude acid in 35 mL of isopropanol was added 930 mg (0.75 eq) of (R)-(+/-)-α-methylbenzyl amine. The solution was seeded and aged at room temperature for 4 hr, the solid was filtered, washed with isopropanol and then ether, and air dried to give 1.8 gm white solid. Recrystallization from another 30 mL of isopropanol afforded 1.1 gm of the title compound as a white solid. $[α]_D$ (EtOH)=–11.3 (c=0.37).

Step B: (S)-(–)-α-Methylbenzylammonium 3-(R)-(hydroxy)-2-(S)-(4-fluorophenyl)cyclopentane-1-(S)-carboxylate The mother liquors from Step A were combined and concentrated. The residue was taken up in water and acidified with 2N HCl and was extracted with 3 portions of EtOAc. The organic layers were washed with a portion of brine, combined, dried sodium sulfate and evaporated. The residue was dissolved in 25 mL of isopropanol and 0.75 gm (0.95 eq) of (S)-(–)-α-methylbenzyl amine was added. The solution was seeded and left at room temperature overnight after which the solid was filtered, washed with isopropanol and then ether, and air dried to give 1.56 gm white solid. Recrystallization from another 30 mL of isopropanol afforded 1.3 gm of the title compound as a white solid. $[α]_D$ (EtOH) =+12.5 (c=0.44).

Step C: 3-(S)-(Hydroxy)-2-(R)-(4-fluorophenyl)cyclopentane-1-(R)-carboxylic acid The salt from Step A was dissolved in water and acidified with 2N HCl and was extracted with 3 portions of EtOAc. The organic layers were washed with a portion of brine, combined, dried over sodium sulfate and evaporated to give a white solid. $[α]_D$ (EtOH)=–19.9 (c=0.675).

Step D: 3-(R)-(Hydroxy)-2-(S)-(4-fluorophenyl)cyclopentane-1-(S)-carboxylic acid The salt from Step B was dissolved in water and acidified with 2N HCl and was extracted with 3 portions of EtOAc. The organic layers were washed with a portion of brine, combined, dried over sodium sulfate and evaporated to give a white solid. $[α]_D$ (EtOH)=+21.6 (c=2.55).

Step E: Methyl 3-(S)-(hydroxy)-2-(R)-(4-fluorophenyl)cyclopentane-1-(R)-carboxylate Method A:

The salt from Step A was converted to the free acid as in Step C and dissolved in ether and a solution of diazomethane was added portionwise until the yellow color persisted. The excess diazomethane was quenched with acetic acid and the volatiles were removed in vacuo. The residue was purified by flash chromatography eluting with 20 to 40% EtOAc in hexanes to obtain 800 mg of title compound as an oil. $[α]_D$ (EtOH)=–30 (c=0.390).

Method B:

(R)-salt (8.7 gm) obtained as in Step A was converted to the free acid as in Step C to give 5.7 gm of crude acid. $[α]_D$ (EtOH)=–19.9 (c=0.675). This was taken up in 200 mL of methanol and saturated with HCl gas. The solution was stirred at room temperature for 16 h and then concentrated in vacuo. The residue was dissolved in water and extracted twice with ether. The organic layers were washed with a portion of brine, combined, dried over sodium sulfate and evaporated to give 6.0 gm of oil. $[α]_D$ (EtOH)=–30.5 (c=0.98).

Step F: Methyl 3-(R)-(hydroxy)-2-(S)-(4-fluorophenyl)cyclopentane-1-(S)-carboxylate Using essentially the same procedures as in Step E, the acid from the (S)-salt (7.50 gm) afforded 4.92 gm of the title compound as an oil. $[α]_D$ (EtOH)=+37 (c=1.05).

Step G: Methyl 2-(S)-(4-fluorophenyl)cyclopentan-3-one-1-(S)-carboxylate

Method A:

To a solution of 3.35 g of non-racemic alcohol obtained in Step F was added dropwise 5.8 mL of 8N Jones reagent over 1 min. After stirring at room temperature for 30 min, the reaction was concentrated in vacuo. The residue was diluted with water and extracted twice with ether. The organic layers were washed with a portion of brine, combined, dried over sodium sulfate and evaporated to give 0.55 gm of oil. Flash chromatography with 20 to 40% EtOAc in hexanes afforded 2.63 gm of title compound as a white solid. $[α]_D$ (EtOH)=+25 (c=0.62).

Method B:

A solution of 20.25 mL of oxalyl chloride in 200 mL of methylene chloride was cooled to <–70° C. in a dry ice/acetone bath. A solution of 32 mL of DMSO in 50 mL of methylene chloride was added dropwise while maintaining the temperature at <–60° C. After a further 15 min of stirring, a solution of 21.75 g of non-racemic alcohol obtained as in Step F in 100 mL of methylene chloride was added dropwise while maintaining the temperature at <–60° C. After a further 60 min of stirring, a solution of 127 mL of DIPEA in 100 mL of methylene chloride was added dropwise while maintaining the temperature at <–60° C. The ice bath was then removed and the reaction was allowed to warm to 0° C. over 1 h. The reaction was then slowly added (some gas evolution) to a mixture of 500 mL of ice water and 250 mL of 2N HCl. The layers were separated and the aqueous layer was extracted with a second portion of methylene chloride. The organic layers were each washed with brine, dried over sodium sulfate, combined and evaporated. The residue was purified by flash chromatography using a gradient of 20 to 30% ethyl acetate/hexanes as eluent. Evaporation of the product fractions afforded 21.7 g of title product as a white solid. $[α]_D$ (EtOH)=+27 (c=0.84).

EXAMPLE 6

Methyl [3-(SR), 5-(RS), 6-(SR), 7-(SR)]-6-(4-fluorophenyl)-3-(2-methoxy-5-((5-trifluoromethyl)tetrazol-1-yl)phenyl)-1-oxaspiro[4.4]nonane-7-carboxylate Step A: Methyl [1-(RS), 2-(SR), 3-(SR)]-2-(4-fluorophenyl)-1-(2-(acetoxymethyl)-prop-2-enyl)-1-(hydroxy)cyclo-pentane-3-carboxylate and methyl [1-(SR), 2-(SR), 3-(SR)]-2-(4-fluorophenyl)-1-(2-(acetoxymethylene)-prop-2-enyl)-1-(hydroxy)cyclopentane-3-carboxylate A solution of 1.85 g (7.8 mmol) of methyl 2-(RS)-(4-fluorophenyl)cyclopentanone-3-(RS)-carboxylate (from Example 3) and 3.15 g (10.8 mmol) of 3-acetoxy-2-[(trimethylstannyl)methyl]-1-propene in 8 mL of $CH_2Cl_2$ at −78° C. was treated with 1.60 mL (13.0 mmol) of boron trifluoride etherate. The reaction was warmed to −10° C. and was stirred for 20 h. The reaction was quenched with 40 mL of sat'd $NH_4Cl$; the resulting mixture was partitioned between 250 mL of ether and 150 mL of $H_2O$ and the layers were separated. The organic layer was washed with 200 mL sat'd KF, 200 mL sat'd NaCl, dried over $MgSO_4$ and concentrated in vacuo. Flash chromatography on 150 g of silica gel using 5:1 v/v hexanes/ether afforded 1.61 g (59%) of methyl [1-(RS), 2-(SR), 3-(SR)]-2-(4-fluorophenyl)-1-(2-(acetoxymethyl)-prop-2-enyl)-1-(hydroxy)cyclopentane-3-carboxylate as an oil. The eluant was changed to 1:1 v/v hexanes/ether to afford 0.95 g (33%) of methyl [1-(SR), 2-(SR), 3-(SR)]-2-(4-fluorophenyl)-1-(2-(acetoxymethyl)-prop-2-enyl)-1-(hydroxy)cyclopentane-3-carboxylate as an oil. For methyl [1-(RS), 2-(SR), 3-(SR)]-2-(4-fluorophenyl)-1-(2-(acetoxymethyl)-prop-2-enyl)-1-(hydroxy)cyclopentane-3-carboxylate: $^1$H NMR (500 MHz, $CDCl_3$): δ 1.86 (s, 1H), 1.89–2.02 (m, 2H), 2.01 (s, 3H), 2.07 (d, J=14.0, 1H), 2.23 (d, J=14.0), 2.28–2.32 (m, 2H), 3.12 (d, J=11.5, 1H), 3.38 (dt, J=6.5, 11.5, 1H), 3.56 (s, 3H), 4.51 (q, J=13.5, 2H), 4.98 (s, 1H), 5.13 (s, 1H), 7.02 (app t, J=9.0), 7.26–7.29 (m, 2H). HPLC: Chiralpak AD® 4.6×250 mm column, 80:20 v/v hexanes/iPrOH, 0.5 mL/min, 220 nm. Retention times: 1-(R), 2-(S), 3-(S) enantiomer, 11.9 min; 1-(S), 2-(R), 3-(R) enantiomer, 19.3 min. For methyl [1-(SR), 2-(SR), 3-(SR)]-2-(4-fluorophenyl)-1-(2-(acetoxymethyl)-prop-2-enyl)-1-(hydroxy)cyclopentane-3-carboxylate: $^1$H NMR (500 MHz, $CDCl_3$): δ 1.75 (d, J=14.5, 1H), 1.84 (d, J=14.5, 1H), 1.83–2.00 (m, 2H), 2.03 (s, 3H), 2.13–2.23 (m, 2H), 2.79 (s, 1H), 3.15 (app q, J=9.0, 1H), 3.49 (d, J=8.0, 1H), 3.65 (s, 3H), 4.53 (s, 2H), 4.89 (s, 1H), 5.11 (s, 1H), 7.01 (app t, J=8.0, 2H), 7.16–7.19 (m, 2H).

Step B: Methyl [5-(RS), 6-(SR), 7-(SR)]-6-(4-fluorophenyl)-3-(methylene)-1-oxaspiro[4.4]nonane-7-carboxylate A solution of 1.40 g (4.0 mmol) of methyl [1-(RS), 2-(SR), 3-(SR)]-2-(4-fluorophenyl)-1-(2-(acetoxymethyl)-prop-2-enyl)-1-(hydroxy)cyclopentane-3-carboxylate (from Example 6, Step A) in 25 mL of THF at −10° C. was treated with 4.0 mL of 1.0 M lithium bis(trimethylsilyl)amide solution in THF. The resulting solution was stirred cold for 5 min, then treated with 8.0 mL of 0.5 mL $ZnCl_2$ solution in THF. The cooling bath was removed and the reaction mixture was stirred at rt for 35 min. Tetrakis(triphenylphosphine)-palladium(0) (230 mg, 0.2 mmol) was added and the resulting mixture was heated at reflux for 20 h. The reaction was cooled, quenched with 50 mL of sat'd $NH_4Cl$, partitioned between 200 mL of ether and 50 mL of $H_2O$ and the layers were separated. The organic layer was washed with 50 mL of sat'd $NaHCO_3$, 50 mL of sat'd NaCl, dried over MgSO4 and concentrated in vacuo. Flash chromatography on 50 g of silica gel using 15:1 v/v hexanes/ether as the eluant afforded 1.03 g (88%) of the title compound as an oil. $^1$H NMR (500 MHz, $CDCl_3$): δ 1.84–1.95 (m, 2H), 2.04–2.09 (m, 1H), 2.22–2.31 (m, 1H), 2.47 (s, 2H), 3.17 (d, J=11.5, 1H), 3.31–3.36 (m, 1H), 3.56 (s, 3H), 3.93 (d, J=13.0, 1H), 4.19 (d, J=13.0, 1H), 4.67–4.69 (m, 1H), 4.78–4.80 (m, 1H), 6.95 (app t, J=8.5, 2H), 7.26–7.30 (m, 2H). Mass Spectrum ($NH_3$-CI): m/z 308 ($M+NH_4^+$, 100%).

Step C: Methyl [5-(RS), 6-(SR), 7-(SR)]-6-(4-fluorophenyl)-3-(oxo)-1-oxaspiro[4.41]nonane-7-carboxylate A solution of 1.10 g (3.8 mmol) of methyl [5-(RS), 6-(SR), 7-(SR)]-6-(4-fluorophenyl)-3-(methylene)-1-oxaspiro-[4.4]nonane-7-carboxylate (from Example 6, Step B) in 15 mL of 2:1 v/v acetone/$H_2O$ was treated with 5.0 mL of 2.5 % $OsO_4$ solution in t-butanol and stirred at rt for 5 min. The resulting dark brown solution was treated with 700 mg (6.0 mmol) of 4-methylmorpholine N-oxide and stirred at rt for 2 h. The reaction was quenched with 2.0 g of sodium bisulfite; the quenched mixture was partitioned between 200 mL of $CH_2Cl_2$ and 100 mL of $H_2O$ and the layers were separated. The organic layer was dried over $MgSO_4$. The aqueous layer was extracted with 200 mL of $CH_2C_2$; the extract was dried and combined with the original organic layer. The combined organic layers were concentrated in vacuo.

The crude diol was dissolved in 40 mL of 4:1 v/v THF/$H_2O$; the resulting solution was treated with 1.50 g (7.0 mmol) of sodium periodate and stirred for 20 h at rt. The reaction mixture was partitioned between 250 mL of ether and 100 mL of $H_2O$ and the layers were separated. The organic layer was dried over $MgSO_4$. The aqueous layer was extracted with 250 mL of ether; the extract was dried and combined with the original organic layer. The combined organics were concentrated in vacuo. Flash chromatography on 40 g of silica gel using 3:1 v/v hexanes/ether afforded 1.02 g (92%) of the title compound as an oil. $^1$H NMR (500 MHz, $CDCl_3$): δ 1.98–2.02 (m, 2H), 2.20–2.25 (m, 1H), 2.35–2.39 (m, 1H), 2.46 (s, 2H), 3.26 (d, J=11.0), 3.42–3.50 (m, 1H), 3.54 (d, J=17.5, 1H), 3.58 (s, 3H), 3.85 (d, J=17.5, 1H), 6.99 (app t, J=9.0), 7.26–7.32 (m, 2H). Mass Spectrum ($NH_3$-CI): δ 310 ($M+NH_4^+$, 100%).

Step D: Methyl [5-(RS), 6-(SR), 7-(SR)]-6-(4-fluorophenyl)-3-(trifluoromethylsulfonyl-oxy)-1-oxaspiro[4.4]non-3-ene-7-carboxylate A solution of 773 mg (2.6 mmol) of methyl [5-(RS), 6-(SR), 7-(SR)]-6-(4-fluorophenyl)-3-(oxo)-1-oxaspiro[4.4]nonane-7-carboxylate (from Example 6, Step C) in 25 mL of THF at −78° C. was treated with 5.80 mL of sodium bis(trimethylsilyl)amide solution in THF and stirred cold for 30 min. The resulting solution was treated with 1.40 g (3.6 mmol) of 5-chloro-2-N-bis(trifluoromethylsulfonyl)-pyridine in one portion as a solid. The reaction was warmed to −10° C. and stirred for 45 min. The reaction was quenched with 25 mL of 2.0 N HCl and partitioned between 150 mL of ether and 50 mL of $H_2O$ and the layers were separated. The organic layer was washed with 50 mL of sat'd $NaHCO_3$, 50 mL of sat'd NaCl, dried over $MgSO_4$ and concentrated in vacuo. Flash chromatography on 50 g of silica gel using 10:1 v/v hexanes/ether as the eluant afforded 857 mg (77%) of the title compound as a foam. $^1$H NMR (500 MHz, $CDCl_3$): δ 1.93–2.00 (m, 1H), 2.07–2.21 (m, 2H), 2.30–2.37 (m, 1H), 3.25 (d, J=11.5, 1H), 3.37–3.43 (m, 1H), 3.56 (s, 3H), 3.77 (dd, J=12.5, 2.0, 1H), 4.35 (dd, J=12.5, 2.0, 1H), 5.66 (t, J=2.0, 1H), 6.96 (app t, J=9.0, 2H), 7.23–7.26 (m, 2H). Mass Spectrum ($NH_3$-Cl) m/z 442 ($M+NH_4^+$, 100%).

Step E: Methyl [5-(RS), 6-(SR), 7-(SR)]-6-(4-fluorophenyl)-3-(trimethylstannyl)-1-oxaspiro[4.4]non-3-ene-7-carboxylate A mixture of 855 mg (2.0 mmol) of methyl [5-(RS), 6-(SR), 7-(SR)]-6-(4-fluorophenyl)-3-(trifluoromethylsulfonyloxy)-1-oxaspiro[4,4]non-3-ene-7-carboxylate (from Example 6, Step D), 1.50 g (4.6 mmol) of hexamethylditin, 2.75 mg (6.5 mmol) of LiCl and 45 mg (0.04 mmol) of tetrakis(triphenylphosphine)palladium(0) in 10 mL of dioxane was heated at 100° C. for 1 h. The reaction mixture was cooled, partitioned between 100 mL of ether and 50 mL of 50% sat'd NaHCO$_3$ and the layers were separated. The organic layer was washed with 50 mL of sat'd NaCl, dried over MgSO$_4$ and concentrated in vacuo. Flash chromatography on 50 g of silica gel using 15:1 v/v hexanes/ether as the eluant afforded 717 mg (81%) of the tide compound as an oil.

$^1$H NMR (500 MHz, CDCl$_3$): δ 0.06 (t, J=27.5, 9H), 1.91–2.00 (m, 2H), 2.14–2.21 (m, 1H), 2.27–2.35 (m, 1H), 3.14 (d, J=11.5, 1H), 3.40–3.45 (m, 1H), 3.57 (s, 3H), 3.62 (dd, J=12.5, 2.0, 1H), 4.43 (dd, J=12.5, 2.0, 1H), 5.62–5.70 (m, 1H), 6.89 (app t, J=8.5, 2H), 7.18–7.21 (m, 2H).

Step F: Methyl [5-(RS), 6-(SR), 7-(SR)]-6-(4-fluorophenyl)-3-(2-methoxy-5-((5-trifluoromethyl)tetrazol-1-yl)phenyl)-1-oxaspiro[4.4]non-3-ene-7-carboxylate a) 2-Bromo-4-aminoanisole A mixture of 670 mg (2.9 mmol) of 2-bromo-4-nitroanisole and 1.20 g (21.1. mmol) of iron powder in 10 mL of 1:1 v/v HOAc/H$_2$O was heated at 80° C. for 1.5 h. The mixture was cooled and filtered onto a pad of Celite. The flask and filtered solids were rinsed with 100 mL of EtOAc and 100 mL of H$_2$O. The filtrate was transfered to a separatory fumel and the layers were separated. The organic layer was washed with 50 mL of sat'd NaHCO$_3$, 50 mL sat'd NaCl, dried over MgSO$_4$ and concentrated in vacuo. Flash chromatography on 25 g of silica gel using 3:2 v/v hexanes/ether as the eluant afforded 504 mg (86%) of the title compound as an oil.

$^1$H NMR (500 MHz, CDCl$_3$): δ 3.54 (br s, 2H), 3.81 (s, 3H), 6.60 (dd, J=8.5, 2.5, 1H), 6.74 (d, J=8.5, 1H), 6.93 (d, J=2.5, 1H).

b) 2-Bromo-4-(trifluoroacetamido)anisole

A solution of 500 mg (2.5 mmol) of 2-bromo-4-aminoanisole and 1.31 mL (7.5 mmol) of DIEA in 10 mL of CH$_2$Cl$_2$ at 0° C. was treated with 0.71 mL (5.0 mmol) of trifluoroacetic anhydride. The cooling bath was removed and the resulting mixture was stirred at rt for 20 h. The reaction mixture was partitioned between 100 mL of ether and 50 mL of H$_2$O and the layers were separated. The organic layer was washed with 50 mL of 2.0 N HCl, 50 mL of sat'd NaHCO$_3$, 50 mL of sat'd NaCl, dried over MgSO$_4$ and concentrated in vacuo. Flash chromatography on 30 g of silica gel using 4:1 v/v hexanes/ether as the eluant afforded 709 mg (95%) of the product as an oil. $^1$H NMR (400 MHz, CDCl$_3$): δ 3.91 (s, 3H), 6.91 (d, J=8.8), 7.51 (dd, J=8.8, 2.4, 1H), 7.78 (d, J=2.4, 1H).

c) 2-Bromo-4-(5-(trifluoromethyl)tetrazol-1-yl)anisole

A mixture of 705 mg (2.4 mmol) of 2-bromo-4-(trifluoroacetamido)anisole and 625 mg (2.4 mmol) of triphenylphosphine in 25 mL of CC14 was heated at reflux. After 4 h, a second 625 mg portion of triphenylphosphine was added and heating was continued for 16 h. The reaction mixture was cooled and concentrated in vacuo. The residue was dissolved in 15 mL of DMF, treated with 650 mg (10.0 mmol) of NaN$_3$ and stirred at rt. After 1.5 h, the reaction mixture was concentrated in vacuo and the residue was partitioned between 200 mL of ether and 100 mL of H$_2$O. The layers were separated; the organic layer was washed with 2×100 mL of H$_2$O, dried over MgSO$_4$ and concentrated in vacuo. Flash chromatography on 40 g of silica gel using 4:1 v/v hexanes/ether as the eluant afforded 700 mg (91%) of the title compound as an oil. $^1$H NMR (500 MHz, CDCl$_3$): δ 4.01 (s, 3H), 7.07 (d, J=8.5, 1H), 7.43 (dd, J=8.5, 2.5), 7.71 (d, J=2.5, 1H).

d) Methyl [5-(RS), 6-(SR), 7-(SR)]-6-(4-fluorophenyl)-3-(2-methoxy-5-((5-trifluoromethyl)tetrazol-1-yl)phenyl)-1-oxaspiro[4.4]non-3-ene-7-carboxylate A mixture of 107 mg (0.24 mmol) of methyl [5-(RS), 6-(SR), 7-(SR)]-6-(4-fluorophenyl)-3-(trimethylstannyl)-1-oxaspiro-[4,4]non-3-ene-7-carboxylate (from Example 6, Step E), 115 mg (0.36 mmol) of 2-bromo-4-(5-(trifluoromethyl)tetrazol-1-yl)anisole, 30 mg (0.71 mmol) of LiCl and 6 mg (0.0052 mmol) of tetrakis(triphenylphosphine)palladium(0) in 3 mL of dioxane was heated at 100° C. under nitrogen for 1.5 h. Alternativelyh, (Ph$_3$P)$_2$PdCl$_2$ in toluene can be used in place of (Ph$_3$P)$_4$Pd and LiCl in dioxane. The reaction mixture was cooled and partitioned between 40 mL of ether and 20 mL of H$_2$O and the layers were separated. The organic layer was washed with 20 mL of sat'd KF, 20 mL of sat'd NaCl, dried over MgSO$_4$ and concentrated in vacuo. Flash chromatography on 12 g of silica gel using 10:1 v/v hexanes/EtOAc as the eluant afforded 81 mg (65%) of the title compound as an oil. $^1$H NMR (500 MHz, CDCl$_3$): δ 1.88–2.03 (m, 1H), 2.07–2.13 (m, 1H), 2.23–2.30 (m, 1H), 2.33–2.39 (m, 1H), 3.32 (d, 1H), 3.40–3.48 (m, 1H), 3.59 (s, 3H), 3.94 (s, 3H), 4.07 (dd, J=12.0, 2.0), 4.71 (dd, J=12.0, 2.0), 6.39 (t, J=2.0, 1H), 6.85–6.91 (m, 2H), 6.96 (d, J=2.0, 1H), 7.02 (d, J=8.5, 1H), 7.25–7.28 (m, 2H), 7.32 (dd, J=8.5, 2.0, 1H).

Step G: Methyl [3-(SR), 5-(RS), 6-(SR), 7-(SR)]-6-(4-fluorophenyl)-3-2-methoxy-5-((5-trifluoromethyl)tetrazol-1-yl)phenyl)-1-oxaspiro[4.4]nonane-7-carboxylate A mixture of 110 mg (0.21 mmol) of methyl [5-(RS), 6-(SR), 7-(SR)]-6-(4-fluorophenyl)-3-(2-methoxy-5-((5-trifluoromethyl)-tetrazol-1-yl)phenyl)-1-oxaspiro[4.4]non-3-ene-7-carboxylate (from Example 1, Step F) and 25 mg of 20% Pd(OH)$_2$/C in 10 mL of 20:1 v/v MeOH/HOAc was hydrogenated at 45 psi for 1.5 h. The catalyst was filtered onto a pad of Celite, the reaction flask and filter cake were rinsed with 100 mL of EtOAc and the filtrate was concentrated in vacuo. The residue was partitioned between 50 mL of ether and 25 mL of sat'd NaHCO$_3$ and the layers were separated. The organic layer was washed with 25 mL of sat'd NaCl, dried over MgSO$_4$ and concentrated in vacuo. Flash chromatography on 6 g of silica gel using 20:7:2 v/v/v hexanes/CH$_2$Cl$_2$/ether as the eluant afforded 36 mg (33%) of the title compound as an oil. $^1$H NMR (500 MHz, CDCl$_3$): δ 1.88–2.00 (m, 3H), 2.18–2.25 (m, 2H), 2.29–2.35 (m, 1H), 3.12 (t, J=8.5, 1H), 3.21 (d, J=11.0, 1H), 3.30–3.36 (m, 1H), 3.56 (s, 3H), 3.73–3.80 (m, 1H), 3.82 (s, 3H), 4.10 (t, J=11.0, 1H), 6.71 (d, J=2.5, 1H), 6.87–6.92 (m, 2H), 7.23 (dd, J=8.5, 2.5, 1H), 7.29–7.32 (m, 2H). Mass Spectrum (NH$_3$-CI): m/z 538 (M+NH$_4^+$, 65%), 521 (M+H, 70%).

EXAMPLE 7

(5R,6S,7S)-6-(4-Fluorophenyl)-3-[2-methoxy-5-(5-trifluoromethyl-tetrazol-1-yl)-pyridin-3-yl]-1-oxaspiro[4.4]non-3-ene-7-carboxylic acid methyl ester Step A: 2-Hydroxy-3-bromo-5-nitropyridine The title compound was synthesized by the method of E. V. Brown and H. T Burke, *J. Amer. Chem. Soc.* 77, p6053–6054 (1955).

Step B: 2-Methoxy-3-bromo-5-nitropyridine

The title compound was synthesized from 2-hydroxy-3-bromo-5-nitropyridine by the method of H. J. W. van den Haak et al, Recl.Trav. Chim. Pays-Bas 99(3), p83–87 (1980) using trimethyloxonium tetrafluoroborate in methylene chloride.

Step C: 2-Methoxy-3-bromo-5-aminopyridine

The title compound was synthesized in 70% yield by a tin metal reduction in concentrated hydrochloric acid of the nitro group as described by T. Batkowski, Roczniki Chemii, 41, p729–740, (1967).

Step D: 2-Methoxy-3-bromo-5-(5-trifluoromethyl-tetrazol-1-yl)-pyridine

The title compound was synthesized by the method described in Example 6, Steps F b) and F c) wherein the 5-amino group is transformed into 5-trifluoromethyl-tetrazol-1-yl via sequential N-trifluoroacetylation, iminochloride formation from triphenylphosphine in carbon tetrachloride, and finally cyclization to the tetrazole with sodium azide in dimethylformamide.

Step E: (5R,6S,7S)-6-(4-fluorophenyl)-3-[2-methoxy-5-(5-trifluoromethyl-tetrazol-1-yl)-pyridin-3-yl]-1-oxaspiro[4.4]non-3-ene-7-carboxylic acid methyl ester The title compound was synthesized according to the procedure given in Example 6, Step F d), wherein 2-methoxy-3-bromo- 5-(5-(trifluoromethyl-tetrazol-1-yl)-pyridine replaced 2-bromo-4-(5-(trifluoromethyl)tetrazol-1-yl)anisole. $^1$H NMR (400 MHz, CDCl$_3$): δ 7.557(d, J=3 Hz,1H); 7.23(m, 2H); 7.156(t, J=2 Hz, 1H); 6.8–6.9(m, 2H); 6.715(d, J=3 Hz, 1H); 4.61(dd, J=11 Hz, J=2 Hz, 1H); 3.96 (dd, J=11 Hz, J=2 Hz, 1H); 3.65(s,3H); 3.56(s, 3H); 3.4–3.5 (m, 1H); 3.3–3.37(m,1H); 2.22–2.40(m, 1H); 1.95–2.1(m, 1H). Mass spectrum: 520 (M+1).

EXAMPLE 8

(3S,5R,6S,7S)-6-(4-Fluorophenyl)-3-[2-methoxy-5-(5-trifluoromethyl-tetrazol-1-yl)-pyridin-3-yl]-1-oxaspiro[4.4]nonane-7-carboxylic acid methyl ester The title compound was prepared by hydrogenation with H$_2$ in methanol over 20% palladium hydroxide of 6-(4-fluorophenyl)-3-[2-methoxy-5-(5-trifluoromethyl-tetrazol-1-yl)-pyridin-3-yl]-1-oxaspiro[4.4]non-3-ene-7-carboxylic acid methyl ester by the method given in Example 6, Step G. H NMR (400 MHz, CDCl$_3$): δ 7.435(d, J=3 Hz,1H) ;7.20–7.28(m, 2H); 6.78–6.85(m, 2H); 6.503(d, J=3 Hz, 1H); 4.12(t, J=7 Hz 1H); 3.67 (m, 1H); 3.55(s,3H); 3.53(s, 3H); 3.27–3.45(m, 1H); 3.15–3.20(m,1H); 3.10(t, J=8 Hz, 1H); 2.25–3.33(m, 2H); 2.15–2.24(m, 1H); 1.85–2.0(m, 2H); 1.69(dd, J=13 Hz, J=9 Hz, 1H). Mass spectrum: 522 (M+1).

EXAMPLE 9

(5R,6S,7S)-6-(4-Fluorophenyl)-3-[2-methoxy-5-(5-trifluoromethyl-tetrazol-1-yl)-pyridin-2-yl]-1-oxaspiro[4.4]non-3-ene-7-carboxylic acid methyl ester Step A: 2-Bromo-3-methoxy-6-nitropyridine To a 500 mL round bottomed flask fitted with a Teflon stir bar and a thermometer was added 90 mL of concentrated sulphuric acid and 37.6 g of 2-bromo-3-methoxypyridine (200 mmol). The flask was warmed in an oil bath to 60° C. Added slowly over 1h 16.5 mL (350 mmol) of fuming nitric acid (90%, d=1.50). Maintain the temperature between 60 and 70° during the addition. Stir at 60° for 3h after the addition was complete, then at room temperature overnight. By TLC (70/30 hex/EtOAc) is consumed. The product mixture was poured into 600 mL of ice/water, from which the product precipitated. This material was filtered, washed with 3×200 mL of cold water and then 100 mL of saturated sodium bicarbonate. After drying in the filter funnel in a stream of air, the remaining water was removed under reduced pressure, to give 16.5 g of a solid. H NMR (400 MHz, CDCl$_3$): δ 8.27(d, J=8 Hz,1H); 6.32(d, J=8 Hz,1H); 4.06(s, 3H).

Step B: 2-Bromo-3-methoxy-6-aminopyridine

The title compound was synthesized in 80% yield by a tin metal reduction in concentrated hydrochloric acid as described by T. Batkowski, Roczniki chemii, 41, p729–740, (1967). H NMR (400 MHz, CDCl$_3$): δ 7.06(d, J=8 Hz,1H); 6.41(d, J=8 Hz,1H); 4.30(bs, 2H); 3.80(s, 3H).

Step C: 2-Bromo-3-methoxy-6-(5-trifluoromethyl-tetrazol-1-yl)-pyridine

The title compound was synthesized by the method described in Example 6, Steps F b) and F c), wherein the 6-amino group is transformed into 5-trifluoromethyl-tetrazol-1-yl via sequential trifluoroacetylation, iminochloride formation from triphenylphosphene in carbon tetrachloride and finally cyclization to the tetrazole with sodium azide in dimethylformamide.

Step D: (5R,6S,7S)-6-(4-Fluorophenyl)-3-[2-methoxy-5-(5-trifluoromethyl-tetrazol-1-yl)-pyridin-2-yl]-1-oxaspiro[4.4]non-3-ene-7-carboxylic acid methyl ester The title compound was synthesized according to the procedure given in Example 6, Step F d), wherein 2-bromo-3-methoxy-6-(5-trifluoromethyl-tetrazol-1-yl)-pyridine replaced 2-bromo-4-(5-(trifluoromethyl)tetrazol-1-yl)anisole. $^1$H NMR (400 MHz, CDCl$_3$): δ 7.71(d, J=7 Hz,1H); 7.41(d, J=7 Hz, 1H); 7.23(m, 2H); 6.85(t, J=8 Hz, 2H); 6.752(d, J=2 Hz, 1H); 4.83(dd, J=11 Hz, J=2 Hz, 1H); 4.195 (dd over multiplet, J=11 Hz, J=2 Hz, 2H); 4.01(s,3H); 3.57(s, 3H); 3.4–3.5(m, 1H); 3.3–3.37(m,1H); 2.3–2.45(m, 1H); 2.22–2.30(m, 1H); 2.10–2.18(m, 1H). Mass spectrum: 520 (M+1).

EXAMPLE 10

(3S,5R,6S,7S)6-(4-Fluorophenyl)-3-[3-methoxy-6-(5-trifluoromethyl-tetrazol-1-yl)-pyridin-2-yl]-1-oxaspiro[4.4]nonane-7-carboxylic acid methyl ester This material was made by hydrogenation with H$_2$ in methanol over 20% palladium hydroxide of 6-(4-fluorophenyl)-3-[3-methoxy-6-(5-trifluoromethyl-tetrazol-1-yl)-pyridin-2-yl]-1-oxaspiro[4.4]non-3-ene-7-carboxylic acid methyl ester by the method given in Example 6, Step G. NMR (400 MHz, CDCl$_3$): δ 7.66(d, J=7Hz,1H); 7.29(m, 3H); 6.90(t, J=9 Hz, 2H); 4.1(t, J=7Hz, 1H); 3.88 (s over multiplet, 3H+1H); 3.54(s,3H); 3.2–3.35(m, 3H); 2.25–2.33 (m, 1H); 2.1–2.22(m, 3H); 1.90–2.0(m, 2H); Mass spectrum: 522 (M+1).

EXAMPLE 11

(5R,6S,7S)-6-(4-Fluorophenyl)-3-[5-trifluoromethoxydihydrobenzofuran-7-yl]-1-oxaspiro[4.4]non-3-ene-7-carboxylic acid methyl ester The title compound was synthesized in 44% yield via the method given in Example 6, Step F d), employing 7-bromo-5-trifluoromethoxy-[2,3]-dihydrobenzofuran (prepared by the literature method) instead of 2-bromo-4-(5-(trifluoromethyl)tetrazol-1-yl)anisole.

$^1$H NMR (400 MHz, CDCl$_3$): δ 7.24(m,2H); 6.84–6.92 (m, 3H); 6.45(d, J=2 Hz, 1H); 6.36(t, J=2 Hz, 1H); 4.70(dd, J=11 Hz, J=2 Hz, 1H); 4.62–4.68(m, 2H); 4.05 (dd, J=11 Hz, J=2 Hz, 1H); 3.55(s, 3H); 3.4–3.5(m, 1H); 3.3–3.37(m,1H); 2.20(t, J=9 Hz, 2H); 2.22–2.40(m, 2H); 1.90–2.12(m, 2H); Mass spectrum: 479(M+1).

EXAMPLE 12

(5R,6S, 7S)-6-(4-Fluorophenyl)-3-(1-methyl-5-trifluoromethyl-benzimidazol-7-yl)-1-oxaspiro[4.4]non-3-ene-7-carboxylic acid methyl ester The title compound was prepared according to the procedure given in Example 6, Step F d). The bromide intermediates were prepared as outlined above. $^1$H NMR (400 MHz, CD$_3$OD): δ 1.98–2.42 (m, 4H), 3.42 (s, 3H), 3.57 (s, 3H), 4.30 (dd, 1H), 4.78 (dd, 1H), 5.99 (m, 1H), 7.02 (s, 1H), 7.06 (t, 2H), 7.45 (m, 2H), 7.86 (s, 1H), 8.17 (s, 1H). Mass spectrum: 475 (M+1)

EXAMPLE 13

(5R,6S, 7S)-6-(4-Fluorophenyl)-3-[1-(tert-butyloxycarbonyl)-6-trifuoromethyl-benzimidazol-4-yl]-1-oxaspiro [4.4]non-3-ene-7-carboxylic acid methyl ester The title compound was prepared according to the procedure given in Example 6, Step F d). The bromide intermediates were prepared as outlined above. $^1$H NMR (400 MHz, CD$_3$OD): δ 1.71 (s, 9H), 1.97–2.40 (m, 4H), 3.49 (m, 1H), 3.58 (s, 3H), 4.29 (dd, 1H), 5.00 (dd, 1H), 6.88 (t, 2H), 7.07 (m, 1H), 7.29 (s, 1H), 7.32 (m, 2H), 8.21 (m, 1H), 8.68 (s, 1H). Mass spectrum: 561 (M+1), 461 (M-Boc)

EXAMPLE 14

(5R, 6S, 7S)-6-(4-Fluorophenyl)-3-(5-trifluoromethyl-benzimidazol-7-yl)-1-oxaspiro[4.4]nonane-7-carboxylic acid methyl ester Step A: (5R, 6S, 7S)-6-(4-Fluorophenyl)-3-[1-(tert-butyloxy-carbonyl)-6-trifluoromethyl-benzimidazol-4-yl)-1-oxaspiro[4.4]nonane-7-carboxylic acid methyl ester The title compound was prepared by hydrogenation of (5R, 6S, 7S)-6-(4-fluorophenyl)-3-[1-(tert-butyloxycarbonyl)-6-trifuoromethyl-benzimidazol-4-yl)-1-oxaspiro[4.4]non-3-ene-7-carboxylic acid methyl ester (19.5 mg) in methanol (1.5 mL) and glacial acetic acid (0.15 mL) over 20% palladium hydroxide-on-carbon (8 mg) by the method given in Example 6, Step G; yield 13.5 mg. Mass spec (NH$_3$/CI): 463 (M+1).

Step B: (5R, 6S, 7S)-6-(4-Fluorophenyl)-3-(5-trifluoromethyl-benzimidazol-7-yl)-1-oxaspiro[4.4]nonane-7-carboxylic acid methyl ester A solution of (5R, 6S, 7S)-6-(4-fluorophenyl)-3-[1-(tert-butyloxycarbonyl)-6-trifuoromethyl-benzimidazol-4-yl)-1-oxaspiro[4.4]nonane-7-carboxylic acid methyl ester (13.5 mg, 0.024 mmol) in methylene chloride (1 mL) was treated with anhydrous zinc bromide (11 mg, 0.049 mmol) for 6 hours at room temperature. The reaction was quenched with saturated NaHCO$_3$ solution, diluted with methylene chloride, the organic layer separated and washed with saturated brine solution, dried (Na$_2$SO$_4$), and evaporated to obtain 8.4 mg of the title compound. 400 MHz $^1$H NMR (CD$_3$OD): δ 1.92–2.11 (m, 3H), 2.24–2.37 (m, 2H), 2.48 (dd, 1H), 3.13 (m, 1H), 3.41 (m, 1H), 3.56 (s, 3H), 4.17 (t, 1H), 6.75 (br s, 1H), 7.06 (t, 2H), 7.42 (m, 2H), 7.68 (br s, 1H), 8.28 (br s, 1H); Mass spec (NH$_3$/CI): δ 414 (M+1).

EXAMPLE 15

(5R, 6S, 7S)-6-(4-Fluorophenyl)-3-(((5-trifluoromethyl)tetrazol-1-yl)-1H-indol-7-yl)-1-oxaspiro[4.4]non-3-ene-7-carboxylic acid methyl ester Step A: 5-Amino-7-bromo-1H-indole A mixture of 7-bromo-5-nitro-1H-indole (prepared according to the procedure set forth in L. L. Melhado et al., *Phytochemistry*, 21, 2879 (1982)) (550 mg, 2.28 mmol) in glacial acetic acid (16 mL) was treated with zinc dust (700 mg, 10.7 mmol) for 2 hours at room temperature. The mixture was then filtered through a pad of Celite, the filtrate evaporated, and coevaporated several times with toluene. The residue was taken up in methylene chloride (with a small amount of methanol), washed with saturated NaHCO$_3$ solution, dried (Na$_2$SO$_4$), and evaporated. Flash chromatography eluting with 20% ethyl acetate in hexane afforded 153 mg of the title compound.

Step B: 7-Bromo-5-(5-trifluoromethyl-tetrazol-1-yl)-1H-indole

The title compound was prepared following the method described in Example 6, Steps F b) and F c), wherein the 5-amino group is transformed into 5-trifluoromethyl-tetrazol-1-yl via sequential trifluoroacetylation, treatment with triphenylphosphine in carbon tetrachloride to generate the imino chloride, and treatment with sodium azide in DMF to elaborate the tetrazole ring.

Step C: (5R, 6S, 7S)-6-(4-Fluorophenyl)-3-(((5-trifluoromethyl)tetrazol-1-yl)-1H-indol-7-yl)-1-oxaspiro [4.4]non-3-ene-7-carboxylic acid methyl ester A mixture of 7-bromo-5-(5-trifluoromethyl-tetrazol-1-yl)-1H-indole (30 mg, 0.090 mmol), methyl [5R, 6S, 7S]-6-(4-fluorophenyl)-3-(trimethylstannyl)-1-oxaspiro[4.4]non-3-ene-7-carboxylate (39 mg, 0.089 mmol), and bis-(triphenylphosphine)-palladium(II) chloride (3.0 mg, 0.004 mmol) in toluene (1.5 mL) was heated under a nitrogen atmosphere for 2 hours. The cooled reaction mixture was evaporated, and the residue subjected to flash chromatography eluting with 25% ethyl acetate in hexane to afford 35 mg of the title compound. 400 MHz $^1$H NMR (CD$_3$OD): δ 2.01 (m, 1H), 2.16 (m, 1H), 2.38 (m, 2H), 3.58 (s, 3H), 4.10 (dd, 1H), 4.80 (dd, 1H), 6.53 (m, 1H), 6.70 (d, 1H), 6.80 (d, 1H), 6.90 (t, 2H), 7.33 (m, 2H), 7.52 (d, 1H), 7.72 (d, 1H); Mass spec (NH$_3$/CI): 528 (M+1); 545 (M+NH$_3$)

EXAMPLE 16

(5R, 6S, 7S)-6-(4-Fluorophenyl)-3-(((5-trifluoromethyl)tetrazol-1-yl)-1H-indol-7-yl)-1-oxaspiro[4.4]nonane-7-carboxylic acid methyl ester The title compound was prepared by hydrogenation of (5R, 6S, 7S)-6-(4-fluorophenyl)-3-(((5-trifluoromethyl) tetrazol-1-yl)-1H-indol-7-yl)-1-oxaspiro[4.4]non-3-ene-7-carboxylic acid methyl ester (14.4 mg) in methanol (1.5 mL) and glacial acetic acid (0.10 mL) over 20% palladium hydroxide-on-carbon (10 mg) by the method given in Example 6, Step G; yield 14 mg. 400 MHz $^1$H NMR (CD$_3$OD): δ 1.93–2.09 (m, 3H), 2.30 (m, 2H), 2.48 (dd, 1H), 3.40 (m, 1H), 3.53 (s, 3H), 3.93 (m, 1H), 4.20 (t, 1H), 6.48 (d, 1H), 6.57 (d, 1H), 6.91 (t, 2H), 7.30 (d, 1H), 7.38 (m, 2H), 7.57 (d, 1H); Mass spec (NH$_3$/CI): 530 (M+1); 547 (M+NH$_3$).

EXAMPLE 17

(3S, 5R, 6S, 7S)-6-(4-Fluorophenyl)-3-(((5-trifluoromethyl)tetrazol-1-yl)-1H-indol-7-yl)-1-oxaspiro[4.4]nonane-7-methanol The title compound was prepared following the procedure described in Example 15, Step C, using 7-bromo-5-(5-trifluoromethyl-tetrazol-1-yl)-1H-indole and (5R, 6S, 7S)-6-(4-fluorophenyl)-3-(trimethylstannyl)-1-oxaspiro[4.4]non-3-ene-7-methanol as substrates for the cross-coupling reaction followed by catalytic hydrogenation according to the procedure described in Example 16. 400 MHz $^1$H NMR (CD$_3$OD): δ 1.70 (m, 1H), 2.42 (dd, 1H), 2.65 (m, 1H), 2.78 (d, 1H), 3.91 (m, 1H), 4.20 (t, 1H), 6.51 (d, 1H), 6.57 (d, 1H), 6.93 (t, 2H), 7.28 (d, 1H), 7.38 (m, 2H), 7.55 (d, 1H); Mass spec (NH$_3$/CI): 502 (M+1); 519 (M+NH$_3$).

EXAMPLE 18

(3S, 5R, 6S, 7S)-7-(Dimethylaminomethyl)-6-(4-fluorophenyl)-3-(((5-trifluoromethyl)tetrazol-1-yl)-1H-indol-7-yl)-1-oxaspiro[4.4]nonane hydrochloride A solution of (3S, 5R, 6S, 7S)-6-(4-fluorophenyl)-3-(((5-trifluoromethyl)tetrazol-1-yl)-1H-indol-7-yl)-1-oxaspiro[4.4]nonane-7-methanol (78 mg, 0.156 mmol) in dichloromethane (DCM) (4 mL) was treated with 72 mg (0.17 mmol) of Dess-Martin reagent. After one hour, the reaction was diluted with DCM, washed with 1N KOH, saturated brine solution, dried ($MgSO_4$), and evaporated. The crude aldehyde (30 mg, 0.060 mmol) in methanol (1.5 mL) was treated with 150 µL (0.3 mmol) of dimethylamine (2.0M solution in methanol) and sodium cyanoborohydride (3.9 mg, 0.062 mmol) overnight at room temperature and then evaporated. The title compound was obtained pure by silica gel chromatography eluting initially with 5% MeOH/DCM, then with 5% MeOH/DCM containing 0.5% $NH_4OH$, and finally with 10% MeOH/DCM containing 0.5% $NH_4OH$; yield 11.5 mg. The product was converted into the hydrochloride salt with 1M HCl in diethyl ether. 400 MHz $^1$H NMR ($CD_3OD$): δ 1.58 (m, 1H), 2.32 (s, 6H), 2.43 (dd, 1H), 2.51 (t, 1H), 2.67 (d, 1H), 2.75 (m, 1H), 3.92 (m, 1H), 4.20 (t, 1H), 6.49 (d, 1H), 6.57 (d, 1H), 6.96 (t, 2H), 7.29 (d, 1H), 7.39 (m, 2H), 7.56 (d,1H); Mass spec ($NH_3$/CI): 529 (M+1)

EXAMPLE 19

(5R, 6S, 7S)-7-6-(4-Fluorophenyl)-3-(((5-trifluoromethyl)tetrazol-1-yl)-1-methyl-indol-7-yl)-1-oxaspiro[4.4]non-3-ene-7-methanol Step A: 7-Bromo-5-(5-trifluoromethyl-tetrazol-1-yl)-1-methyindole To a solution of 7-bromo-5-(5-trifluoromethyl-tetrazol-1-yl)-1H-indole (115 mg, 0.346 mmol) in DMF (2 mL) was added sodium hydride (80% dispersion in mineral oil) (12 mg, 0.417 mmol). After gas evolution ceased, iodomethane (33 µL, 0.530 mmol) was added, and the mixture was stirred for 2 hours at room temperature. The mixture was diluted with diethyl ether, washed with water, 2N hydrochloric acid, saturated sodium hydrogencarbonate solution, saturated brine solution, dried ($MgSO_4$), and evaporated. Silica gel chromatography eluting with 10% diethyl ether/hexane afforded pure title compound; yield 83 mg of a white solid.

Step B: (5R, 6S, 7S)-7-6-(4-Fluorophenyl)-3-(((5-trifluoromethyl)tetrazol-1-yl)-1-methyl-indol-7-yl)-1-oxaspiro[4.4]non-3-ene-7-methanol The title compound was prepared following the procedure described in Example 15, Step C, using 7-bromo-5-(5-trifluoromethyl-tetrazol-1-yl)-1-methyl-indole and (5R, 6S, 7S)-6-(4-fluorophenyl)-3-(trimethylstannyl)-1-oxaspiro[4.4]non-3-ene-7-methanol as substrates for the cross-coupling reaction. 400 MHz $^1$H NMR ($CD_3OD$): δ 1.74 (m, 1H), 2.70 (m, 1H), 2.93 (d, 1H), 3.35 (dd, 1H), 3.41 (s, 3H), 3.54 (dd, 1H), 4.30 (dd, 1H), 4.75 (dd, 1H), 5.91 (m, 1H), 6.59 (d, 1H), 6.78 (d, 1H), 7.00 (t, 2H), 7.28 (d, 1H), 7.42 (m, 2H), 7.70 (d, 1H).

EXAMPLE 20

(3S, 5R, 6S, 7S)-7-6-(4-Fluorophenyl)-3-(((5-trifluoromethyl)tetrazol-1-yl)-1-methyl-indol-7-yl)-1-oxaspiro[4.4]nonane-7-methanol The title compound was prepared by catalytic hydrogenation according to the procedure described in Example 16. 400 MHz $^1$H NMR ($CD_3OD$): δ 1.70 (m, 1H), 1.91 (m, 1H), 2.04 (dd, 1H), 2.47 (dd, 1H), 2.61 (m, 1H), 2.72 (d, 1H), 3.49 (dd, 1H), 4.11 (s, 3H), 4.14 (t, 1H), 4.37 (m, 1H), 6.37 (dd, 1H), 6.52 (d, 1H), 6.78 (t, 2H), 7.28 (d, 1H), 7.33 (m, 2H), 7.51 (d, 1H); Mass spec ($NH_3$/CI): 516 (M+1); 533 (M+$NH_3$).

EXAMPLE 21

(5R, 6S, 7S)-7-(2-Fluoroethylaminomethyl)-6-(4-fluorophenyl)-3-(((5-trifluoromethyl)tetrazol-1-yl)-1-methyl-indol-7-yl)-1-oxaspiro[4.4]non-3-ene hydrochloride A solution of (5R, 6S, 7S)-7-6-(4-fluorophenyl)-3-(((5-trifluoromethyl)tetrazol-1-yl)-1-methyl-indol-7-yl)-1-oxaspiro[4.4]non-3-ene-7-methanol (39.7 mg, 0.077 mmol) in dichloromethane (DCM) (2 mL) was treated with 36 mg (0.085 mmol) of Dess-Martin reagent. After one hour, the reaction was diluted with DCM, washed with 1N KOH, saturated brine solution, dried ($MgSO_4$), and evaporated. Silica gel chromatography eluting with 25% acetone/hexane afforded pure aldehyde; yield 27.4 mg. The aldehyde (0.054 mmol) in methanol (1.5 mL) was treated with 3A molecular sieves (10 mg), 2-fluoroethylamine hydrochloride (27 mg, 0.271 mmol), DIPEA (31 µL, 0.178 mmol) and sodium cyanoborohydride (7.5 mg, 0.119 mmol) for 3 hours at room temperature and then evaporated. The residue was partitioned between ethyl acetate and saturated sodium hydrogencarbonate solution. The organic layer was washed with saturated brine solution and evaporated. The title compound was obtained pure by silica gel chromatography eluting with 25% acetone/hexane; yield 16.5 mg. It was converted into its hydrochloride salt with 1M HCl in diethyl ether.

400 MHz $^1$H NMR ($CD_3OD$): δ 1.57 (m, 1H), 2.52 (dd, 1H), 2.61 (dd, 1H), 4.29 (dd, 1H), 4.38 (t, 1H), 4.49 (t, 1H), 4.73 (dd, 1H), 5.90 (m, 1H), 6.59 (d, 1H), 6.78 (d, 1H), 7.02 (t, 2H), 7.27 (d, 1H), 7.45 (m, 2H), 7.70 (d, 1H); Mass spec ($NH_3$/CI): 559 (M+1).

EXAMPLE 22

Methyl [5(R),6(S),7(S)]-6-(4-fluorophenyl)-3-(3-methoxy-6-(2-trifuoromethyl-imidazol-1-yl)-pyridin-2-yl)-1-oxa-spiro[4.4]non-3-ene-7-carboxylate (Step A: 2-Bromo-3-methoxy-6-nitropyridine To a 3-neck 500 mL round bottom flask fitted with a Teflon stir bar and a thermometer was added 37.6 g (200 mmol) of 2-bromo-3-methoxypyridine in 90 mL of concentrated sulfuric acid. Fuming nitric acid (90%) was added dropwise at a rate to keep the solution temperature at 60° C. After the addition, stirred at 60° C. for 3 h. Then 6 mL more of concentrated nitric acid was added at 60° C. TLC (7/3 hexane/ethyl acetate) showed no starting material. Poured the contents of the flask into chipped ice (1 L) with vigorous stirring. A precipitate formed and was filtered. Washed with ice water (3×200 mL) and sucked dry. Removed water under reduced pressure at 80° C. Recovered 16.5 g of product (35% yield). $^1$H NMR ($CDCl_3$, 200 MHz) δ 8.27 (d, 1H, 8 Hz), 7.32 (d, 1H, J=8 Hz), 4.06 (s, 3H) ppm.

Step B: 2-Bromo-3-methoxy-6-aminopyridine

2-Bromo-3-methoxy-6-nitropyridine (470 mg, 2.0 mmol) was added to 8 mL (3:1 water: ethanol) and 2 mL of 30% ammonium hydroxide. Added 350 mg (2 mmol) of sodium hydrosulfite ($Na_2S_sO_4$) and heated to 60° C. After 30 min, no starting material was seen. Added 50 mL of water and extracted the product with methylene chloride (2×25 mL). Dried over $MgSO_4$, filtered and reduced the volume. Flash chromatography (75/25 hexane/ethyl acetate) recovered 200 mg of product (50% yield). ¹H NMR (CDCl₃, 200 MHz) δ 7.06 (d, 1H, 10 Hz), 6.41 (d, 1H, J=10 Hz), 3.8 (s, 3H) ppm
Step C: 2-Bromo-3-methoxy-6-trifluoroacetamidopyridine The title compound was prepared by using the procedure given in Example 6, Step F (b), replacing 2-bromo-4-aminoanisole with 2-bromo-3-methoxy-6-aminopyridine (from Step B above). ¹H NMR (CDCl₃, 200 MHz) 3 7.16 (d, 1H, 10 Hz), 6.27 (d, 1H, J=10 Hz), 3.79 (s, 3H) ppm.
Step D: 2-Bromo-3-methoxy-6-(2-(trifluoromethyl) imidazol-1-yl)pyridine The title compound was prepared by using the procedure given in Example 48, Step A, replacing N-(3-bromo-4-methoxyphenyl)-trifluoroacetamide with N-(2-bromo-3-methoxy)-6-trifluoroacetamido-pyridine (from Step C above). ¹H NMR (CDCl₃, 400 MHz) δ 7.35 (m, 2H), 7.27 (m, 1H), 7.19 (s, 1H), 3.99 (s, 3H) ppm.
Step E: Methyl [5(R),6(S),7(S)]-6-(4-fluorophenyl)-3-(3-methoxy-6-(2-trifluoromethyl-imidazol-1-yl)-pyridin-2-yl)-1-oxa-spiro[4.4]non-3-ene-7-carboxylate The title compound was prepared by the procedure shown in Example 6, Step F d, except that methyl 2-(S)-(4-fluorophenyl)cyclopentanone-3-(S)-carboxylate (from Example 5) was substituted for methyl 2-(RS)-(4-fluorophenyl)cyclopentanone-3-(RS)-carboxylate in Step A along with replacing 2-bromo-4-(5-(trifluoromethyl) tetrazol-1-yl)anisole with 2-bromo-3-methoxy-6-(2-(trifluoromethyl)imidazol-1-yl)pyridine. (from Step D above). ¹H NMR (CDCl₃, 400 MHz) δ 7.21-7.27 (m, 3H), 7.14 (d, 2H, 1.5 Hz), 6.86 (t, 2H, 9 Hz), 6.67 (t, 1H, J=2 Hz), 4.65 (dd, 1H J=13 Hz, J=2 Hz), 4.19 (dd, 1H J=13 Hz, J=2 Hz), 3.98 (s, 3H), 3.56 (s, 3H), 3.45 (m, 1H), 3.32 (d, 1H, J-14 Hz), 2.35–2.42 (m, 1H), 2.19–2.28 (m, 1H), 2.05–2.15 (m, 1H), 1.94–2.03 (m, 1H) ppm. Mass Spectrum (NH₃-CI): m/z 518 (M+H, 100%).

EXAMPLE 23

Methyl [5(R),6(S),7(S)]-6-(4-fluorophenyl)-3-[3-methoxy-6-(2-trifluoromethyl-imidazol-1-yl)-pyridin-2-yl]-1-oxa-spiro[4.4]non-2-ene-7-carboxylate The title compound was prepared as the higher R_f of two products obtained using the procedure given in Example 6, Step G, except that 40 mg of methyl [5(R),6(S),7(S)]-6-(4-fluorophenyl)-3-(3-methoxy-6-(2-trifluoromethylimidazol-1-yl)-pyridin-2-yl)-1-oxa-spiro[4.4]non-3-ene-7-carboxylate (Example 1 (IEK)) was substituted in place of methyl [3-(SR), 5-(RS), 6-(SR), 7-(SR)]-6-(4-fluorophenyl)-3-2-methoxy-5-((5-(trifluoromethyl)tetrazol-1-yl)phenyl)- 1-oxaspiro[4.4]non-3-ene-7-carboxylate. After flash chromatography (60/40 hexane/ethyl acetate) 10.2 mg of higher R_f product was recovered. ¹H NMR (CDCl₃, 400 MHz) δ 7.2–7.3 (m, 3H), 7.05–7.14 (m, 2H,), 6.8–6.9 (m, 3H), 4.47–4.60 (m, 2H), 4.1 (m, 1H), 3.56 (s, 3H), 3.3–3.4 (m, 1H), 3.1–3.25 (m, 1H), 3.0 (s, 1H), 2.35–2.42 (m, 1H), 1.9–2.2 (m, 2H) ppm. Mass Spectrum (NH₃-CI): m/z 518 (M+H, 100%).

EXAMPLE 24

Methyl [3(S),5(R),6(S),7(S)]-6-(4-fluorophenyl)-3-[3-methoxy-6-(2-trifluoromethylimidazol-1-yl)-pyridin-2-yl]-1-oxa-spiro [4.4]nonane-7-carboxylate The title compound was prepared as the lower R_f of two products obtained using the procedure in Example 6, Step G, except that 40 mg of methyl [5(R),6(S),7(S)]-6-(4-fluorophenyl)-3-(3-methoxy-6-(2-trifluoromethyl-imidazol-1-yl)-pyridin-2-yl)-1-oxa-spiro[4.4]non-3-ene-7-carboxylate (Example 22) was substituted in place of methyl [3-(SR), 5-(RS), 6-(SR), 7-(SR)]-6-(4-fluorophenyl)-3-2-methoxy-5-((5-trifluoromethyl)tetrazol-1-yl)phenyl)-1-oxaspiro[4.4]non-3-ene-7-carboxylate. After flash chromatography (60/40 hexane/ethyl acetate) 11.5 mg of lower R_f product was obtained. ¹H NMR (CDCl₃, 400 MHz) δ 7.40 (dd, 2H, J=10 Hz, J=6 Hz), 7.17 (d, 1H, 1.3 Hz), 7.10 (d, 2H, J=5 Hz), 7.07 (d, 1H, J=1 Hz), 6.87 (t, 2H, 9 Hz), 4.07–4.12 (m, 2H) 3.92 (s, 3H), 3.54 (s, 3H), 3.3 (m, 1H), 3.1–3.2 (m, 2H), 2.25–2.32 (m, 2H), 2.10–2.20 (m, 2H), 1.9–2.0 (m, 1H) ppm. Mass Spectrum (NH₃-CI): m/z 520 (M+H, 100%).

EXAMPLE 25

[5(R),6(S),7(S)]-6-(4-Fluorophenyl)-3-[3-methoxy-6-(2-trifluoromethyl-imidazol-1-yl)pyridin-2-yl]-1-oxa-spiro[4.4]non-3-en-7-methanol The title compound was prepared using the procedure given in Example 10, Step A, except that 52 mg of methyl [5(R),6(S),7(S)]-6-(4-fluorophenyl)-3-(3-methoxy-6-(2-trifluoromethyl-imidazol-1-yl)-pynrdin-2-yl)-1-oxa-spiro [4.4]non-3-ene-7-carboxylate (from Example 22) was substituted for methyl [3-(S), 5-(R), 6-(S), 7-(S)]-6-(4-fluorophenyl)-3-(2-methoxy-5-((5-trifluoromethyl)-tetrazol-1-yl)phenyl)-1-oxaspiro[4.4]nonane-7-carboxylate carboxylate (from Example 9). After flash chromatography (60/40 methylene chloride/ethyl acetate) 43 mg of product was obtained. ¹H NMR (CDCl₃, 400 MHz) δ 7.2–7.3 (m, 4H), 7.15 (d, 2H, 9 Hz), 6.88 (t, 2H, J=9 Hz), 6.68 (t, 1H, 2 Hz), 4.85 (dd, 1H, J=12 Hz, J=2 Hz), 4.22 (dd, 1H, J=12 Hz, J=2 Hz), 4.2 (m, 1H), 3.94 (s, 3H), 3.64 (dd, 1H, J=12 Hz, J=6 Hz), 3.50 (dd, 1H, J=12 Hz, J=6 Hz), 2.82 (d, 1H J=14 Hz), 2.75 (m, 1H), 2.02–2.25 (m, 3H), 1.3 (m, 1H) ppm. Mass Spectrum (NH₃-CI): m/z 490 (M+H, 100%).

EXAMPLE 26

[5(R),6(S),7(S)]-6-(4-Fluorophenyl)-3-[3-methoxy-6-(2-trifluoromethyl imidazol-1-yl)-pyridin-2-yl]-1-oxa-spiro[4.4]non-3-en-7-amine
(Step A: [5(R),6(S),7(S)]-6-(4-Fluorophenyl)-3-[3-methoxy-6-(2-trifluoromethyl-imidazol-1-yl)-pyridin-2-yl]-1-oxa-spiro[4.4]non-3-ene-7-carbonyl hydrazoic acid To a solution of 350 mg (0.68mmol) of methyl [5(R),6 (S),7(S)]-6-(4-fluorophenyl)-3-(3-methoxy-6-(2-trifluoromethyl-imidazol-1-yl)-pyridin-2-yl)-1-oxa-spiro [4.4]non-3-ene-7-carboxylate (Example 22) in 1 mL of ethanol is added 43 mg of hydrazine hydrate (1.35 mmole). The mixture is refluxed with stirring for 8 hours, during which 2 more equivalents of hydrazine hydrate are added. Solvent and excess reagent are removed under reduced pressure. The product is flash chromatographed using 95/5 methylene chloride/methanol to give 220 mg of product. ¹H NMR (CDCl₃, 200 MHz) δ 7.1–7.3 (m, 4H), 7.15 (d, 2H, 9 Hz), 6.8–6.9(m, 2H), 6.68 (t, 1H, 2 Hz), 4.87 (dd, 1H, J=12 Hz, J=2 Hz), 4.31 (dd, 1H, J=12 Hz, J=2 Hz), 3.95 (s, 3H), 3.7–3.9 (m, 2H), 3.35 (d, 1H, J=12 Hz), 3.0–3.2 (m, 2H), 2.02–2.4 (m, 3H) ppm.
Step B: [5(R),6(S),7(S)]-6-(4-Fluorophenyl)-3-[3-methoxy-6-(2-trifluoromethyl-imidazol-1-yl)-pyridin-2-yl]-1-oxa-spiro[4.41]non-3-ene-7-carbonyl azide The hydrazoic acid from Example 26, Step A is dissolved with 5 mL of 2 N HCl and 2 mL of ethanol in a 10 mL round bottom flask. Cool to 4° C. and add 5 equivalents (220 mg, 3.4 mmol) of sodium azide portionwize over 10 minutes with with vigorous stirring to break up frothing of the solution due to N₂O₄ evolution. After 1 hr, add saturated sodium bicarbonate (pH=7). Remove the solvents under reduced pressiue. The product is flash chromatographed using 95/5 methylene chloride/methanol to give 140 mg of product. ¹H NMR (CDCl₃, 400 MHz) δ 7.2–7.3 (m, 4H), 7.13–7.20 (m, 2H), 6.9 (t, 2H, 8 Hz), 6.68 (s, 1H), 4.82 (d, 1H, J=12 Hz), 4.20 (d, 1H, J=12 Hz), 3.95 (s, 3H), 3.8–3.9 (m, 1H), 2.66 (d, 1H, J=12 Hz), 2.2–2.35 (m, 2H), 2.0–2.1 (m, 1H), 0.95–1.1 (m, 1H) ppm.

Step C: [5(R),6(S),7(S)]-6-(4-Fluorophenyl)-3-[3-methoxy-6-(2-trifluoromethylimidazol-1-yl)-pyridin-2-yl]-1-oxa-spiro[4.4]non-3-en-7-amine To a 10 mL round bottom flask fitted with a stirred bar and reflux condenser is added the carbonyl azide from Example 26, Step B to 3 mL of 35% acetic acid. The solution is refluxed until nitrogen evolution has ceased. The solvents are removed under reduced pressure and the residue chromatographed by flash chromatography using gradient elution (97/3 to 90/10 methylene chloride/methanol). Recovered 90 mg of product. ¹H NMR (CDCl₃, 400 MHz) δ 7.2–7.3 (m, 4H), 7.12–7.20 (m, 2H), 6.9 (t, 2H, 8 Hz), 6.68 (s, 1H), 4.82 (dd, 1H J=12, Hz, J=2 Hz), 4.20 (dd, 1H J=12, Hz, J=2 Hz), 3.95 (s, 3H), 3.8–3.9 (m, 1H), 2.66 (d, 1H, J=12 Hz), 2.2–2.35 (m, 2H), 2.0–2.1 (m, 1H), ),1.85–2.0 (bs, 2H), 0.95–1.1 (m, 1H) ppm. Mass Spectrum (NH₃-CI): m/z 475 (M+H, 100%).

EXAMPLE 27

[5(R),6(S),7(S)]-6-(4-Fluorophenyl)-3-[3-methoxy-6-(2-trifluoromethyl imidazol-1-yl)-pyridin-2-yl]-1-oxa-spiro[4.4]non-3-en-7-methylamine ( To 60 mg (0.126 mmol) of [5(R),6(S),7(S)]-6-(4-fluorophenyl)-3-[3-methoxy-6-(2-trifluoromethylimidazol-1-yl)-pyridin-2-yl]-1-oxa-spiro[4.4]non-3-en-7-amine (Example 26 Step C) in 2 mL of methanol in a 10 mL round bottom flask fitted with a stir bar and rubber septum was added 15 mg of metallic sodium. After the sodium has dissoved, 10 mg of paraformadehyde was added and the solution was stirred at 30° C. Sodium borohydride (10 mg, 3 eq) was added portionwise until starting material was gone by TLC (2 hr). The product was flash chromatographed using 95/5 methylene chloride/methanol to give 35 mg of product (53% yield). ¹H NMR (CDCl₃, 400 MHz) δ 7.2–7.3 (m, 4H), 7.12–7.20 (m, 2H), 6.87 (t, 2H, 8 Hz), 6.68 (s, 1H), ), 4.82 (dd, 1H J=12 Hz, J=2 Hz), 4.20 (dd, 1H J=12 Hz, J=2 Hz), 3.96 (s, 3H), 3.75–3.85 (m, 1H), 3.30 (d, 1H, J=12 Hz), 2.4–2.55 (m, 2H), 2.35 (s, 3H), 2.1–2.2 (m, 2H), ),1.85–2.0 (bs, 1H), ppm. Mass Spectrum (NH₃-CI): m/z 489 (M+H, 100%).

EXAMPLE 28

[3(S),5(R),6(S),7(S)]-6-(4-fluorophenyl)-3-[3-methoxy-6-(2-trifluoromethylimidazol-1-yl)-pyridin-2-yl]-1-oxa-spiro[4.4]non-7-yl-methylamine (The title compound was prepared using the procedure given in Example 6, Step G, except that 25 mg of [5(R),6(S),7(S)]-6-(4-fluorophenyl)-3-[3-methoxy-6-(2-trifluoromethylimidazol-1-yl)-pyridin-2-yl]-1-oxa-spiro[4.4]non-3-en-7-methylamine (from Example 27) was substituted in place of methyl [3-(SR), 5-(RS), 6-(SR), 7-(SR)]-6-(4-fluorophenyl)-3-2-methoxy-5-((5-trifluoromethyl)tetrazol-1-yl)phenyl)-1-oxaspiro[4.4]nonane-7-carboxylate. The product was flash chromatographed using 94/6 methylene chloride/methanol to give 7 mg of product (35% yield). ¹H NMR (CDCl₃, 400 MHz) δ 7.28–7.35 (m, 2H), 7.15 (d, 1H, J=3 Hz), 7.125 (d, 2H, J=6 Hz), 7.07 (s, 1H), 6.91 (t, 2H, 9 Hz), 4.01 (t, 1H J=6 Hz), 3.81 (s, 3H), 3.75–3.85 (m, 1H), 3.65– 3.75 (m, 1H), 3.1–3.23 (m, 2H), 2.8–3.2(bs, 1H), 2.3–2.5 (m, 1H), 2.33 (s, 3H), 2.1–2.2 (m, 4H), 1.85–1.95 (m, 1H) ppm. Mass Spectrum (NH₃-CI): mz 491 (M+H, 100%).

EXAMPLE 29

[3(S),5(R),6(S),7(S)]-6-(4-Fluorophenyl)-3-[3-methoxy-6-(2-trifluoromethyl-imidazol-1-yl)-pyridin-2-yl]-1-oxa-spiro[4.4]non-7-yl-methanol (The title compound was prepared using the procedure given in Example 6, Step G, except that 150 mg of [5(R), 6(S),7(S)]-6-(4-fluorophenyl)-3-[3-methoxy-6-(2-trifluoromethyl-imidazol-1-yl)pyridin-2-yl]-1-oxa-spiro[4.4]non-3-en-7-methanol (from Example 25) was substituted in place of methyl [3-(SR), 5-(RS), 6-(SR), 7-(SR)]-6-(4-fluorophenyl)-3-2-methoxy-5-((5-trifluoromethyl)tetrazol-1-yl)phenyl)-1-oxaspiro[4.4]nonane-7-carboxylate. The product was flash chromatographed using 60/40 methylene chloride/ethyl acetate to give 74 mg of product (50% yield). ¹H NMR (CDCl₃, 400 MHz) δ 7.28–7.32 (m, 2H), 7.17 (d, 1H, J=3 Hz), 7.125 (s, 2H), 7.08 (s, 1H), 6.89 (t, 2H, 9 Hz), 4.05 (t, 1H, J=6 Hz), 3.80 (s, 3H), 3.75–3.80 (m, 1H), 3.65 (dd, 1H, J=18 Hz, J=4 Hz), 3.48 (dd, 1H, J=18 Hz, J=4 Hz), 3.12 (dd, 1H, J=10 Hz, J=2 Hz), 2.6–2.7(m, 2H), 2.28 (t, 1H, J=12 Hz), 2.05–2.20 (m, 3H), 1.85–1.95 (m, 1H), 1.79 (m, 1H) ppm. Mass Spectrum (NH₃-CI): m/z 492 (M+H, 100%).

EXAMPLE 30

[3(S),5(R),6(S),7(S)]-6-(4-Fluorophenyl)-3-[3-methoxy-6-(2-trifluoromethyl-imidazol-1-yl)-pyridin-2-yl]-1-oxa-spiro[4.4]non-7-ylmethyl-dimethyl-amine (Step A: [3(S),5(R),6(S),7(S)]-6-(4-Fluorophenyl)-3-[3-methoxy-6-(2-trifluoromethyl-imidazol-1-yl)-pyridin-2-yl]-1-oxa-spiro[4.4]nonane-7-carbaldehyde A solution of [3(S),5(R),6(S),7(S)]-6-(4-fluorophenyl)-3-[3-methoxy-6-(2-trifluoromethyl-imidazol-1-yl)-pyridin-2-yl]-1-oxa-spiro[4.4]non-7-yl-methanol (from Example 7) in CH₂Cl₂ was treated with Dess-Martin reagent. After 40 min, the reaction was quenched with 1.0 mL of 1.0 N KOH. The resulting mixture was partitioned between of ether and H₂O. The layers were separated and the organic layer was washed with H₂O, and sat'd NaCl, dried over MgSO₄ and concentrated in vacuo. The product was flash chromatographed using 60/40 hexane/ethyl acetate to give 40 mg of product (65% yield). ¹H NMR (CDCl₃, 400 MHz) δ 9.62 (d, 1H, J=2 Hz), 7.31 (dd, 2H, J=9 Hz, J=4.5 Hz), 7.19 (d, 1H, J=3 Hz), 7.17(d, 2H, J=Hz), 7.09 (d, 1H, J=1.5 Hz), 6.90 (t, 2H, 9 Hz), 4.05 (t, 1H, J=6 Hz), 3.81 (s, 2H), 3.85–3.90 (m, 1H), 3.35 (m, 1H), 3.1–3.2 (m, 3H), 2.32(t, 1H, J=18 Hz), 2.1–2.25 (m, 3H), 2.0–2.07 (m, 1H), 1.7–1.75 (m, 1H) ppm.

Step B: [3(S),5(R),6(S),7(S)]-6-(4-Fluoro-phenyl)-3-[3-methoxy-6-(2-trifluoromethyl-imidazol-1-yl)-pyridin-2-yl]-1-oxa-spiro[4.41]non-7-yl-methyl-dimethylamine The title compound was prepared using standard reductive amination conditions, using40 mg of [3(S),5(R),6(S),7 (S)]-6-(4-fluorophenyl)-3-[3-methoxy-6-(2-trifluoromethyl-imidazol-1-yl)-pyridin-2-yl]-1-oxa-spiro[4.4]nonane-7-carbaldehyde (from Example 30 Step A) and dimethylamine hydrochloride. The product was flash chromatographed using (97/3/0.2) methylene chloride/methanol/ammonium hydroxide) to give 18 mg of product (42% yield). ¹H NMR (CDCl$_3$, 400 MHz) δ 7.25 (m, 2H), 7.19 (d, 1H, J=3 Hz), 7.13(d, 2H, J=Hz), 7.09 (d, 1H, J=1.5 Hz), 6.89 (t, 2H, 9 Hz), 4.03 (t, 1H, J=6 Hz), 3.81 (s, 3H), 3.80–3.90 (m, 1H), 3.1–3.2 (dd, 1H, J-18 Hz, J=5 Hz), 2.55–2.65 (m, 1H), 2.45 (d, 1H, J=16 Hz), 2.1–2.3 (m, 3H), 2.14(s, 6H), 2.05–2.10 (m, 3H), 1.85–1.92 (m, 1H), 1.45–1.55 (m, 1H) ppm. Mass Spectrum (NH$_3$-CI): m/z 519 (M+H, 100%).

EXAMPLE 31

Methyl [5(R),6(S),7(S)]-6-(4-fluoro-phenyl)-3-[3-hydroxy-6-(2-trifluoromethyl-imidazol-1-yl)-pyridin-2-yl]-1-oxa-spiro[4.4]non-3-ene-7-carboxylate (Step A: 2-Bromo-3-hydroxy-6-(2-(trifluoromethyl) imidazol-1-yl)pyridine The title compound was prepared by taking 620 mg (1.9 mmol) of 2-bromo-3-methoxyoxy-6-(2-(trifluoromethyl) imidazol-1-yl)pyridine (described in Example 22 Step D) and heating it at 160° C. in 2.0 gm (15.7 mmole) of anhydrous pyridinium hydrochloride under nitrogen for 3 hours. By TLC (70/30 hexane/ethyl acetate) no starting material was seen. The pyridine hydrochloride was removed by sublimation under high vacuum at 130° C. The product remained in the flask and was dissolved in 2 mL of methanol. This was slowly dropped into 150 mL of ice water with stirring. The product precipitated out of solution and was filtered off. Recovered 350 mg of product (55% yield). $^1$H NMR (CDCl$_3$, 400 MHz) δ 7.50 (d, 2H, J=8 Hz), 7.33 (s, 1H), 7.31 (d, 1H, J=8 Hz), 7.21 (s, 1H), ppm.
Step B: Methyl [5(R),6(S),7(S)]-6-(4-fluorophenyl)-3-(3-hydroxy-6-(2-trifluoromethyl-imidazol-1-yl)-pyridin-2-yl)-1-oxa-spiro[4.4]non-3-ene-7-carboxylate The title compound was prepared by using the procedure given in Example 6, Step F d, except that 270 mg of methyl 2-(S)-(4-fluorophenyl)cyclopentanone-3-(S)-carboxylate (from Example 5) was substituted for methyl 2-(RS)-(4-fluorophenyl)cyclopentanone-3-(RS)-carboxylate along with replacing 2-bromo-4-(5-(trifluoromethyl)-tetrazol-1-yl)anisole with 170 mg of 2-bromo-3-hydroxy-6-(2-(trifluoromethyl)imidazol-1-yl)pyridine.(from Example 31 Step A). The product was flash chromatographed using 95/5 methylene chloride/methanol to give 47 mg of product (middle R$_f$ spot of three products obtained (high, middle and low R$_f$ material)) (26% yield). $^1$H NMR (CDCl$_3$, 400 MHz) δ 7.21–7.27 (m, 3H), 7.16 (d, 1H, 1.5 Hz), 7.03 (d, 1H, 7 Hz), 6.80 (m, 3H), 4.90 (dd, 1H, J=13 Hz, J=2 Hz), 4.28 (dd, 1H, J=13 Hz, J=2 Hz), 3.63 (s, 3H), 3.50–3.60 (m, 1H), 3.49 (s, 1H), 3.38 (d, 1H, J-14 Hz), 2.35–2.5 (m, 3H), 2.15–2.25 (m, 1H), 1.94–2.03 (m, 1H) ppm. Mass Spectrum (NH$_3$-CI): m/z 504 (M+H, 100%).

EXAMPLE 32

Methyl [5(R),6(S),7(S)]-3-[3-difluoromethoxy-6-(2-trifluoromethyl-imidazol-1-yl)-pyridin-2-yl]-6(4-fluorophenyl)-1-oxa-spiro [4.4]non-3-ene-7-carboxylate (The title compound was prepared by dissolving 40 mg (0.08 mmol) of methyl [5(R),6(S),7(S)]-6-(4-fluorophenyl)-3-(3-hydroxy-6-(2-trifluoromethyl-imidazol-1-yl)-pyridin-2-yl)-1-oxa-spiro[4.4]non-3-ene-7-carboxylate (from Example 31, Step B) in 1 mL of dimethylformamide in a 5 mL round bottom flask. Added 10 mg (0.25 mmol) of sodium hydroxide and 15 mg (0.16 mmol) of difluoroacetic acid. By TLC a higher R$_f$ product (50/50 hexane/ethyl acetate) was observed. The methyl ester was not hydrolyzed under these conditions. The reaction mixture was poured into cold water (10 mL) and extracted with methylene chloride. The organic layer was dried over anhydrous magnesium sulfate, filtered and the solvent removed under reduced pressure. The residue was flash chromatographed (70/30 hexane/ethyl acetate) and 22 mg of product was isolated (55% yield). $^1$H NMR (CDCl$_3$, 400 MHz) δ 7.60 (d, 1H, J=9 Hz), 7.20–7.23 (m, 5H), 6.89 (t, 2H, J=9 Hz), 6.70 (d,1H, J=1.5 Hz), 6.51 (t, F$_2$-H coupling, 1H, J=71 Hz), 4.89 (dd, 1H, J=13 Hz, J=2 Hz), 4.22 (dd, 1H, J=13 Hz, J=2 Hz), 3.56 (s, 3H), 3.40–3.50 (m, 1H), 3.35 (d, 1H, J=12 Hz), 3.38 (d, 1H, J-14 Hz), 2.35–2.42 (m, 1H), 2.2–2.30 (m, 1H), 2.1–2.17 (m, 1H), 1.94–2.03 (m, 1H) ppm. Mass Spectrum (NH$_3$-CI): m/z 554 (M+H, 100%).

EXAMPLE 33

[3(R),5(R),6(S),7(S)]-6-(4-Fluorophenyl)-3-[3-methoxy-6-(2-trifluoromethyl-imidazol-1-yl)-pyridin-2-yl]-1-oxa-spiro[4.4]non-7-yl}-methanol (Step A: [5(R),6(S),7(S)]-6-(4-Fluorophenyl)-3-[3-methoxy-6-(2-trifluoromethyl-imidazol-1-yl)-pyridin-2-yl]-1-oxa-spiro[4.41]non-2-en-7-yl}-methanol The title compound was prepared using the procedure given in Example 6, Step G, except that 98 mg of [5(R),6(S),7(S)]-6-(4-fluorophenyl)-3-[3-methoxy-6-(2-trifluoromethyl-imidazol-1-yl)pyridin-2-yl]-1-oxa-spiro [4.4]non-3-en-7-methanol (from Example 4 (IEK)) was substituted in place of methyl [3-(SR), 5-(RS), 6-(SR), 7-(SR)]-6-(4-fluorophenyl)-3-2-methoxy-5-((5-trifluoromethyl)tetrazol-1-yl)phenyl)-1-oxaspiro[4.4] nonane-7-carboxylate and no hydrogen gas was used in the experimental procedure. Recovered 39 mg (0.08 mmol) of enol ether product plus 10 mg of fully saturated spiroether. This material was take through,without characterization, to the next step
Step B: [3(S),5(R),6(S),7(S)]-6-(4-Fluorophenyl)-3-[3-methoxy-6-(2-trifluoromethyl-imidazol-1-yl)-pyridin-2-yl]-1-oxa-spiro[4.4]non-2-en-7-yl}-methanol-trifluoroacetate and [(3R),5(R),6(S),7(S)]-6-(4-fluorophenyl)-3-[3-methoxy-6-(2-trifluoromethyl-imidazol-1-yl)-pyridin-2-yl]-1-oxa-spiro[4.4]non-2-en-7-yl}-methanol-trifluoroacetate The title compounds were prepared as a mixture of two diasteriomeric trifluoromethyl acetates by taking 35 mg (0.07 mmol) of [5(R),6(S),7(S)]-6-(4-Fluorophenyl)-3-[3-methoxy-6-(2-trifluoromethyl-imidazol-1-yl)-pyridin-2-yl]-1-oxa-spiro[4.4]non-2-en-7-yl}-methanol (from Example 32 Step A) and treating it with 25 mg (0.2 mmole) of triethylsilane in 1 mL of trifluoroacetic acid at room temperature overnight. The solvents were removed by reduced pressure and two products were observed by TLC (60/40 hexane/ethyl acetate). The products were separated by flash chromatography (60/40 hexane/ethyl acetate). We isolated 8 mg of higher R$_f$ and 5 mg of lower R$_f$ material. Hydrolysis of the lower R$_f$ 7-trifluoroacetate ester material with triethyl amine in methanol gave the fully reduced derivative which corresponded in every way by 400 MHz NMR to the fully reduced product [3(S),5(R),6(S),7(S)]-6-(4-fluorophenyl)-3-[3-methoxy-6-(2-trifluoromethyl-imidazol-1-yl)-pyridin-2-yl]-1-oxa-spiro [4.4]non-7-yl-methanol.
Step C: [(3R),5(R),6(S),7(S)]-6-(4-Fluorophenyl)-3-[3-methoxy-6-(2-trifluoromethyl-imidazol-1-yl)-pyridin-2-yl]-1-oxa-spiro[4.4]non-2-en-7-yl}-methanol The higher R$_f$ material (8 mg) isolated in Example 33 Step B was hydrolyzed in 1 mL of methanol with 20 micoliters of triethylamine for 1 hr. The solvent and triethyl amine was removed under reduced pressure and 5 mg of [(3R),5(R),6(S),7(S)]-6-(4-fluorophenyl)-3-[3-methoxy-6-(2- trifluoromethyl-imidazol-1-yl)-pyridin-2-yl]-1-oxa-spiro [4.4]non-2-en-7-yl}-methanol was isolated. ¹H NMR (CDCl₃, 400 MHz) δ 7.15–7.25 (m, 3H), 7.1–7.14 (m, 2H), 6.9–7.0 (m, 3H), 5.6 (bs, 1H (OH), 3.8 (d, 2H, J=5 Hz), 3.68 (s, 3H), 3.63 (d, 2H J=5 Hz), 3.48–3.52 (m, 1H), 2.55–2.65 (m, 1H), 2.3–2.45 (m, 2H), 1.85–1.95 (m, 1H), 1.79 (m, 1H) ppm. Mass Spectrum (NH₃-CI): m/z 492 (M+H, 100%).

EXAMPLE 34

Methyl [5(R),6(S),7 (S)]-6-(4-fluoro-phenyl)-3-[3-isopropoxy-6-(2-trifluoromethyl-imidazol-1-yl)-pyridin-2-yl]-1-oxa-spiro[4.4]non-3-ene-7-carboxylate (Step A: 2-Bromo-3-isopropoxy-6-(2-(trifluoromethyl) imidazol-1-yl)pyridine The compound was prepared by taking 2-bromo-3-hydroxy-6-(2-(trifluoromethyl)imidazol-1-yl)pyridine (330 mg, 1.1 mmol from Example 31 Step B), dissolving it in 2 mL of dimethylformamide, then adding 1 g of anhydrous potassium carbonate (7 mmol) and 2-iodopropane (640 mg, 4.0 mmol) to the solution. The mixture was stirred at room temperature overnight. The next day no starting material was seen by TLC (70/30 hexane/ethyl acetate). The reaction was worked up by removing the solvent under reduced pressure and purifying the residue by flash chromatography (70/30 hexane/ethyl acetate). Recovered 180 mg of product (47% yield). ¹H NMR (CDCl₃, 400 MHz) ¹H NMR (CDCl₃, 400 MHz) δ 7.35 (d, 1H, J=1 Hz), 7.32 (s, 1H), 7.30 (s, 1H), 7.19 (d, 1H, J=1 Hz), 4.63 (sept, 1H, J=6 Hz), 1.43 (d, 6H), J=6 Hz) ppm.

Step B: Methyl [5(R),6(S),7(S)]-6-(4-fluoro-phenyl)-3-[3-isopropoxy-6-(2-trifluoromethyl-imidazol-1-yl)-pyridin-2-yl]-1-oxa-spiro[4.4]non-3-ene-7-carboxylate The title compound was prepared by using the procedure given in Example 6, Step F d, except that methyl 2-(S)-(4-fluorophenyl)cyclopentanone-3-(S)-carboxylate (from Example 5) was substituted for methyl 2-(RS)-(4-fluorophenyl)cyclopentanone-3-(RS)-carboxylate in Step A along with replacing 2-bromo-4-(5-(trifluoromethyl) tetrazol-1-yl)anisole with 180 mg (0.51 mmol) of 2-bromo-3-isopropoxy-6-(2-(trifluoromethyl)imidazol-1-yl)pyridine. (from Example 34 Step A). Recovered 220 mg of product (80% yield, TLC 60/40 hexane/ethyl acetate) (CDCl₃, 400 MHz) δ 7.21–7.27 (m, 3H), 7.14 (d, 2H, 1.5 Hz), 6.86 (t, 2H, 9 Hz), 6.67 (t, 1H, J=2 Hz), 4.88 (dd, 1H, J=13 Hz, J=2 Hz), 4.63 (sept, 1H, J=6 Hz), 4.20 (dd, 1H J=13 Hz, J=2 Hz), 3.56 (s, 3H), 3.45 (m, 1H), 3.32 (d, 1H, J-14 Hz), 2.35–2.42 (m, 1H), 2.2–2.27 (m, 1H), 2.05–2.15 (m, 1H), 1.94–2.03 (m, 1H), 1.42 (d, 3H, J=6), 1.40 (d, 3H, J=6) ppm. Mass Spectrum (NH₃-CI): m/z 546 (M+H, 100%).

EXAMPLE 35

Methyl [5(R),6(S),7(S)]-6-(4-fluorophenyl)-3-[3-isopropoxy -6-(2-trifluoromethyl-imidazol-1-yl)-pyridin-2-yl]-1-oxa-spiro[4.4]non-2-ene-7-carboxylate (The title compound was prepared as the higher $R_f$ of two products obtained using the procedure given in Example 6, Step G, except that 180 mg of methyl [5(R),6(S),7(S)]-6-(4-fluorophenyl)-3-(3-isopropoxy-6-(2-trifluoromethylimidazol-1-yl)-pyridin-2-yl)-1-oxa-spiro [4.4]non-3-ene-7-carboxylate (Example 34 Step B) was substituted in place of methyl [3-(SR), 5-(RS), 6-(SR), 7-(SR)]-6-(4-fluorophenyl)-3-2-methoxy-5-((5-trifluoromethyl)tetrazol-1-yl)phenyl)-1-oxaspiro[4.4] nonane-7-carboxylate. After flash chromatography (95/5 methylene chloride/ethyl acetate) we recovered 40 mg of higher $R_f$ product. ¹H NMR (CDCl₃, 400 MHz) δ 7.2–7.3 (m, 3H), 7.05–7.14 (m, 2H,), 6.8–6.9 (m, 3H), 4.47–4.60 (m, 2H), 4.1 (m, 1H), 3.80 (m, 1H), 3.56 (s, 3H), 3.54 (s, 1H), 3.1–3.4 (m, 2H), 3.0 (s, 1H), 2.35–2.42 (m, 1H), 1.9–2.2 (m, 1H), 1.3–1.4 (m, 6H) ppm. Mass Spectrum (NH₃-CI): m/z 546 (M+H, 100%).

EXAMPLE 36

Methyl [3(S),5(R),6(S),7(S)]-6-(4-fluorophenyl)-3-[3-isopropoxy-6-(2-trifluoromethylimidazol-1-yl)-pyridin-2-yl]-1-oxa-spiro[4.4]nonane-7-carboxylate The title compound was prepared as the lower $R_f$ of two products obtained using the procedure given in Example 6, Step G, except that 180 mg of methyl [5(R),6(S),7(S)]-6-(4-fluorophenyl)-3-(3-isopropoxy-6-(2-trifluoromethyl-imidazol-1-yl)-pyridin-2-yl)-1-oxa-spiro[4.4]non-3-ene-7-carboxylate (Example34 Step B) was substituted in place of methyl [3-(SR), 5-(RS), 6-(SR), 7-(SR)]-6-(4-fluorophenyl)-3-2-methoxy-5-((5-trifluoromethyl)tetrazol-1-yl)phenyl)-1-oxaspiro[4.4]nonane-7-carboxylate. After flash chromatography (95/5 methylene chloride/ethyl acetate) we recovered 115 mg of lower $R_f$ product. ¹H NMR (CDCl₃, 400 MHz) δ 7.30 (dd, 2H,J=10 Hz, J=6 Hz), 7.17 (d, 1H, 1.3 Hz), 7.10 (d, 2H, J=5 Hz), 7.07 (d, 1H, J=1 Hz), 6.87 (t, 2H, 9 Hz), 4.50 (sept, 1H, J=6 Hz), 4.07–4.12 (m, 2H), 3.92 (s, 3H), 3.54 (s, 3H), 3.3 (m, 1H), 3.1–3.2 (m, 2H), 2.25–2.32 (m, 2H), 2.10–2.20 (m, 2H), 1.9–2.0 (m, 1H), 1.23 (d, 3H, J=6), 1.21 (d, 3H, J=6) ppm. Mass Spectrum (NH₃-CI): m/z 548 (M+H, 100%).

EXAMPLE 37

[3(S),5(R),6(S),7(S)]-6-(4-Fluorophenyl)-3-[3-isopropoxy-6-(2-trifluoromethyl-imidazol-1-yl)-pyridin-2-yl]-1-oxa-spiro[4.4]non-7-ylmethyl-dimethylamine Step A: [3(S),5(R),6(S),7(S)]-6-(4-Fluorophenyl)-3-[3-isopropoxy-6-(2-trifluoromethyl-imidazol-1-yl)pyridin-2-yl]-1-oxa-spiro[4.4]non-7-yl-methanol The title compound was prepared by using the standard reduction procedures with 1.5 M DIBALH solution in toluene, using 110 mg of methyl [3(S),5(R),6(S),7(S)]-6-(4-fluorophenyl)-3-[3-isopropoxy-6-(2-trifluoromethylimidazol-1-yl)-pyridin-2-yl]-1-oxa-spiro [4.4]nonane-7-carboxylate (from Example 36). After flash chromatography (70/30 hexane/ethyl acetate) we recovered 76 mg of product(70% yield). ¹H NMR (CDCl₃, 400 MHz) δ 7.29 (dd, 2H, J=7 Hz, J=2 Hz), 7.17 (d, 1H, J=3 Hz), 7.05–7.12 (m, 3H), 6.89 (t, 2H, 9 Hz), 4.50 (sept, 1H, J=6 Hz), 4.10 (t, 1H J=8 Hz), 3.75–3.83 (m, 1H), 3.65 (dd, 1H, J=18 Hz, J=4 Hz), 3.48 (dd, 1H, J=18 Hz, J=4 Hz), 3.08 (dd, 1H, J=10 Hz, J=2 Hz), 2.6–2.7 (m, 2H), 2.32 (t, 1H, J=11 Hz), 2.05–2.20 (m, 3H), 1.85–1.95 (m, 1H), 1.65 (m, 2H), 1.31 (d, 3H, J=6), 1.30 (d, 3H, J=6) ppm Step B: [3(S),5(R),6(S),7(S)]-6-(4-Fluoro-phenyl)-3-[3-isopropoxy-6-(2-trifluoromethyl-imidazol-1-yl)-pyridin-2-yl]-1-oxa-spiro[4.4]nonane-7-carbaldehyde The title compound was prepared using the standard procedure for oxidation with Dess-Martin reagent, using 82 mg (0.16 mmol) of [3(S),5(R),6(S),7(S)]-6-(4-fluorophenyl)-3-[3-isopropoxy-6-(2-trifluoromethyl-imidazol-1-yl)pyridin-2-yl]-1-oxa-spiro[4.4]non-7-yl-methanol (from Example 37 Step A). The product was flash chromatographed using 75/25 hexane/ethyl acetate to give 41 mg of product (50% yield). $^1$H NMR (CDCl$_3$, 400 MHz) δ 7.25 (m, 2H), 7.19 (d, 1H, J=3 Hz), 7.13(d, 2H, J=Hz), 7.09 (d, 1H, J=1.5 Hz), 6.89 (t, 2H, 9 Hz), 4.50 (sept, 1H, J=6 Hz), 4.10 (t, 1H, J=6 Hz), 3.80–3.90 (m, 1H), 3.3–3.4 (m, 1H), 3.1–3.2 (dd, 1H, J-18 Hz, J=5 Hz), 2.35 (t, 1H, J=12 Hz), 2.15–2.22 (m, 2H), 2.08–2.14 (m, 1H), 2.0–2.5 (m, 1H), 1.85–1.92 (m, 1H), 1.31 (d, 3H, J=6), 1.30 (d, 3H, J=6) ppm Step C: [3(S),5(R),6(S),7(S)]-6-(4-Fluoro-phenyl)-3-[isopropoxy-6-(2-trifluoromethyl-imidazol-1-yl)-pyridin-2-yl]-1-oxa-spiro[4.4]non-7-ylmethyl-dimethyl-amine The title compound was prepared using standard procedure for reductive amination with sodium triacetoxyborohydride and 3 A molecular sieves in methanol, using 41 mg of [3(S),5(R),6(S),7(S)]-6-(4-fluorophenyl)-3-[3-isopropoxy-6-(2-trifluoromethyl-imidazol-1-yl)-pyridin-2-yl]-1-oxa-spiro[4.4]nonane-7-carbaldehyde (from Example 37 Step B) and dimethylamine hydrochloride. The product was flash chromatographed using 97/3/0.1% methylene chloride/methanol/ammonium hydroxide to give 31 mg of product (70% yield). $^1$H NMR (CDCl$_3$, 400 MHz) δ 7.25 (m, 2H), 7.17 (d, 1H, J=1 Hz), 7.07–7.12 (m, 3H), 6.89 (t, 2H, 9 Hz), 4.50 (sept, 1H, J=6 Hz), 4.03 (t, 1H, J=6 Hz), 3.80–3.90 (m, 1H), 3.1–3.2 (dd, 1H, J=18 Hz, J=5 Hz), 2.55–2.65 (m, 1H), 2.0–2.35 (m, 8H), 2.20 (s, 6H, [N(CH$_3$)$_2$]), 1.85–1.92 (m, 1H), 1.45–1.55 (m, 1H), 1.31 (d, 3H, J=6), 1.30 (d, 3H, J=6) ppm. Mass Spectrum (NH$_3$-CI): m/z 547 (M+H, 100%).

EXAMPLE 38

Methyl[5(R),6(S),7(S)]-6-(4-fluorophenyl)-3-[2-isopropoxy-5-(5-trifluoromethyl-tetrazol-1-yl)-pyridin-3-yl]-1-oxa-spiro[4.4]non-3-ene-7-carboxylate (Step A: 2-Hydroxy-3-bromo-5-nitropyridine In a 250 mL round bottom flask is added 2-hydroxy-3-bromo-5-nitropyridine (7.0 g, 50 mmol), bromine (14 g, 88 mmol) and 200 mL of glacial acetic acid. The mixture is refluxed for 18 hr, then another 7.5 g (47 mmol) of bromine is added and the mixture is heated for an additional 4 hrs. The solvent and excess bromine were removed under reduced pressure. The precipitate was suspended in water and filtered. It was wash with 3×25 mL of water, sucked dry, then washed with 3×30 mL of toluene. The precipitate was dried under reduced pressure at 70° C. Recovered 9.0 g of product. The yield is 86%.

Step B: 2-Isopropoxy-3-bromo-5-nitropyridine

The title compound, derived from Example 38 Step A, is prepared by suspending 12 g (55 mmol) of 2-hydroxy-3-bromo-5-nitropyridine in 100 mL of dimethylformamide. Add 25 g (165 mmol) of anydrous cesium fluoride and 2 iodopropane (28 g, 165 mmol). Heat the mixture with vigorous stirring at 70° C. for 18 hr. By TLC, no starting material is observed, only a high and low R$_f$ product. Pour the reaction mixture into 1 liter of cold water. Extract the higher R$_f$ product with 5×100 mL of hexane and purify it by flash chromatography (80/20 hexane/ethyl acetate) Recovered 5.5 g (21 mmol) of O-alkylated product (38% yield). The remainder of the material is the N-alkylated derivative. $^1$H NMR (CDCl$_3$, 400 MHz) δ 8.96 (d, 1H, J=3 Hz), 8.57 (d, 1H, J=3 Hz), 5.45 (sept, 1 H, J=6 Hz), 1.40 (d, 6H, J=6 Hz) ppm Step C: 2-Isopropoxy-3-bromo-5-aminopyridine The title compound, derived from Example 38 Step B, is prepared by dissolving 1.0 g (3.9 mmol) of 2-isopropoxy-3-bromo-5-nitropyridine in 10 mL of concentrated hydrochloric acid and 5 mL of methanol. Metallic tin (1.5 g, 2.6 mmol) is added portion-wise with vigorous stirring until TLC (95/5 methylene chloride/ethyl acetate) indicates that all the starting material is consumed. Add 25 mL of water and basify with aqueous sodium carbonate (pH-9). Extract the product with methylene chloride. Flash chromatography (95/5 methylene chloride/ethyl acetate) gave 400 mg (1.7 mmol, 44 % yielded) of product. $^1$H NMR (CDCl$_3$, 200 MHz) δ 7.59 (d, 1H, J=4 Hz), 7.29 (d, 1H, J=3 Hz), 5.15 (sept, 1H, J=6 Hz), 1.32 (d, 6H, J=6 Hz) ppm Step D: 2-Isopropoxy-3-bromo-5-trifluoroacetamidopyridine The title compound is prepared by using the procedure given in Example 6, Step F b, replacing 2-bromo-4-aminoanisole with 300 mg (1.29 mmol) of 2-isopropoxy-3-bromo-5-aminopyridine (from Example 15 (IEK) Step D). Chromatography (80/20 hexane/ethyl acetate) gives 200 mg of product (47% yield) $^1$H NMR (CDCl$_3$, 400 MHz) δ 8.16 (s, 1H), 7.23 (s, 1H), 5.27 (sept, 1H, J=6 Hz), 1.36 (d, 6H, J=6 Hz) ppm Step E: 2-Isopropoxy-3-bromo-5-(5-(trifluoromethyl)tetrazol-1-yl)pyridine The title compound was prepared by using the procedure given in Example 6, Step F c, replacing replacing N-(3-bromo-4-methoxyphenyl)-trifluoroacetamide with 200 mg (0.61 mmol) of 2-isopropoxy-3-bromo-5-trifluoroacetamidopyridine (from Example 15 (IEK) Step E). Chromatography (90/10 hexane/ethyl acetate) gave 190 mg of product (90% yield). $^1$H NMR (CDCl$_3$, 400 MHz) δ 8.20 (d, 1H, J=3 Hz), 7.92 (d, 1H, J=3 Hz), 5.42 (sept, 1H, J=6 Hz), 1.43 (d, 6H, J=6 Hz) ppm Step F: Methyl[5(R),6(S),7(S)]-6-(4-fluorophenyl)-3-[2-isopropoxy-5-(5-trifluoromethyl-tetrazol-1-yl)-pyridin-3-yl]-1-oxa-spiro[4.4]non-3-ene-7-carboxylate The title compound was prepared by using the procedure given in Example 6, Step F d, except that methyl 2-(S)-(4-fluorophenyl)cyclopentanone-3-(S)-carboxylate (from Example 5) was substituted for methyl 2-(RS)-(4-fluorophenyl)cyclopentanone-3-(RS)-carboxylate in Step A along with replacing 2-bromo-4-(5-(trifluoromethyl)tetrazol-1-yl)anisole with 190 mg (0.54 mmol) of 2-isopropoxy-3-bromo-5-(5-(trifluoromethyl)tetrazol-1-yl)pyridine (from Example 15 (IEK) Step F above). Chromatography (85/15 hexane/ethyl acetate) gave 140 mg of product (47% yield). $^1$H NMR (CDCl$_3$, 400 MHz) δ 8.1 (d, 1H, J=2 Hz), 7.21–7.27 (m, 2H), 7.17 (d, 1H, 2 Hz), 6.89 (t, 2H, 9 Hz), 6.46 (t, 1H, J=2 Hz), 5.45 (sept, 1H, J=6 Hz), 4.70 (dd, 1H J=13 Hz, J=2 Hz), 4.04 (dd, 1H J=13 Hz, J=2 Hz), 3.58 (s, 3H), 3.45 (m, 1H), 3.32 (d, 1H, J-14 Hz), 2.35–2.42 (m, 1H), 2.19–2.28 (m, 1H), 2.05–2.15 (m, 1H), 1.94–2.03 (m, 1H), 1.40 (d, 3H, J=6 Hz), 1.38 (d, 3H, J=4 Hz) ppm. Mass Spectrum (NH$_3$-CI): m/z 548 (M+H, 100%).

EXAMPLE 39

Methyl[3(S),5(R),6(S),7(S)]-6-(4-Fluorophenyl)-3-[2-isopropoxy-5-(5-trifluoromethyl-tetrazol-1-yl)-pyridin-3-yl]-1-oxa-spiro[4.4]nonane-7-carboxylate The title compound was prepared using the procedure given in Example 6, Step G, except that 50 mg (0.09 mmol) of methyl[5(R),6(S),7(S)]-6-(4-fluorophenyl)-3-[2-isopropoxy-5-(5-trifluoromethyl-tetrazol-1-yl)-pyridin-3-yl]-1-oxa-spiro[4.4]non-3-ene-7-carboxylate (Example 38 Step G) was substituted in place of methyl [3-(SR), 5-(RS), 6-(SR), 7-(SR)]-6-(4-fluorophenyl)-3-2-methoxy-5-((5-trifluoromethyl)tetrazol-1-yl)phenyl)-1-oxaspiro[4.4]nonane-7-carboxylate. After flash chromatography (90/10 hexane/ethyl acetate) we recovered 36 mg of product (72% yield). $^1$H NMR (CDCl$_3$, 400 MHz) δ 8.02 (d-1H, J=2 Hz), 7.25 (dd, 2H, J=8 Hz, J=5 Hz), 6.88 (d 1H, J=2 Hz), 6.85 (t, 2H, 9 Hz), 5.43 (sept, 1H, J=6 Hz), 4.12 (t, 1H, J=9 Hz), 3.55–3.63 (m, 1H), 3.54 (s, 3H), 3.25–3.35 (m, 1H), 3.2 (d, 1H, J=11 Hz), 3.14 (t, 1H, J=8 Hz), 2.18–2.32 (m, 2H), 1.9–2.0 (m, 1H), 1.8–1.9 (m, 1H), 1.31 (d, 3H, J=3 Hz), 1.28 (d, 3H, J=3 Hz) ppm. Mass Spectrum (NH$_3$-CI): m/z 549 (M, 100%).

EXAMPLE 40

[3(S),5(R),6(S),7(S)]-6-(4-fluorophenyl)-3-[2-isopropoxy-5-(5-trifluoromethyl-tetrazol-1-yl)-pyridin-3-yl]-1-oxa-spiro[4.4]non-7-yl}-methanol The title compound was prepared by using DIBALH in toluene with 28 mg of methyl[3(S),5(R),6(S),7(S)]-6-(4-fluorophenyl)-3-[2-isopropoxy-5-(5-trifluoromethyl-tetrazol-1-yl)-pyridin-3-yl]-1-oxa-spiro[4.4]nonane-7-carboxylate (from Example 39). After flash chromatography (90/10 hexane/ethyl acetate) we recovered 16 mg of product (56% yield). $^1$H NMR (CDCl$_3$, 400 MHz) δ 8.02 (d 1H, J=2 Hz), 7.25 (dd, 2H, J=8 Hz, J=5 Hz), 6.88 (d 1H, J=2 Hz), 6.85 (t, 2H, J=9 Hz), 5.34 (sept, 1H, J=6 Hz), 4.15 (t, 1H, J=9 Hz), 3.55–3.63 (m, 2H), 3.45 (dd, 1H, J=11 Hz, J=5 Hz), 3.11 (t, 1H, J=8 Hz), 2.69 (d, 1H, J=8 Hz), 2.6–2.7 (m, 1H), 2.10–2.23 (m, 3H), 1.6–1.7 (m, 1H), 1.26 (d, 3H, J=3 Hz), 1.24 (d, 3H, J=3 Hz) ppm. Mass Spectrum (NH$_3$-CI): m/z 522 (M+1, 100%).

EXAMPLE 41

[5(R),6(S),7(S)]-(2-fluoro-1,1-dimethyl-ethyl)-[6-(4-fluoro-phenyl)-3-[2-isopropoxy-5-(5-trifluoromethyl-tetrazol-1-yl)-pyridin-3-yl]-1-oxa-spiro[4.4]non-3-en-7-yl-methyl]-amine dihydrochloride (Step A: [5(R),6(S),7(S)]-[6-(4-fluoro-phenyl)-3-[2-isopropoxy-5-(5-trifluoromethyl-tetrazol-1-yl)-pyridin-3-yl]-1-oxa-spiro[4.4]non-3-en-7-yl]-methanol The title compound was prepared by using the procedure given in Example 6, Step F d, except that 143 mg (0.33 mmol) of [5(R),6(S),7(S)]-6-(4-fluorophenyl)-3-(2-trimethylstannyl)-1-oxaspiro[4.4]non-3-ene-7-methanol was substituted for methyl [5-(RS), 6-(SR), 7-(SR)]-6-(4-fluorophenyl)-3-(trimethylstannyl)-1-oxaspiro-[4,4]non-3-ene-7-carboxylate (from Example 6, Step E) along with replacing 2-bromo-4-(5-(trifluoromethyl)tetrazol-1-yl) anisole with 143 mg (0.33 mmol) of 2-isopropoxy-3-bromo-5-(5-(trifluoromethyl)-tetrazol-1-yl)pyridine (from Example 38 Step F.). After flash chromatography (75/25 hexane/ethyl acetate) 123 mg of product was recovered (72% yield). $^1$H NMR (CDCl$_3$, 400 MHz) δ 8.1 (d, 1H, J=2 Hz), 7.21–7.27 (m, 2H), 7.17 (d, 1H, 2 Hz), 6.89 (t, 2H, 9 Hz), 6.43 (t, 1H, J=2 Hz), 5.43 (sept, 1H, J=6 Hz), 4.70 (dd, 1H, J=13 Hz, J=2 H), 4.04 (dd, 1H J=13 Hz, J=2 Hz), 3.65 (dd, 1H, J=1 1 Hz, J=2 Hz), 3.50 (dd, 1H, J=9 Hz, J=5 Hz), 2.7–2.8 (m, 2H), 2 05–2.2 (m, 2H), 1.6–1.7 (m, 1H), 1.40 (d, 3H, J=6 Hz), 1.38 (d, 3H, J=4 Hz) ppm.

Step B: [5(R),6(S),7(S)]-6-(4-Fluorophenyl)-3-[2-isopropoxy-5-(5-trifluoromethyl-tetrazol-1-yl)-pyridin-3-yl]-1-oxa-spiro[4.4]non-3-ene-7-carbaldehyde The title compound was prepared by oxidation with Dess-Martin reagent in methylene chloride, using 52 mg of [5(R),6(S),7(S)]-[6-(4-fluoro-phenyl)-3-[2-isopropoxy-5-(5-trifluoromethyl-tetrazol-1-yl)-pyridin-3-yl]-1-oxa-spiro [4.4]non-3-en-7-yl]-methanol (from Example 41 Step A). The product was flash chromatographed using 80/20 hexane/ethyl acetate to give 25 mg of product (65% yield). The product was not characterized by NMR but was used immediately in the next step.

Step C: [5(R),6(S),7(S)]-(2-Fluoro-1,1-dimethyl-ethyl)-[6-(4-fluoro-phenyl)-3-[2-isopropoxy-5-(5-trifluoromethyl-tetrazol-1-yl)-pyridin-3-yl]-1-oxa-spiro[4.4]non-3-en-7-ylmethyl]-amine The title compound was prepared by dissolving 25 mg (0.05 mmol) of [5(R),6(S),7(S)]-6-(4-fluorophenyl)-3-[2-isopropoxy-5-(5-trifluoromethyl-tetrazol-1-yl)-pyridin-3-yl]-1-oxa-spiro[4.4]non-3-ene-7-carbaldehyde (from Example 41 Step B) in 500 μl of THF. Then α,α-dimethylamino-2-fluoroethane hydrochloride (16 mg, 0.12 mmol) was added and the mixture stirred for 15 minutes at 0° C. Diisopropylethyl amine (0.25 mmol), 20 mg of powdered 3 A sieve (Linde) and 21 mg (0.1 mmole) of sodium triacetoxyborohydride were added to the solution and it was stirred for 3 hr at 0° C. Then 2 mL of sodium bicarbonate was added to the mixture and extracted with dichloromethane. The organic layer was dried over magnesium sulfate and filtered. The solventwas removed under reduced pressure and the residue was flash chromatographed (55/45 hexane/ethyl acetate). Recovered 21 mg of product. $^1$H NMR (CDCl$_3$, 400 MHz) δ 8.1 (d, 1H, J=2 Hz), 7.25 (d, 1H, J=6 Hz), 7.22 (d, 1H, J=6 Hz), 7.20 (d, 1H, 3 Hz), 6.89 (t, 2H, 9 Hz), 6.43 (t, 1H, J=2 Hz), 5.43 (sept, 1H, J=6 Hz), 4.70 (dd, 1H, J=13 Hz, J=2 Hz), 4.08 (d, 2H, J=48 Hz, (CH$_2$-F)), 4.04 (dd, 1H J=13 Hz, J=2 Hz), 2.7–2.8 (m, 2H), 2.5–2.65 (m, 1H), 2.35–2.45 (m, 1H), 2 0–2.3 (m, 3H), 1.5–1.6 (m, 1H), 1.41 (d, 3H, J=6 Hz), 1.39 (d, 3H, J=6 Hz), 1.4–1.3 (m, 1H), 0.98 (d, 3H, J=2 Hz), 0.96 (d, 3H, J=2 Hz) ppm. Mass Spectrum (NH$_3$-CI): m/z 593 (M+1, 18% ,M-19 (fluorene) 100%).

EXAMPLE 42

[5(R),6(S),7(S)](2-Fluoro-1,1-dimethyl-ethyl)-[6-(4-fluoro-phenyl)-3-[2-isopropoxy-5-(5-trifluoromethyl-tetrazol-1-yl)-pyridin-3-yl]-1-oxa-spiro[4.4]non-2-en-7-ylmethyl]-amine dihydrochloride The title compound was prepared as the higher R$_f$ of two products obtained using the procedure given in Example 6, Step G, except that 25 mg of [5(R),6(S),7(S)]-(2-fluoro-1, 1-dimethyl-ethyl)-[6-(4-fluoro-phenyl)-3-[2-isopropoxy-5-(5-trifluoromethyl-tetrazol-1-yl)-pyridin-3-yl]-1-oxa-spiro [4.4]non-3-en-7-ylmethyl]-amine (Example 24 (IEK) Step C) was substituted in place of methyl [3-(SR), 5-(RS), 6-(SR), 7-(SR)]-6-(4-fluorophenyl)-3-2-methoxy-5-((5-trifluoromethyl)tetrazol-1-yl)phenyl)-1-oxaspiro[4.4] nonane-7-carboxylate. After flash chromatography (60/40 hexane/ethyl acetate) we recovered 3 mg of higher R$_f$ product. $^1$H NMR (CDCl$_3$, 400 MHz) δ 7.9 (d, 1H, J=2 Hz), 7.20–7.30 (m, 2H), 7.19 (s, 1H), 7.03 (d, 1H, J=3 Hz), 6.89 (t, 2H, 9 Hz), 5.40 (sept, 1H, J=6 Hz), 4.10 (bd, 2H, J=48 Hz, (CH$_2$-F)), 1.8–2.7 (m s, 6H),1.5–1.6 (m, 3H), 1.37 (d, 3H, J=6 Hz), 1.35 (d, 3H, J=6 Hz), 0.97 (bs, 3H), 0.95 (bs, 3H) ppm. Mass Spectrum (NH$_3$-CI): m/z 592 (M+1, 38% ,572 (M+1)-19 (fluorene) 100%).

EXAMPLE 43

[3(S),5(R),6(S),7(S)](2-Fluoro-1,1-dimethyl-ethyl)-{6-(4-fluorophenyl)-3-[2-isopropoxy-5-(5-trifluoromethyl-tetrazol-1-yl)-pyridin-3-yl]-1-oxa-spiro[4.4]non-7-ylmethyl}-amine dihydrochloride The title compound was prepared as the lower R$_f$ of two products obtained using the procedure given in Example 6, Step G, except that 25 mg of [5(R),6(S),7(S)]-(2-fluoro-1,1-dimethyl-ethyl)-[6-(4-fluoro-phenyl)-3-[2-isopropoxy-5-(5-trifluoromethyl-tetrazol-1-yl)-pyridin-3-yl]-1-oxa-spiro[4.4]non-3-en-7-ylmethyl]amine (Example 41 Step C) was substituted in place of methyl [3-(SR), 5-(RS), 6-(SR), 7-(SR)]-6-(4-fluorophenyl)-3-2-methoxy-5-((5-trifluoromethyl)tetrazol-1-yl)phenyl)-1-oxaspiro[4.4]nonane-7-carboxylate. After flash chromatography (60/40 hexane/ethyl acetate) we recovered 11 mg of lower $R_f$ product. $^1$H NMR (CDCl$_3$, 400 MHz) δ 8.02 (d 1H, J=2 Hz), 7.25 (dd, 2H, J=8 Hz, J=5 Hz), 6.88 (d 1H, J=2 Hz), 6.85 (t, 2H, 9 Hz), 5.33 (sept, 1H, J=6 Hz), 4.12 (m, 1H), 4.10 (bd, 2H, J=48 Hz, (CH$_2$-F)), 3.63 (m, 1H), 3.08 (t, 1H, J=8 Hz), 2.5–2.6 (m, 3H), 2.3–2.4 (m, 1H), 2.1–2.2 (m, 3H), 1.8–1.9 (m, 2H), 1.4–1.5 (m, 1H), 1.32 (d, 3H, J=4 Hz), 1.29 (d, 3H, J=4 Hz), ), 0.94 (d, 3H, J=2 Hz), 0.92 (d, 3H, J=2 Hz) ppm. Mass Spectrum (NH$_3$-CI): m/z 668 (M+1, 42%, 648 (M-19 (fluorene)) 100%).

EXAMPLE 44

[5(R),6(S),7(S)-(2-Fluoroethyl)-[6-(4-fluoro-phenyl)-3-[2-isopropoxy-5-(5-trifluoromethyl-tetrazol-1-yl)-pyridin-3-yl]-1-oxa-spiro[4.4]non-3-en-7-ylmethyl]-amine The title compound was prepared using the procedure given in Example 41, Step C using 70 mg (0.14 mmol) of [5(R),6(S),7(S)]-6-(4-fluorophenyl)-3-[2-isopropoxy-5-(5-trifluoromethyl-tetrazol-1-yl)-pyridin-3-yl]-1-oxa-spiro[4.4]non-3-ene-7-carbaldehyde (from Example 41 Step B) and 85 mg(0.86 mmol) of 1-fluoro-2-aminoethane hydrochloride. After flash chromatography (100% ethyl acetate) we recovered 52 mg of product. $^1$H NMR (CDCl$_3$, 400 MHz) δ 8.1 (d, 1H, J=2 Hz), 7.21–7.27 (m, 2H), 7.17 (d, 1H, 2 Hz), 6.89 (t, 2H, 9 Hz), 6.42 (t, 1H, J=2 Hz), 5.42 (sept, 1H, J=6 Hz), 4.69 (dd, 1H J=12 Hz, J=2 Hz), 4.41 (dt, 2H, J=47 Hz, J=3 Hz (CH$_2$-F)), 4.04 (dd, 1H J=12 Hz, J=2 Hz), 2,85-2-9 (m, 1H), 2.75–2.85 (m, 2H), 2.45–2.55 (m, 2H), 2.24–2.3 (m, 1H), 2.15–2.22 (m, 1H), 2.0–2.1 (m, 1H), 1.5–1.6 (m, 1H), 1.39 (t, 6H, J=6 Hz) ppm. Mass Spectrum (NH$_3$-CI): m/z 565 (M+H, 100%).

EXAMPLE 45

[3(S),5(R),6(S),7(S)](2-Fluoro-ethyl)-{6-(4-fluoro-phenyl)-3-[2-isopropoxy-5-(5-trifluoromethyl-tetrazol-1-yl)-pyridin-3-yl]-1-oxa-spiro[4.4]non-7-ylmethyl}-amine dihydrochloride The title compound was prepared using the procedure given in Example 6, Step G, except that 37 mg (0.065 mmol) of [5(R),6(S),7(S)-(2-fluoroethyl)-[6-(4-fluoro-phenyl)-3-[2-isopropoxy-5-(5-trifluoromethyl-tetrazol-1-yl)-pyridin-3-yl]-1-oxa-spiro[4.4]non-3-en-7-ylmethyl]-amine (Example 44) was substituted in place of methyl [3-(SR), 5-(RS), 6-(SR), 7-(SR)]-6-(4-fluorophenyl)-3-2-methoxy-5-((5-trifluoromethyl)tetrazol-1-yl)phenyl)-1-oxaspiro[4.4]nonane-7-carboxylate. After flash chromatography (75/25 hexane/ethyl acetate) we treated the product with HCl in methanol to recovered 11 mg of the dihydrochloride salt. $^1$H NMR (CDCl$_3$, 400 MHz) δ 8.02 (d 1H, J=2 Hz), 7.25 (dd, 2H, J=8 Hz, J=5 Hz), 6.88 (d 1H, J=2 Hz), 6.85 (t, 2H, 9 Hz), 5.33 (sept, 1H, J=6 Hz), 4.41 (dt, 2H, J=47 Hz, J=3 Hz (CH$_2$-F)), 4.05–4.15 (m, 2H), 3.63 (m, 1H), 3.08 (t, 1H, J=8 Hz), 2.7–2.8 (m, 2H), 2.5–2.6 (m, 2H), 2.4.–2.5 (m, 1H), 2.1–2.2 (m, 3H), 1.8–1.9 (m, 2H), 1.4–1.5 (m, 1H), 1.32 (d, 3H, J=4 Hz), 1.29 (d, 3H, J=4 Hz), 0.94 (d, 3H, J=2 Hz), 0.92 (d, 3H, J=2 Hz) ppm. Mass Spectrum (NH$_3$-CI): m/z 567 (M+1, 42%, 548 (M+1–19 (fluorene) 100%).

EXAMPLE 46

[5(R),6(S),7(S)]-(2-Fluoro-1,1-dimethyl-ethyl)-[6-(4-fluoro-phenyl)-3-(2-isopropoxy-5-trifluoromethylpyridin-3-yl)-1-oxa-spiro[4.4]non-3-en-7-yl-methyl]-amine Step A: [5(R),6(S),7(S)]-[6-(4-fluorophenyl)-3-(2-isopropoxy-5-trifluoromethylpyridin-3-yl)-1-oxa-spiro[4.4]non-3-ene-7-yl]-methanol The title compound was prepared by using the procedure given in Example 6, Step F d, except that 41 mg (0.1 mmol) of 5(R),6(S),7(S)]-6-(4-fluorophenyl)-3-(2-trimethylstannyl)-1-oxaspiro[4.4]non-3-ene-7-methanol was substituted for methyl [5-(RS), 6-(SR), 7-(SR)]-6-(4-fluorophenyl)-3-(trimethylstannyl)-1-oxaspiro-[4,4]non-3-ene-7-carboxylate (from Example 6, Step E) along with replacing 2-bromo-4-(5-(trifluoromethyl)tetrazol-1-yl) anisole with 30 mg (0.11 mmol) of 2-isopropoxy-3-bromo-5-(trifluoromethyl)pyridine. After flash chromatography (80/20 hexane/ethyl acetate) we recovered 27 mg of product (40% yield). $^1$H NMR (CDCl$_3$, 400 MHz) δ 8.21 (d, 1H, J=1 Hz), 7.21–7.27 (m, 3H), 6.89 (t, 2H, 13 Hz), 6.43 (t, 1H, J=2 Hz), 5.43 (sept, 1H, J=6 Hz), 4.72 (dd, 1H, J=13 Hz, J=2 Hz), 4.08 (dd, 1H, J=13 Hz, J=2 Hz), 3.65 (dd, 1H, J=11 Hz, J=2 Hz), 3.50 (dd, 1H, J=9 Hz, J=5 Hz), 2.7–2.8 (m, 2H), 2 05–2.2 (m, 4H), 1.6–1.7 (m, 1H), 1.34 (d, 3H, J=3 Hz), 1.33 (d, 3H, J=3 Hz) ppm.

Step B: [5(R),6(S),7(S)]-6-(4-fluorophenyl)-3-[2-isopropoxy-5-trifluoromethylpyridin-3-yl]-1-oxa-spiro[4.4]non-3-ene-7-carbaldehyde The title compound was prepared by oxidation with Dess-Martin reagent in methylene chloride, using 38 mg (0.084 mmol) of [5(R),6(S),7(S)]-[6-(4-fluorophenyl)-3-[2-isopropoxy-5-trifluoromethyl-pyridin-3-yl]-1-oxa-spiro[4.4]non-3-en-7-yl]-methanol (from Example 46 Step A). The product was flash chromatographed using 80/20 hexane/ethyl acetate to give 25 mg of product (65% yield). $^1$H NMR (CDCl$_3$, 400 MHz) δ 9.62 (d, 1H, J=2 Hz), 8.18 (d, 1H, J=1 Hz), 7.33 (m, 2H), 7.08 (d 1H, J=2 Hz), 6.89 (t, 2H, 13 Hz), 5.33 (sept, 1H, J=6 Hz), 4.08 (m, 1H), 3.50–3.60 (m, 1H), 3.33–3.4 (m, 1H), 3.15 (d, 1H,J=8 Hz), 3.09 (t, 1H, J=8 Hz), 2.2–2.3 (m, 2H), 2 05–2.1 (m, 1H) 2.0–1.9 (dd, 1H, J=15 Hz, J=8 Hz), 1.26 (d, 3H, J=6 Hz), 1.34 (d, 3H, J=6 Hz) ppm.

Step C: [5(R),6(S),7(S)]-(2-Fluoro-1,1-dimethyl-ethyl)-[6-(4-fluoro-phenyl)-3-(2-isopropoxy-5-trifluoromethylpyridin-3-yl)-1-oxa-spiro[4.4]non-3-en-7-yl-methyl]-amine The title compound was prepared by the procedure described in Example 41 Step C, except that 21 mg (0.05 mmol) of [5(R),6(S),7(S)]-6-(4-fluorophenyl)-3-[2-isopropoxy-5-trifluoromethylpyridin-3-yl]-1-oxa-spiro[4.4]non-3-ene-7-carbaldehyde (from Example 22 (IEK) Step B) was substituted for [5(R),6(S),7(S)]-6-(4-fluorophenyl)-3-[2-isopropoxy-5-(5-trifluoromethyl-tetrazol-1-yl)-pyridin-3-yl]-1-oxa-spiro[4.4]non-3-ene-7-carbaldehyde. Flash chromatography (70/30 hexane/ethyl acetate) recovered 28 mg of product. $^1$H NMR (CDCl$_3$, 400 MHz) δ 8.21 (d, 1H, J=2 Hz), 7.26 (d, 1H, J=2 Hz), 7.22 (m, 2H), 6.89 (t, 2H, 9 Hz), 6.43 (t, 1H, J=2 Hz), 5.43 (sept, 1H, J=6 Hz), 4.70 (dd, 1H J=13 Hz, J=2 Hz), 4.07 (d, 2H, J=48 Hz, (CH$_2$-F)), 4.04 (dd, 1H J=13 Hz, J=2 Hz), 2.6–2.7 (m, 2H), 2.55–2.60 (m, 1H), 2.35–2.45 (m,1H), 2 0–2.3 (m, 3H), 1.43–1.52 (m, 1H), 1.34 (d, 3H, J=4 Hz), 1.33 (d, 3H, J=4 Hz), 0.96 (d, 3H, J=2 Hz), 0.95 (d, 3H, J=2 Hz) ppm. Mass Spectrum (NH$_3$-CI): m/z 572 (M-19 (fluorene) 100%).

EXAMPLE 47

[3(S),5(R),6(S),7(S)]- (2-Fluoro-1,1-dimethyl-ethyl)-[6-(4-fluorophenyl)-3-(2-isopropoxy-5-trifluoromethylpyridin-3-yl)-1-oxa-spiro[4.4]non-7-ylmethyl]-amine The title compound was prepared using the procedure given in Example 6, Step G, except that 24 mg (0.05 mmol) of [5 (R),6(S),7(S)]-(2-fluoro-1,1-dimethyl-ethyl)-[6-(4-fluoro-phenyl)-3-(2-isopropoxy-5-trifluoromethylpyridin-3-yl)-1-oxa-spiro[4.4]non-3-en-7-yl-methyl]-amine (Example 46 Step C) was substituted in place of methyl [3-(SR), 5-(RS), 6-(SR), 7-(SR)]-6-(4-fluorophenyl)-3-2-methoxy-5-((5-trifluoromethyl)tetrazol-1-yl)phenyl)-1-oxaspiro[4.4]-nonane-7-carboxylate. After flash chromatography (60/40 hexane/ethyl acetate) 3 mg of product was obtained. $^1$H NMR (CDCl$_3$, 400 MHz) δ 8.19 (d, 1H, J=2 Hz), 7.31 (d, 1H, J=2 Hz), 7.30 (m, 2H), 7.11 (d, 1H) J=2 Hz), 6.89 (t, 2H, 9 Hz), 5.43 (sept, 1H, J=6 Hz), 4.12 (d, 2H, J=48 Hz, (CH$_2$-F)), 4.10 (t, 1H, J=8 Hz), 3.5–3.6 (m, 1H), 3.0 (t, 1H, J=8 Hz), 2.6–2.7 (m, 2H), 2.55–2.60 (m, 1H), 2.35–2.45 (m,1H), 2 1–2.3 (m, 4H), 1.8–1.95 (m, 2H, m), 1.43–1.52 (m, 1H), 1.29 (d, 3H, J=6 Hz), 1.25 (d, 3H, J=6 Hz), 0.9 (d, 6H, J=5 Hz), ppm. Mass Spectrum (NH$_3$-CI): m/z 507 (M-19 (fluorene) 526 100%), (M 28%).

EXAMPLE 48

(5R,6S,7S)-6-(4-Fluorophenyl)-3-(2-methoxy-5-(2-(trifluoromethyl)imidazol-1-yl)phenyl)-1-oxaspiro [4.4]non-3-ene-7-carboxylic acid methyl ester Step A: 1-(3-Bromo-4-methoxyphenyl)-2-(trifluoromethyl)-imidazole Triphenylphosphine (2.1 g, 8.0 mmol) was added in portions to a suspension of N-(3-bromo-4-methoxyphenyl)-2,2,2-trifluoroacetamide (2.0 g, 6.7 mmol) in 40 mL of carbon tetrachloride at 80° C., and stirring was continued at 80° C. overnight. An additional portion of triphenylphosphine (2.1 g, 8.0 mmol) was added and stirring was continued for 2.5 h at 80° C. After cooling to room temperature, the mixture was concentrated under reduced pressure. The residue was treated with 50 mL of boiling hexane and filtered. The undissolved material was treated with 100 mL of boiling hexane and filtered. The combined filtrates were concentrated. The resulting residue was treated with hexane at room temperature and filtered. Concentration of the filtrate yielded 2.95 g of brown oil. NMR indicated that this crude material contained 1.83 g (5.78 mmol) of the intermediate chloroimidate. Aminoacetaldehyde diethyl acetal (2.52 mL, 17.3 mmol) was added dropwise to an ice cold solution of the crude chloroimidate in 20 mL of THF. After 30 min at 0° C., the mixture was stirred for 2.5 h with slow warming to 25° C. The mixture was concentrated in vacuo, and the residue was dissolved in 55 mL of acetic acid and heated at reflux for 1.5 h. After cooling to room temperature, the acetic acid was removed in vacuo. The residue was partitioned between 100 mL of ethyl acetate and 50 mL of 2.5 N aq. sodium hydroxide, and the aqueous layer was then extracted with 2×100 mL of ethyl acetate. The combined ethyl acetate layers were washed with 100 mL of brine, dried over sodium sulfate, and evaporated. Flash column chromatography on 150 g of silica gel eluting with 2 L of 10% ethyl acetate/hexane followed by 1 L of 20% of ethyl acetate/hexane yielded 1-(3-bromo-4-methoxyphenyl)-2-(trifluoromethyl)imidazole (1.22 g, 65% yield) as amber crystals. $^1$H NMR (400 MHz, CDCl$_3$): δ 7.58 (d, 1 H, J=3 Hz), 7.31 (dd, 1 H, J=9, 3 Hz), 7.21 (d, 1 H, J=1 Hz), 7.21 (d, 1 H, J=1 Hz), 6.98 (d, 1 H, J=9 Hz), 3.97 (s, 3H). Mass spectrum (NH$_3$CI): m/e=321 (M+1).

Step B: (5R,6S,7S)-6-(4-Fluorophenyl)-3-(2-methoxy-5-(2-(trifluoromethyl)imidazol-1-yl)phenyl)-1-oxaspiro-[4.4] non-3-ene-7-carboxylic acid methyl ester The title compound was prepared by using the procedure given of Example 6, Step F d), replacing 2-bromo-4-(5-(trifluoromethyl)tetrazol-1-yl)anisole with 1-(3-bromo-4-methoxy-phenyl)-2-(trifluoromethyl)imidazole (from Step A above). $^1$H NMR (400 MHz, CDCl$_3$): δ 7.27 (dd, 2 H, J=9, 6 Hz), 7.20 (dd, 1 H, J=9, 2 Hz), 7.18 (d, 1 H, J=1 Hz), 7.07 (d, 1 H, J=1 Hz), 6.93 (d, 1 H, J=9 Hz), 6.89 (t, 2 H, J=9 Hz), 6.84 (d, 1 H, J=2 Hz), 6.36 (t, 1 H, J=2 Hz), 4.71 (dd, 1 H,J=12, 2 Hz), 4.05 (dd, 1 H, J=12, 2 Hz), 3.90 (s, 3 H), 3.59 (s, 3 H), 3.46 (dt, 1 H, J=11, 8 Hz), 3.32 (d, 1 H, J=11 Hz), 2.41–2.21 (m, 2 H), 2.14–1.94 (m, 2 H). Mass spectrum (NH$_3$CI): m/e=517 (M+1).

EXAMPLE 49

(3S,5R,6S,7S)-6-(4-Fluorophenyl)-3-[2-methyl-6-(5-trifluoromethyl-tetrazol-1-yl)-benzooxazol-4-yl]-1-oxa-spiro[4.4]non-3-ene-7-carboxylic acid methyl ester Step A: 2-Bromo-6-methoxy-4-nitro-phenylamine 47.64 g of bromine in 120 mL of AcOH was added dropwise to a solution of 47.64 g of 2-methoxy-4nitro-aniline in 240 ml of AcOH at 0° C. Upon addition a precipitate formed. Mixture was stirred for 30 minutes and then filtered. The precipitate was washed with satd. NaHSO$_3$, water, and vaccum dried, giving 24 g of title compound as a bright yellow powder.

Step B: N-(2-bromo-6-methoxy-4-nitrophenyl)acetamide

A solution of 23 g of 2-bromo-6-methoxy-4-nitrophenylamine in 125 mL of acetic anhydride and 100 mL of AcOH was refluxed at 110° C. Following reflux for 5 h, mixture was dumped into 1.5 L of ice water. A precipitate formed, and was collected via filtration. The precipitate was then placed in EtOH and refluxed for 15 min. 9 mL of conc. NH$_4$OH was then added to the hot mixture. The solution was then cooled, and a precipitate formed and collected again via filtration. The solid was washed with ethanol(2×) and ether, and allowed to air dry. 21.5 g of title compound as a tan powder was collected.

Step C: N-(2-bromo-6-hydroxy-4-nitrophenyl)acetamide

To a slurry of 1.26 g of N-(2-bromo-6-methoxy-4-nitrophenyl)acetamide and 60 mL of methylene chloride at 0° C., 8.7 mL of 1.0 M BBr$_3$ in methylene chloride was added dropwise. The mixture was slowly warmed to rt. and allowed to react overnight. MeOH was added next morning and allowed to stir for 10 min. TLC(50/50 hexane/EtOAc) showed reaction complete, different conditions(90/10 DCM/EtOAc) showed there to be two products. Added satd. NaHCO$_3$, extracted with EtOAc(2×), dried organic over MgSO$_4$ and conc. in vacuo. Recovered 1.16 g of product, NMR(CDCl$_3$ 400 MHz) showed the two products to be desired and 4-bromo-2-methyl-6-nitro-benzooxazole. The product was carried on with no fiuther purification.

Step D: 4-Bromo-2-methyl-6-nitro-benzooxazole

A solution of 1.15 g of N-(2-bromo-6-hydroxy-4-nitrophenyl)acetamide, 80 mg Tosic acid, 26 mg DMAP, in 25 mL 1,3-dichorobenzene was heated at 170° C. overnight. Reaction was then washed with satd. NaHCO$_3$ and brine, dried over MgSO$_4$, and conc. in vacuo. The product was purified on a silica gel column, eluting with 80% hexane/ 20% EtOAc. 910 mg of title compound was recovered.

Step E: 4-Bromo-2-methyl-6-amino-benzooxazole

To a solution of 720 mg of 4-bromo-2-methyl-6-nitro-benzooxazole in 45 mL ETOH was added 642 mg of iron powder and 8.5 mL of AcOH. Solution was refluxed for 2.5 h, during which a chalky white color formed. Solvent was removed, solid was dissolved back into DCM and filtered through Celite. The filtrate was washed with satd. NaHCO$_3$ and brine, dried over MgSO$_4$, and solvent evaporated. 690 mg of title compound as a brown solid was recovered.

Step F: 4-Bromo-2-methyl-6-(5-trifluoromethyl-tetrazol-1-yl)-benzooxazole

Compound was prepared according to the procedure given in Example 6, Step F (b & c) using 4-bromo-2-methyl-6-amino-benzooxazole in place of 2-Bromo-4-(trifluoroacetamido)anisole and 2-Bromo-4-(5-(trifluoromethyl)tetrazol-1-yl)anisole.

Step G: (3 S,5R,6S,7S)-6-(4-Fluoro-phenyl)-3-[2-methyl-6-(5-trifluromethyl-tetrazol-1-yl)-benzooxazol-4-yl]-1-oxa-spiro[4.4]non-3-ene-7-carboxylic acid methyl ester The compound was prepared according to the procedure given in Example 6, Step F (d) using 4-bromo-2-methyl-6-(5-trifluoromethyl-tetrazol-1-yl)-benzooxazole in place of 2-bromo-4-(5-(trifluoromethyl)tetrazol-1-yl)anisole and used chiral (5R, 6S, 7S) instead of racemic mixture. $^1$NMR (400 MHz, CDCl$_3$)): δ 1.95–2.05 (m, 1H), 2.1–2.2 (m, 1H), 2.28–2.42 (m, 2H), 2.72 (s, 3H), 3.37–3.5 (m, 2H), 3.57 (s, 3H), 4.15–4.2 (dd, 1H), 4.83–4.87 (dd, 1H), 6.85 (t, J=9, 2H), 6.89 (d, J=2, 1H), 7.03 (m,1H), 7.26–7.28 (m, 2H), 7.48 (d, J=1H). MS (NH$_3$/ESI): m/e=544.3 (M+1).

EXAMPLE 50

(3S,5R,6S,7S)-6-(4-Fluorophenyl)-3-[2-methyl-6-(5-trifluromethyl-tetrazol-1-yl)-benzooxazol-4-yl]-1-oxa-spiro[4.4]nonane-7-carboxylic acid methyl ester The title compound was prepared by the procedure given in Example 6, Step G, employing (3S,5R,6S,7S)-6-(4-fluoro-phenyl)-3-[2-methyl-6-(5-trifluromethyl-tetrazol-1-yl)-benzooxazol-4-yl]-1-oxa-spiro[4.4]non-3-ene-7-carboxylic acid methyl ester in place of methyl [5-(RS), 6-(SR), 7-(SR)]-6-(4-fluorophenyl)-3-(2-methoxy-5-((5-trifluoromethyl)tetrazol-1-yl)phenyl)-1-oxaspiro[4.4]non-3-ene-7-carboxylate, except that AcOH was not used as a cosolvent and reaction was hydrogenated with a hydrogen balloon at atmospheric pressure. $^1$H NMR (400 MHz, CDCl$_3$): δ 1.9–2.0 (m, 2H), 2.05–2.1 (m, 1H), 2.15–2.42(m, 3H), 2.64 (s, 3H), 3.2 (d, 1H), 3.28–3.38 (m, 2H), 3.54 (s, 3H), 3.95–4.06 (m, 1H), 4.15–4.2 (t, 1H), 6.63 (d, J=2, 1H), 6.84–6.889 (m, 2H), 7.28–7.32 (m, 2H), 7.39 (d, J=2, 1H). MS (NH$_3$/ESI): m/e=546.3 (M+1).

EXAMPLE 51

(3S,5R,6S,7S)-6-(4-Fluorophenyl)-3-(2-methyl-5-trifluromethyl-benzooxazol-7-yl)-1-oxa-spiro[4.4] non-3-ene-7-carboxylic acid methyl ester Step A: 2-Bromo-4-trifluoromethyl-6-nitro-phenol 4.0 g of bromine in 7.3 mL of AcOH was added dropwise to a solution of 4.0 g of 2-nitro-4-trifluoromethyl-phenol and 300 mg FeCl$_3$ in 23.1 mL of AcOH at 0° C. Reaction was then heated at 40° C. for 1.5 h. and then allowed to stir for 65 h at rt. Solvent was then removed, placed solid back into EtOAc, filtered through celite and concentrated in vacuo. 5 g of title compound was collected.

Step B: 7-bromo-2-methyl-5-trifluoromethyl-benzooxazole

Compound was prepared according to the procedure given in Example Steps B and D using 2-bromo-4-trifluoromethyl-6-nitrophenol in place of 2-bromo-6-methoxy-4-nitro-phenylamine.

Step C: (3S,5R,6S,7S)-6-(4-Fluoro-phenyl)-3-(2-methyl-5-trifluromethyl-benzooxazol-7-yl)-1-oxa-spiro[4.4]non-3-ene-7-carboxylic acid methyl ester The compound was prepared according to the procedure given in Example 6, Step F (d) 7-bromo-2-methyl-5-trifluoromethyl-benzooxazole in place of 2-bromo-4-(5-(trifluoromethyl)tetrazol-1-yl)anisole and used chiral (5R, 6S, 7S) instead of racemic mixture. $^1$H NMR (400 MHz, CDC$_{13}$): δ 1.95–2.05 (m, 1H), 2.08–2.15 (m, 1H), 2.25–2.41 (m, 2H), 2.71 (s, 3H), 3.36–3.42 (m, 1H), 3.42 (m, 1H), 3.57 (s, 3H), 4.21–4.24 (dd, 1H), 4.6 (dd, J=10, 2, 1H), 6.56 (d,J=2, 1H), 6.84–6.89 (m, 2H), 7.04 (s, 1H), 7.25–7.3 (m, 2H), 7.76 (s, 1 H). MS (NH$_3$/CI): m/e=476.1 (M+1).

EXAMPLE 52

(3S,5R,6S,7S)-6-(4-Fluorophenyl)-3-(2-methyl-5-trifluoromethyl-benzooxazol-7-yl)-1-oxa-spiro[4.4] nonane-7-carboxylic acid methyl ester The title compound was prepared by the procedure given in Example 6, Step G, employing (3S,5R,6S,7S)-6-(4-fluoro-phenyl)-3-[2-methyl-6-(5-trifluromethyl-tetrazol-1-yl)-benzooxazol-4-yl]-1-oxa-spiro[4.4]non-3-ene-7-carboxylic acid methyl ester in place of methyl [5-(RS), 6-(SR), 7-(SR)]-6-(4-fluorophenyl)-3-(2-methoxy-5-((5-trifluoromethyl)tetrazol-1-yl)phenyl)-1-oxaspiro[4.4]non-3-ene-7-carboxylate, except reaction was placed on hydrogenator at 45 p.s.i for 1 week and a equimolar amount of Pd(OH)$_2$ was used. $^1$H NMR (400 MHz, CDCl$_3$): δ 1.9–2.05 (m, 2H), 2.05–2.35 (m, 4H), 2.51 (s, 3H), 3.25 (d, 1H), 3.28–3.38 (m, 2H), 3.56 (s, 3H), 3.65–3.75 (m, 1H), 4.1 (t, 1H), 6.9–7.05 (m, 3H), 7.1–7.2 (m, 1 H), 7.32–7.4 (m, 2H). MS: m/e=478.0 (M+1)

EXAMPLE 53

(3S,5R,6S,7S)-6-(4-Fluorophenyl)-3-[2-methyl-5-(5-trifluromethyl-tetrazol-1-yl)-benzooxazol-7-yl]-1-oxa-spiro[4.4]non-3-ene-7-carboxylic acid methyl ester Step A: 2-Bromo-4,6-dinitro-phenol The title compound was prepared by the procedure given in Example 51 Step A, using 2,4-dinitro-phenol in place of 2-nitro-4-trifluoromethyl-phenol.

Step B: 2-Amino-4-nitro-6-bromo-phenol 10 g of NH$_4$Cl and 2 mL of NH$_4$OH were added to a solution of 4.7 g of 2-bromo-4,6-dinitro-phenol and 50 mL of water. The mixture was heated to 85° C., and then cooled to 70° C. At this point 5.2 g of Na$_2$S-9H$_2$O was added, keeping reaction between 80–85° C. After addition, reaction was heated for 2 h at 85° C. Solution was then cooled in ice bath, and resulting precipitate was collected via filtration. The solid was then placed in 30 mL of water, brought to a boil, acidified with AcOH, along with 170 mg of norit being added. The solution was filtered hot, then cooled with 1.97 g of title compound crystalizing out of solution. The compound was carried on without further purification.

Step C: (3S,5R,6S,7S)-6-(4-Fluorophenyl)-3-[2-methyl-5-(5-trifluromethyl-tetrazol-1-yl)-benzooxazol-7-yl]-1-oxa-spiro[4.4]non-3-ene-7-carboxylic acid methyl ester The tide compound was prepared by the procedure given in Example 49, steps B, D-G, using 2-amino-4-nitro-6-bromo-phenol in place of 2-Bromo-6-methoxy-4-nitro-phenylamine. $^1$H NMR (400 MHz, CDCl$_3$): δ 1.95–2.05 (m, 1H), 2.1–2.18 (m, 1H), 2.27–2.42(m, 2H), 2.76 (s, 3H), 3.38–3.50 (m, 2H), 4.18 (dd, J=10,2, 1H), 4.82 (dd, J=10, 2, 1H), 6.64 (t, J=2, 1H), 6.85–6.91 (m, 3H), 7.25–7.28 (m, 2H), 7.64 (d, J=2, 1H). MS (NH$_3$/CI): m/e=544.2 (M+1).

EXAMPLE 54

(3S,5R,6S,7S)-6-(4-Fluorophenyl)-3-[2-methyl-5-(5-trifluromethyl-tetrazol-1-yl)-benzooxazol-7-yl]-1-oxa-spiro[4.4]non-2-ene-7-carboxylic acid methyl ester The title compound was prepared by the procedure given in Example 6, Step G, employing (3S,5R,6S,7S)-6(4-fluorophenyl)-3-[2-methyl-6-(5-trifluromethyl-tetrazol-1-yl)-benzooxazol-4-yl]-1-oxa-spiro[4.4]non-3-ene-7-carboxylic acid methyl ester in place of methyl [5-(RS), 6-(SR), 7-(SR)]-6-(4-fluorophenyl)-3-(2-methoxy-5-((5-trifluoromethyl)tetrazol-1-yl)phenyl)-1-oxaspiro[4.4]non-3-ene-7-carboxylate, except reaction was placed on hydrogenator at 45 p.s.i for 32 h. Two products were seen via TLC (70/30 Hexane/EtOAc), reaction mixture was purified on silica gel column, eluting with 70/30 hexane EtOAc, this was the top spot. $^1$H NMR (400 MHz, CDCl$_3$): δ 2.05–2.1 (m, 2H), 2.35–2.42 (m, 2H), 2.68 (s, 3H), 2.93(t, J=2, 2H), 3.30 (d, 1H), 3.35–3.42 (m, 1H), 3.58 (s, 3H), 6.84 (d, J=2, 1H), 6.91 (t, J=9, 2H), 7.17 (s, 1H), 7.26–7.30 (m, 2H), 7.44 (d, J=2, 1H). MS (NH$_3$/CI): m/e=544.0 (M+1).

EXAMPLE 55

(3S,5R,6S,7S)-6-(4-Fluorophenyl)-3-[2-methyl-5-(5-trifluromethyl-tetrazol-1-yl)-benzooxazol-7-yl]-1-oxa-spiro[4.4]nonane-7-carboxylic acid methyl ester The title compound was prepared by the procedure given in Example 6, Step G, employing (3S,5R,6S,7S)-6-(4-fluoro-phenyl)-3-[2-methyl-6-(5-trifluoromethyl-tetrazol-1-yl)-benzooxazol-4-yl]-1-oxa-spiro[4.4]non-3-ene-7-carboxylic acid methyl ester in place of methyl [5-(RS), 6-(SR), 7-(SR)]-6-(4-fluorophenyl)-3-(2-methoxy-5-((5-trifluoromethyl)tetrazol-1-yl)phenyl)-1-oxaspiro[4.4]non-3-ene-7-carboxylate, except reaction was placed on hydrogenator at 45 p.s.i for 32 h. Two spots were seen on TLC (70/30 Hexane/EtOAc). The product was purified on silica gel column, eluting with 70/30 hexane EtOAc, this was the lower spot. $^1$H NMR (400 MHz, CDCl$_3$): δ 1.92–1.99 (m, 2H), 2.06–2.38 (m, 4H), 2.58 (s, 3H), 3.23 (d, J11, 1H), 3.3–3.4 (m, 2H), 3.55 (s, 3H), 3.7–3.82 (m, 1H), 4.12–4.18 (t, 1H), 6.78 (d, J=2, 1H), 6.92 (t, J=9, 2H), 7.33 (q, J=5, 2H), 7.54 (d, J=2, 1H) (NH$_3$/CI): m/e=546.0 (M+1).

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:
1. A compound of the formula:

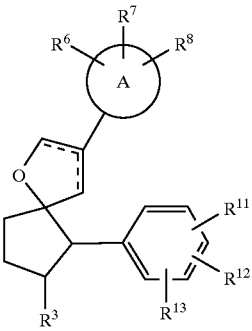

I or a pharmaceutically acceptable salt thereof, wherein:
R$^3$ is selected from the group consisting of:
  (1) hydrogen,
  (2) C$_{1-8}$ alkyl,
  (3) —R$^4$, and
  (4) C$_{1-6}$ alkyl substituted with —R$^4$;
R$^4$ is selected from the group consisting of:
  (1) hydroxy,
  (2) C$_{1-6}$ alkoxy,
  (3) phenyl-C$_{1-3}$ alkoxy,
  (4) phenyl,
  (5) —CN,
  (6) halo, wherein halo is fluoro, chloro, bromo or iodo,
  (7) —NR$^9$R$^{10}$, wherein R$^9$ and R$^{10}$ are independently selected from:
    (a) hydrogen,
    (b) C$_{1-6}$ alkyl,
    (c) C$_{2-6}$ alkenyl,
    (d) C$_{2-6}$ alkoxy,
    (e) phenyl,
    (f) (C$_{1-6}$ alkyl)-phenyl,
    (g) (C$_{1-6}$ alkyl)-hydroxy,
    (h) (C$_{1-6}$ alkyl)-halo,
    (i) (C$_{1-6}$ alkyl)-poly-halo,
    (j) (C$_{1-6}$ alkyl)—CONR$^{11}$R$^{12}$, wherein R$^{11}$ and R$^{12}$ are independendy selected from hydrogen and C$_{1-4}$ alkyl, and
    (k) (C$_{1-6}$ alkyl)-(C$_{1-4}$ alkoxy),
    or R$^9$ and R$^{10}$ may be joined together to form a 3–8 membered heterocyclic ring which may contain another hetero group selected from: —O—, —NH—, —N(C$_{1-6}$ alkyl)-, and —S—;
  (8) —NR$^9$—COR$^{10}$,
  (9) —NR$^9$—CO$_2$R$^{10}$,
  (10) —CO—NR$^9$R$^{10}$,
  (11) —COR$^9$,
  (12) —CO$_2$R$^9$,
  (13) heterocycle, wherein the heterocycle is selected from the group consisting of:
    (A) benzimidazolyl,
    (B) benzofuranyl,
    (C) benzothiophenyl,
    (D) benzoxazolyl,
    (E) furanyl,
    (F) imidazolyl,
    (G) indolyl,
    (H) isooxazolyl,
    (I) isothiazolyl,
    (J) oxadiazolyl, (K) oxazolyl,
(L) pyrazinyl,
(M) pyrazolyl,
(N) pyridyl,
(O) pyrimidyl,
(P) pyrrolyl,
(Q) quinolyl,
(R) tetrazolyl,
(S) thiadiazolyl,
(T) thiazolyl,
(U) thienyl,
(V) triazolyl,
(W) azetidinyl,
(X) 1,4-dioxanyl,
(Y) hexahydroazepinyl,
(Z) piperazinyl,
(AA) piperidinyl,
(AB) pyrrolidinyl,
(AC) morpholinyl,
(AC) thiomorpholinyl,
(AD) dihydrobenzimidazolyl,
(AE) dihydrobenzofuranyl,
(AF) dihydrobenzothiophenyl,
(AG) dihydrobenzoxazolyl,
(AH) dihydrofuranyl
(AI) dihydroimidazolyl,
(AJ) dihydroindolyl,
(AK) dihydroisooxazolyl,
(AL) dihydroisothiazolyl,
(AM) dihydrooxadiazolyl,
(AN) dihydrooxazolyl,
(AO) dihydropyrazinyl,
(AP) dihydropyrazolyl,
(AQ) dihydropyridinyl,
(AR) dihydropyrimidinyl,
(AS) dihydropyrrolyl,
(AT) dihydroquinolinyl,
(AU) dihydrotetrazolyl,
(AV) dihydrothiadiazolyl,
(AW) dihydrothiazolyl,
(AX) dihydrothienyl,
(AY) dihydrotriazolyl,
(AZ) dihydroazetidinyl,
(BA) tetrahydrofuranyl, and
(BB) tetrahydrothienyl,
and wherein the heterocycle is unsubstituted or substituted with one or more substituent(s) selected from:
(i) $C_{1-6}$ alkyl, unsubstituted or substituted with halo, $—CF_3$, $—OCH_3$, or phenyl,
(ii) $C_{1-6}$ alkoxy,
(iii) oxo,
(iv) hydroxy,
(v) thioxo,
(vi) $—SR^9$,
(vii) halo,
(viii) cyano,
(ix) phenyl,
(x) trifluoromethyl,
(xi) $—(CH_2)_p—NR^9R^{10}$, wherein p is 0, 1, 2, 3 or 4,
(xii) $—NR^9COR^{10}$,
(xiii) $—CONR^9R^{10}$,
(xiv) $—CO_2R^9$, and
(xv) $—(CH_2)_p—OR^9$,
(14) $—CO$—heterocycle, wherein heterocycle is as defined above,
(15) $—NR^9$—heterocycle, wherein heterocycle is as defined above,
(16) $—NR^9—C_{1-4}$ alkyl-heterocycle, wherein heterocycle is as defined above;
the circle A is a heteroaryl moiety which is selected from the group consisting of:
(A) benzimidazolyl,
(B) benzofuranyl,
(D) benzodihydrofuranyl,
(F) benzoxazolyl,
(I) indolyl,
(P) pyridyl,
(Y) dihydrobenzimidazolyl,
(Z) dihydrobenzofuranyl,
(AB) dihydrobenzoxazolyl,
(AE) dihydroindolyl,
(AK) dihydropyridinyl,
and wherein the heteroaryl moiety is unsubstituted or substituted with one or more substituent(s) selected from:
(i) $C_{1-6}$ alkyl, unsubstituted or substituted with halo, $—CF_3$, $—OCH_3$, or phenyl,
(ii) $C_{1-6}$ alkoxy,
(iii) oxo,
(iv) hydroxy,
(v) thioxo,
(vi) $—SR^9$,
(vii) halo,
(viii) cyano,
(ix) phenyl,
(x) trifluoromethyl,
(xi) $—(CH_2)_p—NR^9R^{10}$,
(xii) $—NR^9COR^{10}$,
(xiii) $—CONR^9R^{10}$,
(xiv) $—CO_2R^9$, and
(xv) $—(CH_2)_p—OR^9$;
$R^6$, $R^7$ and $R^8$ are independently selected from the group consisting of:
(1) hydrogen,
(2) $C_{1-6}$ alkoxy,
(3) halo,
(4) $C_{1-6}$ alkyl, unsubstituted or substituted with one or more of the substituents selected from:
(a) hydroxy,
(b) oxo,
(c) $C_{1-6}$ alkoxy,
(d) phenyl-$C_{1-3}$ alkoxy,
(e) phenyl,
(f) $—CN$,
(g) halo,
(h) $—NR^9R^{10}$,
(i) $—NR^9—COR^{10}$,
(j) $—NR^9—CO_2R^{10}$,
(k) $—CO—NR^9R^{10}$,
(l) $—COR^9$,
(m) $—CO_2R^9$,
(n) heterocycle, wherein heterocycle is as defined above,
(5) hydroxy,
(6) $—CN$,
(7) $—CF_3$,
(8) $—OCF_3$,
(9) $—OCF_2H$,
(10) $—OCFH_2$,
(11) $—NO_2$,
(12) $—SR^{14}$, wherein $R^{14}$ is hydrogen or $C_{1-6}$ alkyl,
(13) $—SOR^{14}$,
(14) $—SO_2R^{14}$,

(15) —NR$^9$—COR$^{10}$,
(16) —CO—NR$^9$—COR$^{10}$,
(17) —NR$^9$R$^{10}$,
(18) —NR$^9$—CO$_2$R$^{10}$,
(19) —COR$^9$,
(20) —CO$_2$R$^9$,
(21) heterocycle, wherein heterocycle is as defined above,
(22) —(C$_{1-6}$ alkyl)-heterocycle, wherein heterocycle is as defined above, and
(23) —N(heterocycle)—SO$_2$R$^{14}$, wherein heterocycle is as defined above;

R11, R$^{12}$ and R$^{13}$ are independently selected from:
(1) hydrogen,
(2) C$_{1-6}$ alkyl, unsubstituted or substituted with one or more of the substituents selected from:
   (a) hydroxy,
   (b) oxo,
   (c) C$_{1-6}$ alkoxy,
   (d) phenyl-C$_{1-3}$ alkoxy,
   (e) phenyl,
   (f) —CN,
   (g) halo,
   (h) —NR$^9$R$^{10}$,
   (i) —NR$^9$—COR$^{10}$,
   (j) —NR$^9$—CO$_2$R$^{10}$,
   (k) —CO-NR$^9$R$^{10}$,
   (l) —COR$^9$, and
   (m) —CO$_2$R$^9$,
(3) halo,
(4) —CN,
(5) —CF$_3$,
(6) —NO$_2$,
(7) hydroxy,
(8) C$_{1-6}$ alkoxy,
(9) —COR$^9$, and
(10) —CO$_2$R$^9$;

each of the two dashed lines denotes the presence of either a single or a double bond between the indicated carbon atoms, with the proviso that at least one of the dashed lines indicates the presence of a single bond.

2. The compound of claim 1, or a pharmaceutically acceptable salt thereof, wherein:
R$^3$ is selected from the group consisting of:
(1) —R$^4$, and
(2) C$_{1-6}$ alkyl substituted with —R$^4$;
R$^4$ is selected from the group consisting of:
(1) —NR$^9$R$^{10}$, wherein R$^9$ and R$^{10}$ are independently selected from:
   (a) hydrogen,
   (b) C$_{1-6}$ alkyl,
   (c) (C$_{1-6}$ alkyl)-hydroxy, and
   (d) (C$_{1-6}$ alkyl)-(C$_{1-4}$ alkoxy),
(2) —CO-NR$^9$R$^{10}$,
(3) —NR$^9$—COR$^{10}$,
(4) heterocycle, wherein the heterocycle is selected from the group consisting of:
   (A) imidazolyl,
   (B) triazolyl,
   (C) tetrazolyl,
   (D) pyridyl,
   (E) piperazinyl,
   (F) piperidinyl,
   (G) pyrrolidinyl,
   (H) morpholinyl,
   and wherein the heterocycle is unsubstituted or substituted with one or more substituent(s) selected from:
   (i) C$_{1-6}$ alkyl, unsubstituted or substituted with halo, —CF$_3$, —OCH$_3$, or phenyl,
   (ii) C$_{1-6}$ alkoxy,
   (iii) oxo, and
   (iv) hydroxy,
(5) —CO-heterocycle, wherein heterocycle is as defined above;

the circle A is a heteroaryl moiety which is selected from the group consisting of:
(A) benzofuranyl,
(B) indolyl,
(D) pyridyl,
(F) dihydrobenzofuranyl,
and wherein the heteroaryl moiety is unsubstituted or substituted with one or more substituent(s) selected from:
(i) C$_{1-6}$ alkyl, unsubstituted or substituted with halo, —CF$_3$, —OCH$_3$, or phenyl,
(ii) C$_{1-6}$ alkoxy,
(iii) oxo,
(iv) hydroxy,
(v) thioxo,
(vi) —SR$^9$,
(vii) halo,
(viii) cyano,
(ix) phenyl,
(x) trifluoromethyl,
(xi) —(CH$_2$)$_p$-NR$^9$R$^{10}$,
(xii) —NR$^9$COR$^{10}$,
(xiii) —CONR$^9$R$^{10}$,
(xiv) —CO$_2$R$^9$, and
(xv) —(CH$_2$)$_p$-OR$^9$;

R$^6$, R$^7$ and R$^8$ are independently selected from the group consisting of:
(1) hydrogen,
(2) —CF$_3$,
(3) —OCF$_3$,
(4) —F,
(5) C$_{1-6}$ alkyl,
(6) C$_{1-6}$ alkoxy, and
(7) heterocycle, wherein the heterocycle is selected from the group consisting of:
   (A) imidazolyl,
   (B) triazolyl,
   (C) tetrazolyl,
   (D) pyridyl,
   (E) piperazinyl,
   (F) piperidinyl,
   (G) pyrrolidinyl, and
   (H) morpholinyl,
   and wherein the heterocycle is unsubstituted or substituted with one or more substituent(s) selected from:
   (i) C$_{1-6}$ alkyl, unsubstituted or substituted with halo, —CF$_3$, —OCH$_3$, or phenyl,
   (ii) C$_{1-6}$ alkoxy,
   (iii) oxo, and
   (iv) hydroxy;

R$^{11}$, R$^{12}$ and R$^{13}$ are independently selected from:
(1) hydrogen, and
(2) fluoro;

each of the two dashed lines denotes the presence of either a single or a double bond between the indicated carbon atoms, with the proviso that at least one of the dashed lines indicates the presence of a single bond.

3. The compound of claim 1, or a pharmaceutically acceptable salt thereof, wherein R$^3$ is selected from the group consisting of:

(1) —CH₂-N(C₁₋₆ alkyl)(C₁₋₆ alkyl),
(2) —CH₂-NH(C₁₋₆ alkyl),
(3) —CH₂-N(C₁₋₆ alkyl)(CH₂CH₂-F),
(4) —CH₂-pyrrolidinyl,
(5) —CH₂-morpholinyl,
(6) —N(C₁₋₆ alkyl)(C₁₋₆ alkyl), and
(7) —NH(C₁₋₆ alkyl).

4. The compound of claim 1, or a pharmaceutically acceptable salt thereof, wherein R³ is —R⁴ or C₁₋₆ alkyl substituted with —R⁴, and R⁴ is selected from the group consisting of:
(1) —NR⁹R¹⁰, wherein R⁹ and R¹⁰ are independently selected from:
 (a) hydrogen,
 (b) C₁₋₆ alkyl,
 (c) (C₁₋₆ alkyl)-hydroxy, and
 (d) (C₁₋₆ alkyl)-halo,
(2) —CO-NR⁹R¹⁰,
(3) —NR⁹—COR¹⁰,
(4) heterocycle, wherein the heterocycle is selected from the group consisting of:
 (A) imidazolyl,
 (B) triazolyl,
 (C) tetrazolyl,
 (D) pyridyl,
 (E) piperazinyl,
 (F) piperidinyl,
 (G) pyrrolidinyl,
 (H) morpholinyl,
 and wherein the heterocycle is unsubstituted or substituted with one or more substituent(s) selected from:
  (i) C₁₋₆ alkyl, unsubstituted or substituted with halo, —CF₃, —OCH₃, or phenyl,
  (ii) C₁₋₆ alkoxy,
  (iii) oxo, and
  (iv) hydroxy,
(5) —CO-heterocycle, wherein heterocycle is as defined above.

5. The compound of claim 1, or a pharmaceutically acceptable salt thereof, wherein A is selected from the group consisting of:
(D) pyridyl,
 and wherein the heterocycle is unsubstituted or substituted with one or more substituent(s) selected from:
 (i) C₁₋₆ alkyl, unsubstituted or substituted with halo, —CF₃, —OCH₃, or phenyl,
 (ii) C₁₋₆ alkoxy,
 (iii) oxo, and
 (iv) hydroxy.

6. The compound of claim 1, or a pharmaceutically acceptable salt thereof, wherein R⁶, R⁷ and R⁸ are independently selected from the group consisting of:
(1) hydrogen,
(2) —CF₃,
(3) —OCF₃,
(4) C₁₋₄ alkoxy, and
(5) heterocycle, wherein the heterocycle is selected from the group consisting of:
 (A) tetrazolyl,
 (B) imidazolyl,
 (C) triazolyl,
 (D) pyridyl, and
 (E) isooxazolyl,
 and wherein the heterocycle is unsubstituted or substituted with one or more substituent(s) selected from:
  (i) C₁₋₄ alkyl,
  (ii) -cyclopropyl, and
  (iii) —CF₃.

7. The compound of claim 1, or a pharmaceutically acceptable salt thereof, wherein R¹¹, R¹² and R¹³ are independently selected from:
(1) hydrogen, and
(2) fluoro.

8. The compound of claim 1, or a pharmaceutically acceptable salt thereof, wherein the phenyl ring bearing R¹¹, R¹² and R¹³ is unsubstituted phenyl or para-fluorophenyl.

9. A compound which is selected from the group consisting of:

(5R,6S,7S)-6-(4-fluorophenyl)-3-[2-methoxy-5-(5-trifluoromethyl-tetrazol-1-yl)-pyridin-3-yl]-1-oxaspiro[4.4]non-3-ene-7-carboxylic acid methyl ester;

(3S,5R,6S,7S)-6-(4-fluorophenyl)-3-[2-methoxy-5-(5-trifluoromethyl-tetrazol-1-yl)-pyridin-3-yl]-1-oxaspiro[4.4]nonane-7-carboxylic acid methyl ester;

(5R,6S,7S)-6-(4-fluorophenyl)-3-[2-methoxy-5-(5-trifluoromethyl-tetrazol-1-yl)-pyridin-2-yl]-1-oxaspiro[4.4]non-3-ene-7-carboxylic acid methyl ester;

(3S,5R,6S,7S)-6-(4-fluorophenyl)-3-[3-methoxy-6-(5-trifluoromethyl-tetrazol-1-yl)-pyridin-2-yl]-1-oxaspiro[4.4]nonane-7-carboxylic acid methyl ester;

(5R,6S,7S)-6-(4-fluorophenyl)-3-[5-trifluoromethoxy-dihydrobenzo-furan-7-yl]-1-oxaspiro[4.4]non-3-ene-7-carboxylic acid methyl ester;

(5R,6S, 7S)-6-(4-fluorophenyl)-3-(1-methyl-5-trifluoromethyl-benz-imidazol-7-yl)-1-oxaspiro[4.4]non-3-ene-7-carboxylic acid methyl ester;

(5R,6S, 7S)-6-(4-fluorophenyl)-3-[1-(tert-butyloxycarbonyl)-6-trifluoromethyl-benzimidazol-4-yl]-1-oxaspiro[4.4]non-3-ene-7-carboxylic acid methyl ester;

(5R, 6S, 7S)-6-(4-fluorophenyl)-3-(5-trifluoromethyl-benzimidazol-7-yl)-1-oxaspiro[4.4]nonane-7-carboxylic acid methyl ester;

(5R, 6S, 7S)-6-(4-fluorophenyl)-3-(((5-trifluoromethyl)tetrazol-1-yl)-1H-indol-7-yl)-1-oxaspiro[4.4]non-3-ene-7-carboxylic acid methyl ester;

(5R, 6S, 7S)-6-(4-fluorophenyl)-3-(((5-trifluoromethyl)tetrazol-1-yl)-1H-indol-7-yl)-1-oxaspiro[4.4]nonane-7-carboxylic acid methyl ester;

(3S,5R,6S,7S)-6-(4-fluorophenyl)-3-[3-methoxy-6-(5-trifluoromethyl-tetrazol-1-yl)-pyridin-2-yl]-1-oxaspiro[4.4]nonane-7-carboxylic acid methyl ester;

(5R,6S,7S)-6-(4-fluorophenyl)-3-[5-trifluoromethoxy-dihydrobenzo-furan-7-yl]-1-oxaspiro[4.4]non-3-ene-7-carboxylic acid methyl ester;

(5 R,6S, 7S)-6-(4-fluorophenyl)-3-(1-methyl-5-trifluoromethyl-benz-imidazol-7-yl)-1-oxaspiro[4.4]non-3-ene-7-carboxylic acid methyl ester;

(5 R,6S, 7S)-6-(4-fluorophenyl)-3-[1-(tert-butyloxycarbonyl)-6-trifluoromethyl-benzimidazol-4-yl]-1-oxaspiro[4.4]non-3-ene-7-carboxylic acid methyl ester;

(5R, 6S, 7S)-6-(4-fluorophenyl)-3-(5-trifluoromethyl-benzimidazol-7-yl)-1-oxaspiro[4.4]nonane-7-carboxylic acid methyl ester;

(5R, 6S, 7S)-6-(4-fluorophenyl)-3-(((5-trifluoromethyl)tetrazol-1-yl)-1H-indol-7-yl)-1-oxaspiro[4.4]non-3-ene-7-carboxylic acid methyl ester;

(5R, 6S, 7S)-6-(4-fluorophenyl)-3-(((5-trifluoromethyl)tetrazol-1-yl)-1H-indol-7-yl)-1-oxaspiro[4.4]nonane-7-carboxylic acid methyl ester;

(3S, 5R, 6S, 7S)-6-(4-fluorophenyl)-3-(((5-trifluoromethyl)tetrazol-1-yl)-1H-indol-7-yl)-1-oxaspiro[4.4]nonane-7-methanol;

(3S, 5R, 6S, 7S)-7-(dimethylaminomethyl)-6-(4-fluorophenyl)-3-(((5-trifluoromethyl)tetrazol-1-yl)-1H-indol-7-yl)-1-oxaspiro[4.4]nonane;

(5R, 6S, 7S)-7-6-(4-fluorophenyl)-3-(((5-trifluoromethyl)tetrazol-1-yl)-1-methyl-indol-7-yl)-1-oxaspiro[4.4]non-3-ene-7-methanol;

(3S, 5R, 6S, 7S)-7-6-(4-fluorophenyl)-3-(((5-trifluoromethyl)tetrazol-1-yl)-1-methyl-indol-7-yl)-1-oxaspiro[4.4]nonane-7-methanol;

(5R, 6S, 7S)-7-(2-fluoroethylaminomethyl)-6-(4-fluorophenyl)-3-(((5-trifluoromethyl)tetrazol-1-yl)-1-methyl-indol-7-yl)-1-oxaspiro[4.4]non-3-ene;

methyl [5(R),6(S),7(S)]-$^6$-(4-fluorophenyl)-3-(3-methoxy-6-(2-tri-fluoromethyl-imidazol-1-yl)-pyridin-2-yl)-1-oxa-spiro[4.4]non-3-ene-7-carboxylate;

methyl [5(R),6(S),7(S)]-6-(4-fluorophenyl)-3-[3-methoxy-6-(2-trifluoromethyl-imidazol-1-yl)-pyridin-2-yl]-1-oxa-spiro[4.4]non-2-ene-7-carboxylate;

methyl [3(S),5(R),6(S),7(S)]-6-(4-fluorophenyl)-3-[3-methoxy-6-(2-trifluoromethylimidazol-1-yl)-pyridin-2-yl]-1-oxa-spiro[4.4]nonane-7-carboxylate;

[5(R),6(S),7(S)]-6-(4-fluorophenyl)-3-[3-methoxy-6-(2-trifluoromethyl-imidazol-1-yl)pyridin-2-yl]-1-oxa-spiro[4.4]non-3-en-7-methanol;

[5(R),6(S),7(S)]-6-(4-fluorophenyl)-3-[3-methoxy-6-(2-trifluoromethyl imidazol-1-yl)-pyridin-2-yl]-1-oxa-spiro[4.4]non-3-en-7-amine;

[5(R),6(S),7(S)]-6-(4-fluorophenyl)-3-[3-methoxy-6-(2-trifluoromethyl imidazol-1-yl)-pyridin-2-yl]-1-oxa-spiro[4.4]non-3-en-7-methylamine;

[3(S),5(R),6(S),7(S)]-6-(4-fluorophenyl)-3-[3-methoxy-6-(2-trifluoromethylimidazol-1-yl)-pyridin-2-yl]-1-oxa-spiro[4.4]non-7-yl-methylamine;

[3(S),5(R),6(S),7(S)]-6-(4-fluorophenyl)-3-[3-methoxy-6-(2-trifluoromethyl-imidazol-1-yl)-pyridin-2-yl]-1-oxa-spiro[4.4]non-7-yl-methanol;

[3 (S),5(R),6(S),7(S)]-6-(4-fluorophenyl)-3-[3-methoxy-6-(2-trifluoromethyl-imidazol 1-yl)-pyridin-2-yl]-1-oxa-spiro[4.4]non-7-ylmethyl-dimethyl-amine;

methyl [5(R),6(S),7(S)]-6-(4-fluoro-phenyl)-3-[3-hydroxy-6-(2-trifluoromethyl-imidazol-1-yl)-pyridin-2-yl]-1-oxa-spiro[4.4]non-3-ene-7-carboxylate;

methyl [5(R),6(S),7(S)]-3-[3-difluoromethoxy-6-(2-trifluoromethyl-imidazol-1-yl)-pyridin-2-yl]-6(4-fluorophenyl)-1-oxa-spiro[4.4]non-3-ene-7-carboxylate;

[3(R),5(R),6(S),7(S)]-6-(4-fluorophenyl)-3-[3-methoxy-6-(2-trifluoromethyl-imidazol-1-yl)-pyridin-2-yl]-1-oxa-spiro[4.4]non-7-yl }-methanol;

methyl [5(R),6(S),7(S)]-6-(4-fluoro-phenyl)-3-[3-isopropoxy-6-(2-trifluoromethyl-imidazol-1-yl)-pyridin-2-yl]-1-oxa-spiro[4.4]non-3-ene-7-carboxylate;

methyl [5(R),6(S),7(S)]-6-(4-fluorophenyl)-3-[3- isopropoxy -6-(2-trifluoromethyl-imidazol-1-yl)-pyridin-2-yl]-1-oxa-spiro[4.4]non-2-ene-7-carboxylate;

methyl [3(S),5(R),6(S),7(S)]-6-(4-fluorophenyl)-3-[3-isopropoxy-6-(2-trifluoromethylimidazol-1-yl)-pyridin-2-yl]-1-oxa-spiro[4.4]nonane-7-carboxylate;

[3(S),5(R),6(S),7(S)]-6-(4-fluorophenyl)-3-[3-isopropoxy-6-(2-trifluoromethyl-imidazol-1-yl)-pyridin-2-yl]-1-oxa-spiro[4.4]non-7-ylmethyl-dimethylamine;

methyl[5(R),6(S),7 (S)]-6-(4-fluorophenyl)-3-[2-isopropoxy-5-(5-trifluoromethyl-tetrazol-1-yl)-pyridin-3-yl]-1-oxa-spiro[4.4]non-3-ene-7-carboxylate;

methyl[3(S),5(R),6(S),7(S)]-6-(4-fluorophenyl)-3-[2-isopropoxy-5-(5-trifluoromethyl-tetrazol-1-yl)-pyridin-3-yl]-1-oxa-spiro[4.4]nonane-7-carboxylate;

[3(S),5(R),6(S),7(S)]-6-(4-fluorophenyl)-3-[2-isopropoxy-5-(5-trifluoromethyl-tetrazol-1-yl)-pyridin-3-yl]-1-oxa-spiro[4.4]non-7-yl }-methanol;

[5(R),6(S),7(S)]-(2-fluoro-1,1-dimethyl-ethyl)-[6-(4-fluoro-phenyl)-3-[2-isopropoxy-5-(5-trifluoromethyl-tetrazol-1-yl)-pyridin-3-yl]-1-oxa-spiro[4.4]non-3-en-7-yl-methyl]-amine;

[5(R),6(S),7(S)](2-fluoro-1,1-dimethyl-ethyl)-[6-(4-fluoro-phenyl)-3-[2-isopropoxy-5-(5-trifluoromethyl-tetrazol-1-yl)-pyridin-3-yl]-1-oxa-spiro[4.4]non-2-en-7-ylmethyl]-amine;

[3(S),5(R),6(S),7(S)](2-fluoro-1,1-dimethyl-ethyl)- {6-(4-fluoro-phenyl)-3-(2-isopropoxy-5-(5-trifluoromethyl-tetrazol-1-yl)-pyridin-3-yl]-1-oxa-spiro[4.4]non-7-ylmethyl }-amine;

[5(R),6(S),7(S)]-(2-fluoroethyl)-[6-(4-fluoro-phenyl)-3-[2-isopropoxy-5-(5-trifluoromethyl-tetrazol-1-yl)-pyridin-3-yl]-1-oxa-spiro[4.4]non-3-en-7-ylmethyl]-amine;

[3(S),5(R),6(S),7(S)](2-fluoro-ethyl)- {6-(4-fluoro-phenyl)-3-[2-isopropoxy-5-(5-trifluoromethyl-tetrazol-1-yl)-pyridin-3-yl]-1-oxa-spiro[4.4]non-7-ylmethyl }-amine;

[5(R),6(S),7(S)]-(2-fluoro-1,1-dimethyl-ethyl)-[6-(4-fluoro-phenyl)-3-(2-isopropoxy-5-trifluoromethylpyridin-3-yl)-1-oxa-spiro[4.4]non-3-en-7-yl-methyl]-amine;

[3(S),5(R),6(S),7(S)]-(2-fluoro-1,1-dimethyl-ethyl)-[6-(4-fluoro-phenyl)-3-(2-isopropoxy-5-trifluoromethylpyridin-3-yl)-1-oxa-spiro[4.4]non-7-ylmethyl]-amine;

(5R,6S,7S)-6-(4-fluorophenyl)-3-(2-methoxy-5-(2-(trifluoro-methyl)imidazol-1-yl)phenyl)-1-oxaspiro[4.4]non-3-ene-7-carboxylic acid methyl ester;

(3S,5R,6S,7S)-6-(4-fluorophenyl)-3-[2-methyl-6-(5-trifluoromethyl-tetrazol-1-yl)-benzooxazol-4-yl]-1-oxa-spiro[4.4]non-3-ene-7-carboxylic acid methyl ester;

(3S,5R,6S,7S)-6-(4-fluorophenyl)-3-[2-methyl-6-(5-trifluromethyl-tetrazol-1-yl)-benzooxazol-4-yl]-1-oxa-spiro[4.4]nonane-7-carboxylic acid methyl ester;

(3S ,5R,6S ,7S)-6-(4-fluorophenyl)-3-(2-methyl-5-trifluromethyl-benzooxazol-7-yl)-1-oxa-spiro[4.4]non-3-ene-7-carboxylic acid methyl ester;

(3S ,5R,6S ,7S)-6-(4-fluorophenyl)-3-(2-methyl-5-trifluoromethyl-benzooxazol-7-yl)-1-oxa-spiro[4.4]nonane-7-carboxylic acid methyl ester;

(3S ,5R,6S ,7S)-6-(4-fluorophenyl)-3-[2-methyl-5-(5-trifluromethyl-tetrazol-1-yl)-benzooxazol-7-yl]-1-oxa-spiro[4.4]non-3-ene-7-carboxylic acid methyl ester;

(3S,5R,6S,7S)-6-(4-fluorophenyl)-3-[2-methyl-5-(5-trifluromethyl-tetrazol-1-yl)-benzooxazol-7-yl]-1-oxa-spiro[4.4]non-2-ene-7-carboxylic acid methyl ester;

(3S,5R,6S,7S)-6-(4-fluorophenyl)-3-[2-methyl-5-(5-trifluromethyl-tetrazol-1-yl)-benzooxazol-7-yl]-1-oxa-spiro[4.4]nonane-7-carboxylic acid methyl ester;

and pharmaceutically acceptable salts and individual diasteromers thereof.

10. A pharmaceutical composition comprising a pharmaceutically acceptable carrier and an effective amount of the compound of claim 1.

11. A pharmaceutical composition comprising a pharmaceutically acceptable carrier and an effective amount of the compound of claim 9.

12. A method for antagonizing the effect of substance P at its receptor site or for the blockade of neurokinin-1 receptors in a mammal which comprises the administration to the mammal of the compound of claim 1 in an amount that is effective for antagonizing the effect of substance P at its receptor site or for the blockade of neurokinin-1 receptors in the mammal.

13. A method for antagonizing the effect of substance P at its receptor site or for the blockade of neurokinin-1 receptors in a mammal which comprises the administration to the mammal of the compound of claim 9 in an amount that is effective for antagonizing the effect of substance P at its receptor site or for the blockade of neurokinin-1 receptors in the mammal.

* * * * *